(12) United States Patent
Castillo et al.

(10) Patent No.: US 8,518,876 B2
(45) Date of Patent: Aug. 27, 2013

(54) COMPOSITION FOR LONG-ACTING PEPTIDE ANALOGS

(75) Inventors: Gerardo M. Castillo, Bothell, WA (US); Elijah M. Bolotin, Bothell, WA (US)

(73) Assignee: Pharmaln Corporation, Bothell, WA (US)

( * ) Notice: Subject to any disclaimer, the term of this patent is extended or adjusted under 35 U.S.C. 154(b) by 0 days.

(21) Appl. No.: 13/095,753

(22) Filed: Apr. 27, 2011

(65) Prior Publication Data

US 2011/0207662 A1 Aug. 25, 2011

Related U.S. Application Data

(63) Continuation of application No. 12/184,186, filed on Jul. 31, 2008, now Pat. No. 7,960,336.

(60) Provisional application No. 60/953,789, filed on Aug. 3, 2007.

(51) Int. Cl.
*A61K 38/02* (2006.01)
*A61K 38/22* (2006.01)
*C07K 2/00* (2006.01)
*C07K 14/575* (2006.01)

(52) U.S. Cl.
USPC .......... 514/7.2; 514/11.7; 514/12.4; 530/324; 530/345

(58) Field of Classification Search
None
See application file for complete search history.

(56) References Cited

U.S. PATENT DOCUMENTS

| | | | |
|---|---|---|---|
| 3,998,795 A | 12/1976 | Sarantakis | |
| 4,801,580 A * | 1/1989 | Kitaura et al. | 530/330 |

(Continued)

FOREIGN PATENT DOCUMENTS

| | | |
|---|---|---|
| EP | 0381446 B1 | 8/1994 |
| JP | 10158195 | 6/1998 |

(Continued)

OTHER PUBLICATIONS

Holm et al. Side-chain and backbone amide bond requirements for glycopeptide stimulation . . . Bioorganic & Medicinal Chemistry. Jun. 9, 2006, vol. 14, pp. 5921-5932.*

(Continued)

*Primary Examiner* — Jeffrey E Russel
(74) *Attorney, Agent, or Firm* — Wilson Sonsini Goodrich & Rosati

(57) ABSTRACT

The invention describes compositions of peptide analogs that are active in blood or cleavable in blood to release an active peptide. The peptide analogs have a general formula: A-$(Cm)_x$-Peptide (SEQ ID NO: 76), wherein A is hydrophobic moiety or a metal binding moiety, e.g., a chemical group or moiety containing 1) an alkyl group having 6 to 36 carbon units, 2) a nitrilotriacetic acid group, 3) an imidodiacetic acid group, or 4) a moiety of formula $(Z_y His_w)_p$ (SEQ ID NO: 50), wherein Z is any amino acid residue other than histidine, His is histidine, y is an integer from 0-6; w is an integer from 1-6; and p is an integer from 1-6; wherein if A has alkyl group with 6 to 36 carbon units x is greater than 0; and Cm is a cleavable moiety consisting of glycine or alanine or lysine or arginine or N-Arginine or N-lysine, wherein x is an integer between 0-6 and N may be any amino acid or none. The peptide analogs are complexed with polymeric carrier to provide enhanced half-life.

20 Claims, 23 Drawing Sheets

Lysine Vasopressin Analog with C12 ester linked through lactate

(56) References Cited

U.S. PATENT DOCUMENTS

| | | | |
|---|---|---|---|
| 4,857,311 | A | 8/1989 | Domb et al. |
| 5,019,383 | A | 5/1991 | Hopp |
| 5,118,666 | A | 6/1992 | Habener |
| 5,120,712 | A | 6/1992 | Habener |
| 5,527,524 | A | 6/1996 | Tomalia et al. |
| 5,554,388 | A | 9/1996 | Illum |
| 5,593,658 | A | 1/1997 | Bogdanov et al. |
| 5,605,672 | A | 2/1997 | Bogdanov et al. |
| 5,614,492 | A | 3/1997 | Habener |
| 5,631,018 | A | 5/1997 | Zalipsky et al. |
| 5,661,025 | A | 8/1997 | Szoka, Jr. et al. |
| 5,663,387 | A | 9/1997 | Singh |
| 5,681,544 | A | 10/1997 | Schmitt-Willich et al. |
| 5,714,166 | A | 2/1998 | Tomalia et al. |
| 5,744,166 | A | 4/1998 | Illum |
| 5,753,611 | A * | 5/1998 | Franssen et al. ........... 424/134.1 |
| 5,763,585 | A | 6/1998 | Nag |
| 5,837,747 | A | 11/1998 | Soon-Shiong et al. |
| 5,871,710 | A | 2/1999 | Bogdanov et al. |
| 5,891,418 | A | 4/1999 | Sharma |
| 5,958,909 | A | 9/1999 | Habener |
| 5,977,084 | A | 11/1999 | Szoka, Jr. et al. |
| 5,990,273 | A | 11/1999 | Andersson et al. |
| 6,006,753 | A | 12/1999 | Efendic |
| 6,051,549 | A | 4/2000 | Roberts et al. |
| 6,113,946 | A | 9/2000 | Szoka, Jr. et al. |
| 6,124,273 | A | 9/2000 | Drohan et al. |
| 6,162,462 | A | 12/2000 | Bolotin et al. |
| 6,177,274 | B1 | 1/2001 | Park et al. |
| 6,232,366 | B1 | 5/2001 | Wang et al. |
| 6,274,175 | B1 | 8/2001 | Gombotz et al. |
| 6,284,727 | B1 | 9/2001 | Kim et al. |
| 6,338,859 | B1 | 1/2002 | Leroux et al. |
| 6,348,069 | B1 | 2/2002 | Vacanti et al. |
| 6,365,173 | B1 | 4/2002 | Domb et al. |
| 6,395,299 | B1 | 5/2002 | Babich et al. |
| 6,443,898 | B1 | 9/2002 | Unger et al. |
| 6,447,753 | B2 | 9/2002 | Edwards et al. |
| 6,458,373 | B1 | 10/2002 | Lambert et al. |
| 6,468,532 | B1 | 10/2002 | Hsei et al. |
| 6,475,779 | B2 | 11/2002 | Mathiowitz et al. |
| 6,492,560 | B2 | 12/2002 | Wilbur et al. |
| 6,509,323 | B1 | 1/2003 | Davis et al. |
| 6,521,211 | B1 | 2/2003 | Unger et al. |
| 6,521,736 | B2 | 2/2003 | Watterson et al. |
| 6,576,254 | B1 | 6/2003 | Uchegbu |
| 6,579,851 | B2 | 6/2003 | Goeke et al. |
| 6,583,111 | B1 | 6/2003 | DiMarchi et al. |
| 6,586,524 | B2 | 7/2003 | Sagara et al. |
| 6,589,549 | B2 | 7/2003 | Shih et al. |
| 6,627,228 | B1 | 9/2003 | Milstein et al. |
| 6,703,037 | B1 | 3/2004 | Hubbell et al. |
| 6,703,359 | B1 | 3/2004 | Young et al. |
| 6,706,689 | B2 | 3/2004 | Coolidge et al. |
| 6,747,006 | B2 | 6/2004 | Efendic |
| 6,828,303 | B2 | 12/2004 | Kim et al. |
| 6,849,708 | B1 | 2/2005 | Habener |
| 6,884,628 | B2 | 4/2005 | Hubbell et al. |
| 6,894,024 | B2 | 5/2005 | Coolidge et al. |
| 6,899,883 | B2 | 5/2005 | Dupre |
| 6,982,248 | B2 | 1/2006 | Coolidge et al. |
| 6,992,060 | B2 | 1/2006 | Brand |
| 6,998,137 | B2 | 2/2006 | Shih et al. |
| 7,049,284 | B2 | 5/2006 | Drucker |
| 7,101,843 | B2 | 9/2006 | Glaesner et al. |
| 7,138,105 | B2 | 11/2006 | Bolotin |
| 7,138,486 | B2 | 11/2006 | Habener |
| 7,144,863 | B2 | 12/2006 | DeFelippis et al. |
| 7,199,217 | B2 | 4/2007 | DiMarchi et al. |
| 7,259,233 | B2 | 8/2007 | Dodd et al. |
| 7,319,000 | B1 | 1/2008 | Sastry et al. |
| 7,534,449 | B2 | 5/2009 | Saltzman et al. |
| 7,790,140 | B2 | 9/2010 | Bolotin |
| 7,960,336 | B2 | 6/2011 | Castillo et al. |
| 2001/0006817 | A1 | 7/2001 | Pack et al. |
| 2002/0015737 | A1 | 2/2002 | Shih et al. |
| 2002/0132254 | A1 | 9/2002 | Twu |
| 2003/0050237 | A1 | 3/2003 | Kim et al. |
| 2003/0119734 | A1 | 6/2003 | Flink et al. |
| 2003/0138407 | A1 | 7/2003 | Lu et al. |
| 2003/0220251 | A1 | 11/2003 | Knudsen et al. |
| 2003/0224974 | A1 | 12/2003 | Bolotin |
| 2003/0229034 | A1 | 12/2003 | Waugh et al. |
| 2003/0232968 | A1 | 12/2003 | Li et al. |
| 2004/0018176 | A1 | 1/2004 | Tolentino et al. |
| 2004/0077840 | A1 | 4/2004 | Granoff et al. |
| 2004/0092432 | A1 | 5/2004 | During et al. |
| 2004/0106589 | A1 | 6/2004 | Webb et al. |
| 2004/0162241 | A1 | 8/2004 | Efendic |
| 2004/0197369 | A1 | 10/2004 | Hubbell et al. |
| 2004/0209803 | A1 | 10/2004 | Baron et al. |
| 2004/0220105 | A1 | 11/2004 | Jensen et al. |
| 2004/0235726 | A1 | 11/2004 | Jakubowski et al. |
| 2004/0266683 | A1 | 12/2004 | Hathaway et al. |
| 2005/0008661 | A1 | 1/2005 | Fereira et al. |
| 2005/0014681 | A1 | 1/2005 | Minamitake et al. |
| 2005/0037075 | A1 | 2/2005 | Farokhzad et al. |
| 2005/0143303 | A1 | 6/2005 | Quay et al. |
| 2005/0148497 | A1 | 7/2005 | Khan et al. |
| 2005/0153913 | A1 | 7/2005 | Kosak |
| 2005/0159356 | A1 | 7/2005 | Dong et al. |
| 2005/0215475 | A1 | 9/2005 | Ong et al. |
| 2005/0239705 | A1 | 10/2005 | Dake et al. |
| 2005/0260259 | A1 | 11/2005 | Bolotin |
| 2006/0003935 | A1 | 1/2006 | Pan et al. |
| 2006/0014695 | A1 | 1/2006 | Ghandehari et al. |
| 2006/0019874 | A1 | 1/2006 | Radhakrishnan et al. |
| 2006/0030838 | A1 | 2/2006 | Gonnelli |
| 2006/0035815 | A1 | 2/2006 | Chen et al. |
| 2006/0040879 | A1 | 2/2006 | Kosak |
| 2006/0057137 | A1 | 3/2006 | Steiness |
| 2006/0074025 | A1 | 4/2006 | Quay et al. |
| 2006/0093660 | A1 | 5/2006 | Bolotin |
| 2006/0128627 | A1 | 6/2006 | Goke et al. |
| 2006/0172001 | A1 | 8/2006 | Ong et al. |
| 2006/0172003 | A1 | 8/2006 | Meers et al. |
| 2006/0178304 | A1 | 8/2006 | Juul-Mortensen et al. |
| 2006/0183682 | A1 | 8/2006 | Juul-Mortensen |
| 2006/0199763 | A1 | 9/2006 | Knudsen et al. |
| 2006/0233857 | A1 | 10/2006 | Amsden et al. |
| 2006/0239924 | A1 | 10/2006 | Bolotin |
| 2006/0247167 | A1 | 11/2006 | Schlein et al. |
| 2006/0286129 | A1 | 12/2006 | Sarubbi |
| 2007/0036806 | A1 | 2/2007 | Glaesner et al. |
| 2007/0041951 | A1 | 2/2007 | Egan et al. |
| 2007/0141006 | A1 | 6/2007 | Livoreil et al. |
| 2007/0141145 | A1 | 6/2007 | Castillo et al. |
| 2007/0219118 | A1 | 9/2007 | Lu et al. |
| 2007/0225213 | A1 | 9/2007 | Kosak |
| 2007/0244296 | A1 | 10/2007 | Tomalia et al. |
| 2007/0298006 | A1 | 12/2007 | Tomalia et al. |
| 2008/0015263 | A1 | 1/2008 | Bolotin et al. |
| 2008/0026995 | A1 | 1/2008 | Tosi et al. |
| 2008/0159992 | A1 | 7/2008 | Rotman et al. |
| 2008/0312174 | A1 | 12/2008 | Yu et al. |
| 2009/0053169 | A1 | 2/2009 | Castillo et al. |
| 2009/0156459 | A1 | 6/2009 | Castillo et al. |
| 2010/0233084 | A1 | 9/2010 | Narasimhaswamy et al. |
| 2010/0234279 | A1 | 9/2010 | Castillo et al. |

FOREIGN PATENT DOCUMENTS

| | | |
|---|---|---|
| WO | WO 94/05203 A1 | 3/1994 |
| WO | WO 97/33552 A1 | 9/1997 |
| WO | WO 98/42383 A1 | 10/1998 |
| WO | WO 01/28569 A1 | 4/2001 |
| WO | WO 01/39815 A2 | 6/2001 |
| WO | WO 01/39815 A3 | 1/2002 |
| WO | WO 02/24213 A2 | 3/2002 |
| WO | WO 02/24213 A3 | 6/2002 |
| WO | WO 03/070749 A2 | 8/2003 |
| WO | WO 03/072143 A1 | 9/2003 |
| WO | WO 2004/014451 A1 | 2/2004 |
| WO | WO 2004/022004 A2 | 3/2004 |
| WO | WO 03/070749 A3 | 4/2004 |

| | | | |
|---|---|---|---|
| WO | WO 2004/022004 A3 | 12/2004 |
| WO | WO 2005/076998 A2 | 8/2005 |
| WO | WO 2005/084180 A2 | 9/2005 |
| WO | WO 2005/084180 A3 | 12/2005 |
| WO | WO 2005/076998 A3 | 1/2006 |
| WO | WO 2006/062398 A2 | 6/2006 |
| WO | WO 2006/062398 A3 | 10/2006 |
| WO | WO 2007/024899 A2 | 3/2007 |
| WO | WO 2007/030706 A1 | 3/2007 |
| WO | WO 2007/048190 A1 | 5/2007 |
| WO | WO 2007/056681 A2 | 5/2007 |
| WO | WO 2007/082331 A1 | 7/2007 |
| WO | WO 2007/024899 A3 | 11/2007 |
| WO | WO 2007/056681 A3 | 4/2008 |

OTHER PUBLICATIONS

Ahren, et al. Improved glucose tolerance and insulin secretion by inhibition of dipeptidyl peptidase IV in mice. Eur J Pharmacol. Sep. 15, 2000;404(1-2):239-45.

Aigner, A. Applications of RNA interference: current state and prospects for siRNA-based strategies in vivo. Appl Microbiol Biotechnol. Aug. 2007;76(1):9-21.

Baigude, et al. Design and creation of new nanomaterials for therapeutic RNAi. ACS Chem Biol. Apr. 24, 2007;2(4):237-41.

Behlke, M. Progress towards in vivo use of siRNAs. Mol Ther. Apr. 2006;13(4):644-70.

Bogdanov, et al. A new macromolecule as a contrast agent for MR angiography: preparation, properties, and animal studies. Radiology. Jun. 1993;187(3):701-6.

Bogdanov, et al. Long-circulating blood pool imaging agents. Advanced Drug Delivery Reviews. 1995; 335-348.

Bogdanov, JR, et al. Merging molecular imaging and RNA interference: early experience in live animals. J Cell Biochem. Jul. 1, 2008;104(4):1113-23.

Bonner-Weir, et al. Imaging the Pancreatic Beta Cell. JDFI Workshop. Apr. 1999.

Brand, et al. Pharmacological treatment of chronic diabetes by stimulating pancreatic beta-cell regeneration with systemic co-administration of EGF and gastrin. Pharmacol Toxicol. Dec. 2002;91(6):414-20.

Bulotta, et al. Cultured pancreatic ductal cells undergo cell cycle re-distribution and beta-cell-like differentiation in response to glucagon-like peptide-1. J Mol Endocrinol. Dec. 2002;29(3):347-60.

Buteau, et al. Glucagon-like peptide-1 promotes DNA synthesis, activates phosphatidylinositol 3-kinase and increases transcription factor pancreatic and duodenal homeobox gene 1 (PDX-1) DNA binding activity in beta (INS-1)-cells. Diabetologia. Jul. 1999;42(7):856-64.

Cadranel, et al. Omeprazole efficacy and tolerance in 20 patients with longstanding Zollinger-Ellison syndrome. Gastroenterol Clin Biol. 1989; 13(8-9):654-62. (in French with English Summary).

Caliceti, et al. Pharmacokinetic and biodistribution properties of poly(ethylene glycol)-protein conjugates. Adv Drug Deliv Rev. Sep. 26, 2003;55(10):1261-77.

Callahan, et al. Preclinical evaluation and phase I clinical trial of a 99mTc-labeled synthetic polymer used in blood pool imaging. AJR Am J Roentgenol. Jul. 1998;171(1):137-43.

Chen, et al. A novel gene delivery system using EGF receptor-mediated endocytosis. FEBS Lett. Jan. 31, 1994;338(2):167-9.

Chollet, et al. Side-effects of a systemic injection of linear polyethylenimine-DNA complexes. J Gene Med. Jan.-Feb. 2002;4(1):84-91.

Chowdhury, et al. Fate of DNA targeted to the liver by asialoglycoprotein receptor-mediated endocytosis in vivo. Prolonged persistence in cytoplasmic vesicles after partial hepatectomy. J Biol Chem. May 25, 1993;268(15):11265-71.

Clark, et al. Guide for the Care and Use of Laboratory Animals. Institute of Laboratory Animal Resources. National Academy Press. Washington, D.C. 1996.

Cras-Meneur, et al. Epidermal growth factor increases undifferentiated pancreatic embryonic cells in vitro: a balance between proliferation and differentiation. Diabetes 2001; 50(7):1571-1579.

Creutzfeldt, et al.Is Hypergastrinaemia dangerous to man? Scand J Gastroenterol Suppl. 1991; 180:179-191.

Cunningham, et al. Dimerization of human growth hormone by zinc. Science. Aug. 2, 1991;253(5019):545-8.

Dash, et al. Synthetic polymers for vectorial delivery of DNA: characterisation of polymer-DNA complexes by photon correlation spectroscopy and stability to nuclease degradation and disruption by polyanions in vitro. Journal of Controlled Release, 1997; 48: 269-276.

De Fougerolles, et al. Delivery vehicles for small interfering RNA in vivo. Hum Gene Ther. Feb. 2008;19(2):125-32.

Drucker, et al. Enhancing incretin action for the treatment of type 2 diabetes. Diabetes Care. Oct. 2003;26(10):2929-40.

Eckstein, F. Small non-coding RNAs as magic bullets. Trends Biochem Sci. Aug. 2005;30(8):445-52.

Erbacher, et al. The reduction of the positive charges of polylysine by partial gluconoylation increases the transfection efficiency of polylysine/DNA complexes. Biochim Biophys Acta. 1997; 1324(1):27-36.

Eto, et al. Regulation of insulin gene transcription by the immediate-early growth response gene Egr-1. Endocrinology. Jun. 2006;147(6):2923-35.

Ettaro, et al. Cost-of-illness studies in diabetes mellitus. Pharmacoeconomics. 2004;22(3):149-64.

Farilla, et al. Glucagon-like peptide 1 inhibits cell apoptosis and improves glucose responsiveness of freshly isolated human islets. Endocrinology. Dec. 2003;144(12):5149-58.

Feng, et al. Tissue distribution and plasma clearance of heparin-binding EGF-like growth factor (HB-EGF) in adult and newborn rats. Peptides. 2005.

Filipowicz, W. RNAi: the nuts and bolts of the RISC machine. Cell. Jul. 15, 2005;122(1):17-20.

Gappa, et al. The effect of zinc-crystallized glucagon-like peptide-1 on insulin secretion of macroencapsulated pancreatic islets. Tissue Eng. Feb. 2001;7(1):35-44.

Giammona, et al. Coupling of the antiviral agent zidovudine to polyaspartamide and in vitro drug release studies. J Control Release. Aug. 14, 1998;54(3):321-31.

Greene, et al. Protection for the amino group. In Protective Groups in Organic Synthesis. Wiley, John, & Sons. 2nd ed. New York, 1991; 309-405.

Grmec, et al. Vasopressin improves outcome in out-of-hospital cardiopulmonary resuscitation of ventricular fibrillation and pulseless ventricular tachycardia: a observational cohort study. Crit Care. Feb. 2006;10(1):R13 (7 pages).

Gupta, et al. Inflammation: imaging with methoxy poly(ethylene glycol)-poly-L-lysine-DTPA, a long-circulating graft copolymer. Radiology. Dec. 1995;197(3):665-9.

Hakanson, et al. Evidence that gastrin enhances 45Ca uptake into bone through release of a gastric hormone. Regul Pept. 1990; 28(1):107-118.

Halter, et al Effect of acid inhibition on the growth of parital cells. Scand J Gastroenterol Suppl. 1986; 125:9-13.

Hansen, et al. Pharmcokinetics and organ metabolism of carboxyamidated and glycine-extended gastrins in pigs. Am J Physiol. 1996; 271:G156-163.

Heidel, et al. Administration in non-human primates of escalating intravenous doses of targeted nanoparticles containing ribonucleotide reductase subunit M2 siRNA. Proc Natl Acad Sci U S A. Apr. 3, 2007;104(14):5715-21.

Hrkach, et al. Synthesis of Poly(L-lactic acid-L-lycine) Graft Copolymers. Macromolecules. 1995; 4736-4739.

Hudecz, et al. Influence of carrier on biodistribution and in vitro cytotoxicity of methotrexate-branched polypeptide conjugates. Bioconjug Chem. 1993; 4(1):25-33.

Hui, et al. Glucagon-Like Peptide 1 Induces Differentiation of Islet Duodenal Homeobox-1-Positive Pancreatic Ductal Cells Into Insulin-Secreting Cells. Diabetes. 2001; 785-796.

Huotari, et al. Growth factor-mediated proliferation and differentiation of insulin-producing INS-1and PINm5F cells: identification of betacellulin as a novel beta-cellmitogen. Endocrinology. 1998; 139(4):1494-1499.

Im, et al. Irreversible inactiviation of rat gastric (H+-K+)-ATPase in vivo by omeprazole. Biochem Biophys Res Commun. 1985; 126(1): 78-82.

International search report dated Jan. 6, 2009 for PCT Application No. US2008/72148.

International search report dated Feb. 26, 2009 for PCT Application No. US2008/83687.

Keeling, et al. Studies on the mechanism of action of omeprazole. Biochem Pharmacol. 1985; 34(16):2967-2973.

Kim, et al. PEG conjugated VEGF siRNA for anti-angiogenic gene therapy. J Control Release. Nov. 28, 2006;116(2):123-9.

Klinkenberg-Knol, E. The role of omeprazole in healing and prevention of reflux disease. Hepatogastroenterology. 1992; 39:27-30.

Kollen, et al. Gluconoylated and glycosylated polylysines as vectors for gene transfer into cystic fibrosis airway epithelial cells. Hum Gene Ther. 1996; 7(13):1577-86.

Koop, et al. Serum Gastrin levels during long-term omeprazole treatment. Aliment Pharmacol Ther. 1990; 4(2):131-138.

Kubo, et al. Chemically modified symmetric and asymmetric duplex RNAs: an enhanced stability to nuclease degradation and gene silencing effect. Biochem Biophys Res Commun. Jan. 4, 2008;365(1):54-61.

Lamberts, et al. Long-term omeprazole treatment in man: effects on gastric endocrine cell populations. Digestion. 1988; 39(2): 126-135.

Lapidot, et al. Use of esters of N-hydroxysuccinimide in the synthesis of N-acylamino acids. J Lipid Res. Mar. 1967;8(2):142-5.

Larson, et al. Omeprazole-induced hypergastrinemia: role of gastric acidity. J Surg Res. 1986; 40(5):504-509.

Larson, et al. Relationship of omeprazole-induced hypergastrinemia to gastric pH. Surgery. 1986; 100(2):175-180.

Leonard, et al. Trimethylene Bridges as Synthetic Spacers for the Detection of Intramolecular Interactions. Americal Chemical Society. 1979; 423-429.

Lev-Ran, et al. Origin of urinary epidermal growth factor in humans: excretion of endogenous EGF and infused [131I1]-human EGF and kidney histochemistry. Clin Exp Pharmacol Physiol. 1992; 19(10):667-673.

March. Quantitative Treatments of the Effect of Structure on Reactivity. Advanced Organic Chemistry. MeGraw Hill Book Company. New York, 1977; 251-259.

Nielsen, et al. Pharmacology of exenatide (synthetic exendin-4) for the treatment of type 2 diabetes. Curr Opin Investig Drugs. Apr. 2003;4(4):401-5.

Nimesh, et al. Novel polyallylamine-dextran sulfate-DNA nanoplexes: highly efficient non-viral vector for gene delivery. Int J Pharm. Aug. 31, 2006;320(1-2):143-9.

O'Brien, et al. Terlipressin for norepinephrine-resistant septic shock. Lancet. 2002; 359(9313):1209-10. (abstract only).

Office action dated Dec. 15, 2009 for U.S. Appl. No. 11/613,183.

Office action dated Jul. 20, 2009 for U.S. Appl. No. 11/428,803.

Office action dated Jul. 26, 2010 for U.S. Appl. No. 12/194,144.

Oliveira, et al. Targeted Delivery of siRNA. J Biomed Biotechnol. 2006;1-9.

Otto, et al. Recognition and separation of isoenzymes by metal chelates: Immobilized metal ion affinity partitioning of lactate dehydrogenase isoenzymes. Journal of Chromatography. 1993; 644: 25-33.

Paramonov, et al. Self-assembly of peptide-amphiphile nanofibers: the roles of hydrogen bonding and amphiphilic packing. J Am Chem Soc. Jun. 7, 2006;128(22):7291-8.

Patel, et al. Cell penetrating peptides: intracellular pathways and pharmaceutical perspectives. Pharm Res. Nov. 2007;24(11):1977-92.

Perry, et al. The glucagon-like peptides: a double-edged therapeutic sword? Trends Pharmacol Sci. Jul. 2003;24(7):377-83.

PharmaIn—Enabling and improving human therapeutics. PharmaIn Intruduction. Oct. 2009. Available at http://www.pharmain.com/PDF/PharmaIN%20BD%20Presentation%20Slides_16OCTO9.pdf. Accessed Mar. 24, 2010.

Porath, et al. Metal chelate affinity chromatography, a new approach to protein fractionation. Nature. Dec. 18, 1975;258(5536):598-9.

Prosser, et al. Novel chelate-induced magnetic alignment of biological membranes. Biophys J. Nov. 1998;75(5):2163-9.

Rostin, et al. B-Domain deleted recombinant coagulation factor VIII modified with monomethoxy polyethylene glycol. Bioconjug Chem. May-Jun. 2000;11(3):387-96.

Schentag, et al. Pharmacokinetics and pharmacodynamics of acid-suppressive agents in patents with gastroesophageal reflux disease. Am J Hosp Pharm. 1993; 50: S7-10.

Schiffelers, et al. Cancer siRNA therapy by tumor selective delivery with ligand-targeted sterically stabilized nanoparticle. Nucleic Acids Res. Nov. 1, 2004;32(19):e149.

Scrocchi, et al. Identification of glucagon-like peptide 1 (GLP-1) actions essential for glucose homeostasis in mice with disruption of GLP-1 receptor signaling. Diabetes. Apr. 1998;47(4):632-9.

Senekowitsch-Schmidtke, et al. In vivo evaluation of epidermal growth factor (EGF) receptor density on human tumor xenografts using radiolabeled EGF and anti-(EGF receptor) mAb 425. Cancer Immunol Immunother. 1996; 42(2): 108-114.

Shapiro, et al. Clinical islet transplant: current and future directions towards tolerance. Immunol Rev. Dec. 2003;196:219-36.

Simeoni, et al. Insight into the mechanism of the peptide-based gene delivery system MPG: implications for delivery of siRNA into mammalian cells. Nucleic Acids Res. Jun. 1, 2003;31(11):2717-24.

Song, et al. Expansion of Pdx1-expressing pancreatic epithelium and islet neogenesis in transgenix mice overexpression transforming growth factor alpha. Gastroenterology. 1999; 117(6):1416-1426.

Sontheimer, et al. Silence from within: endogenous siRNAs and miRNAs. Cell. Jul. 15, 2005;122(1):9-12.

Sparado, et al. A convenient manual trinitrobenzenesulfonic acid method for monitoring amino acids and peptides in chromatographic column effluents. Anal Biochem. 1979; 96:317-321.

Suarez-Pinzon, et al. Combination therapy with epidermal growth factors and gastrin increses beta-cells mass and reverses hyperglycemia in diabetic NOD mice. Diabetes. 2005; 54(9):2596-2601.

Suginoshita, et al. Liver targeting of human interferon-beta with pullulan based on metal coordination. J Control Release. Sep. 18, 2002;83(1):75-88.

Suginoshita, et al. Liver targeting of interferon-beta with a liver-affinity polysaccharide based on metal coordination in mice. J Pharmacol Exp Ther. Aug. 2001;298(2):805-11.

Tabata, et al. Growth factor release from amylopectin hydrogel based on copper coordination. J Control Release. Dec. 4, 1998;56(1-3):135-48.

Tabata, et al. Targeting of tumor necrosis factor to tumor by use of dextran and metal coordination. J Control Release. May 20, 1999;59(2):187-96.

Terpe, K. Overview of tag protein fusions: from molecular and biochemical fundamentals to commercial systems. Appl Microbiol Biotechnol. Jan. 2003;60(5):523-33.

Tourrel, et al: Glucagon-like peptide-1 and exendin-4 stimulate beta-cell neogenesis in streptozotocin-treated newborn rats resulting in persistently improved glucose homeostasis at adult age. Diabetes. Jul. 2001;50(7):1562-70.

Urusova, et al. GLP-1 inhibition of pancreatic islet cell apoptosis. Trends Endocrinol Metab. Jan.-Feb. 2004;15(1):27-33.

Van Broekhoven, et al. A novel system for convenient detection of low-affinity receptor-ligand interactions: chelator-lipid liposomes engrafted with recombinant CD4 bind to cells expressing MHC class II. Immunol Cell Biol. Jun. 2001;79(3):274-84.

Van Nieuwenhove, et al. Gastrin stimulates epithelial cell proliferation in the oesophagus of rats. Virchows Arch. 1998; 432(4): 371-375.

Wagner. Delivery of drugs, protein and genes into cells using transferrin as a ligand for receptor-mediated endocytosis. Advanced drug delivery reviews. 1994; 14: 113-135.

Weast, R. Periodic Table of Elements. Handbook of Chemistry and Physics. CAS Version. 67th Ed. Boca Raton, FL. CRC Press. 1986-1987; inside cover.

Wenzel, et al. A Comparison of Vasopressin and Epinephrine for Out-of-Hospital Cardiopulmonary Resuscitation. N. Engl J Med 2004;350:105-113.

Wiedeman, et al. Dipeptidyl peptidase IV inhibitors for the treatment of impaired glucose tolerance and type 2 diabetes. Curr Opin Investig Drugs. Apr. 2003;4(4):412-20.

Wolfrum, et al. Mechanisms and optimization of in vivo delivery of lipophilic siRNAs. Nat Biotechnol. Oct. 2007;25(10):1149-57.

Xu, et al. Exendin-4 stimulates both beta-cell replication and neogenesis, resulting in increased beta-cell mass and improved glucose tolerance in diabetic rats. Diabetes. Dec. 1999;48(12):2270-6.

Yamamoto, et al. Recombinant human betacellulin promotes the neogenesis of beta-cells and ameliorates glucos intolerance in mice with diabetes induced by selective alloxan perfusion. Diabetes. 2000; 49(12):2021-2027.

Yu, et al. Pharmacokinetic and pharmacodynamic evaluation of a novel proton pump inhibitor, YH1885, in healthy volunteer. J Clin Pharmacol. 2004; 44(1):73-82.

Zhou, et al. DNA transfection mediated by cationic liposomes containing lipopolylysine: characterization and mechanism of action. Biochim Biophys Acta. 1994; 1189(2):195-203.

Zhou, et al. Lipophilic polylysines mediate efficient DNA transfection in mammalian cells. Biochim Biophys Acta. 1991; 1065(1):8-14.

Office action dated Feb. 3, 2012 for U.S. Appl. No. 12/194,144.
Office action dated Feb. 14, 2011 for U.S. Appl. No. 12/184,186.
Office action dated Mar. 11, 2011 for U.S. Appl. No. 12/271,732.
Office action dated Apr. 8, 2010 for U.S. Appl. No. 12/271,732.
Office action dated Aug. 10, 2012 for U.S. Appl. No. 12/194,144.
Office action dated Oct. 8, 2010 for U.S. Appl. No. 12/184,186.
Office action dated Nov. 15, 2010 for U.S. Appl. No. 12/271,732.
Office action dated Dec. 15, 2009 for U.S. Appl. No. 12/194,144.

* cited by examiner

Lysine Vasopressin analog with C12 amide

Lysine Vasopressin Analog with C12 ester linked through lactate

Lysine Vasopressin analog with C8 amide

Lysine Vasopressin analog with C8 ester linked through lactate

*Enzyme cleavage site to convert to lysine vasopressin*

FIG. 5

Lysine Vasopressin analog with three histidine residues

Lysine Vasopressin analog with six histidine residues

Arginine Vasopressin analog with 6 histidine residues

*Enzyme cleavage site to convert to arginine vasopressin*

Schematic cross-section of micelle formed from vasopressin analogs containing fatty acids

Vasopressin analog with nitrilotriacetic acid

Peptide analog with nitrilotriacetic acid

Nitrilotriacetic acid derivative [N',N',bis(carboxymethyl)-lysine] attached to carboxyl terminus of a peptide

Peptide analog with iminodiacetic acid

*Iminodiacetic acid (or diglycine) attached to carboxyl terminus of a peptide*

Peptide analog with nitrilotriacetic acid

*nitrilotriacetic acid attached to amino terminus of a peptide*

SEQUENCE LISTING

```
<160> NUMBER OF SEQ ID NOS: 78

<210> SEQ ID NO 1
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(6)
<223> OTHER INFORMATION: This region may encompass 2-6 'His' residues
      or is not present
<220> FEATURE:
<221> NAME/KEY: misc_feature
<222> LOCATION: (1)..(6)
<223> OTHER INFORMATION: If 'His' residues are not present, region may
      encompass a chemical group or moiety containing an alkyl group
      with 3-36 carbon units, NTA or IDA
<220> FEATURE:
<221> NAME/KEY: MOD_RES
<222> LOCATION: (17)..(17)
<223> OTHER INFORMATION: Lys or Arg
<220> FEATURE:
<221> NAME/KEY: MOD_RES
<222> LOCATION: (18)..(18)
<223> OTHER INFORMATION: Gly or Ala
<220> FEATURE:
<223> OTHER INFORMATION: C-term may end -NH2 or -H

<400> SEQUENCE: 1

His His His His His His Gly Gly Gly Cys Tyr Phe Gln Asn Cys Pro
1               5                   10                  15

Xaa Xaa

<210> SEQ ID NO 2
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

His Ala Glu Gly Thr Phe Thr Ser Asp Val Ser Ser Tyr Leu Glu Gly
1               5                   10                  15
```

Gln Ala Ala Lys Glu Phe Ile Ala Trp Leu Val Lys Gly Arg
            20                  25                  30

<210> SEQ ID NO 3
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 4
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Gly
            20                  25                  30

<210> SEQ ID NO 5
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Gly
            20                  25                  30

Gly

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

His His His His His His Gly Gly Gly
1               5

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 7

Ile His Pro Phe His Leu Val Ile His Thr
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu Ala Gln Ala Val Arg Ser Ser Ser Arg
1               5                   10

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Norleucine

<400> SEQUENCE: 9

Glu Arg Leu Phe Leu Ser Phe Pro
1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Gln Asn Tyr Pro Ile Val Gln
1               5

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Gly Val Val Asn Ala Ser Ser Arg Leu Ala
1               5                   10

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Glu Val Asn Leu Asp Ala Phe Lys
1               5
```

```
<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Glu Val Asn Leu Asp Ala Glu Phe Lys
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Glu Val Lys Val Asp Ala Glu Phe Lys
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

His Gln Lys Leu Val Phe Phe Ala Lys
1               5

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Lys Thr Glu Glu Ile Ser Glu Val Asn Leu Asp Ala Glu Phe
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Glu Val His His Gln Lys Leu Val Phe Phe Ala Glu
1               5                   10

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18
```

```
Pro Gln Gly Leu Glu
1               5

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Norvaline

<400> SEQUENCE: 19

Arg Pro Lys Pro Val Glu Val Trp Arg Lys
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Norvaline

<400> SEQUENCE: 20

Arg Pro Lys Pro Tyr Ala Val Trp Met Lys
1               5                   10

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Pro Leu Ala Tyr Trp Ala Arg
1               5

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Pro Leu Ala Leu Trp Arg Ser
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Norvaline
```

```
<400> SEQUENCE: 23

Arg Pro Lys Pro Leu Ala Val Trp Lys
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Pro Tyr Ala Tyr Trp Met Arg
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Pro Leu Gly Met Trp Ser Arg
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Pro Leu Ala Leu Trp Ala Arg
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: D-Arg

<400> SEQUENCE: 27

Pro Leu Gly Leu Trp Ala Arg
1               5

<210> SEQ ID NO 28
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Asp Glu Val Asp
1
```

```
<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Asp Met Gln Asp
1

<210> SEQ ID NO 30
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Leu Glu Val Asp
1

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Val Glu Ile Asp
1

<210> SEQ ID NO 32
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ile Glu Thr Asp
1

<210> SEQ ID NO 33
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Leu Glu His Asp
1

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

<223> OTHER INFORMATION: CH3(CH2)10CO-Gly
<220> FEATURE:
<223> OTHER INFORMATION: C-term amidated

<400> SEQUENCE: 34

Gly Gly Gly Cys Tyr Phe Gln Asn Cys Pro Lys Gly
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: CH3(CH2)10CO-OHC(CH3)CO-Gly
<220> FEATURE:
<223> OTHER INFORMATION: C-term amidated

<400> SEQUENCE: 35

Gly Gly Gly Cys Tyr Phe Gln Asn Cys Pro Lys Gly
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: CH3(CH2)6CO-Gly
<220> FEATURE:
<223> OTHER INFORMATION: C-term amidated

<400> SEQUENCE: 36

Gly Gly Gly Cys Tyr Phe Gln Asn Cys Pro Lys Gly
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: CH3(CH2)6CO-OHC(CH3)CO-Gly
<220> FEATURE:
<223> OTHER INFORMATION: C-term amidated

<400> SEQUENCE: 37

Gly Gly Gly Cys Tyr Phe Gln Asn Cys Pro Lys Gly
1               5                   10

<210> SEQ ID NO 38
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

```
<400> SEQUENCE: 38

His His His His His His Gly Gly Gly Cys Tyr Phe Gln Asn Cys Pro
1               5                   10                  15

Lys Gly

<210> SEQ ID NO 39
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 39

His His His Gly Gly Gly Cys Tyr Phe Gln Asn Cys Pro Lys Gly
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 40

His His His Gly Gly Gly Cys Tyr Phe Gln Asn Cys Pro Arg Gly
1               5                   10                  15

<210> SEQ ID NO 41
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 41

His His His His His His Gly Gly Gly Cys Tyr Phe Gln Asn Cys Pro
1               5                   10                  15

Arg Gly

<210> SEQ ID NO 42
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (30)..(30)
<223> OTHER INFORMATION: Arg-IDA

<400> SEQUENCE: 42

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 43
```

```
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(31)
<223> OTHER INFORMATION: Gly-IDA

<400> SEQUENCE: 43

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 44
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (32)..(32)
<223> OTHER INFORMATION: Gly-IDA

<400> SEQUENCE: 44

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Gly
            20                  25                  30

<210> SEQ ID NO 45
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)..(33)
<223> OTHER INFORMATION: Gly-IDA

<400> SEQUENCE: 45

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Gly
            20                  25                  30

Gly

<210> SEQ ID NO 46
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (30)..(30)
<223> OTHER INFORMATION: Arg-NTA

<400> SEQUENCE: 46

His Ala Glu Gly Thr Phe Thr Ser Asp Val Ser Ser Tyr Leu Glu Gly
1               5                   10                  15
```

```
Gln Ala Ala Lys Glu Phe Ile Ala Trp Leu Val Lys Gly Arg
            20                  25                  30

<210> SEQ ID NO 47
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(31)
<223> OTHER INFORMATION: Gly-NTA

<400> SEQUENCE: 47

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 48
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (32)..(32)
<223> OTHER INFORMATION: Gly-NTA

<400> SEQUENCE: 48

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Gly
            20                  25                  30

<210> SEQ ID NO 49
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)..(33)
<223> OTHER INFORMATION: Gly-NTA

<400> SEQUENCE: 49

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Gly
            20                  25                  30

Gly

<210> SEQ ID NO 50
<211> LENGTH: 72
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(6)
```

```
<223> OTHER INFORMATION: Any amino acid except His and this region may
      encompass 0-6 residues
<220> FEATURE:
<221> NAME/KEY: misc_feature
<222> LOCATION: (7)..(12)
<223> OTHER INFORMATION: This region may encompass 1-6 residues
<220> FEATURE:
<221> NAME/KEY: MOD_RES
<222> LOCATION: (13)..(18)
<223> OTHER INFORMATION: Any amino acid except His and this region may
      encompass 0-6 residues or is not present
<220> FEATURE:
<221> NAME/KEY: misc_feature
<222> LOCATION: (19)..(24)
<223> OTHER INFORMATION: This region may encompass 1-6 residues or
      is not present
<220> FEATURE:
<221> NAME/KEY: MOD_RES
<222> LOCATION: (25)..(30)
<223> OTHER INFORMATION: Any amino acid except His and this region may
      encompass 0-6 residues or is not present
<220> FEATURE:
<221> NAME/KEY: misc_feature
<222> LOCATION: (31)..(36)
<223> OTHER INFORMATION: This region may encompass 1-6 residues or
      is not present
<220> FEATURE:
<221> NAME/KEY: MOD_RES
<222> LOCATION: (37)..(42)
<223> OTHER INFORMATION: Any amino acid except His and this region may
      encompass 0-6 residues or is not present
<220> FEATURE:
<221> NAME/KEY: misc_feature
<222> LOCATION: (43)..(48)
<223> OTHER INFORMATION: This region may encompass 1-6 residues or
      is not present
<220> FEATURE:
<221> NAME/KEY: MOD_RES
<222> LOCATION: (49)..(54)
<223> OTHER INFORMATION: Any amino acid except His and this region may
      encompass 0-6 residues or is not present
<220> FEATURE:
<221> NAME/KEY: misc_feature
<222> LOCATION: (55)..(60)
<223> OTHER INFORMATION: This region may encompass 1-6 residues or
      is not present
<220> FEATURE:
<221> NAME/KEY: MOD_RES
<222> LOCATION: (61)..(66)
<223> OTHER INFORMATION: Any amino acid except His and this region may
      encompass 0-6 residues or is not present
<220> FEATURE:
<221> NAME/KEY: misc_feature
<222> LOCATION: (67)..(72)
<223> OTHER INFORMATION: This region may encompass 1-6 residues or
      is not present
<220> FEATURE:
<223> OTHER INFORMATION: See specification as filed for detailed
      description of substitutions and preferred embodiments

<400> SEQUENCE: 50

Xaa Xaa Xaa Xaa Xaa Xaa His His His His His His Xaa Xaa Xaa Xaa
1               5                   10                  15

Xaa Xaa His His His His His His Xaa Xaa Xaa Xaa Xaa Xaa His His
            20                  25                  30

His His His His Xaa Xaa Xaa Xaa Xaa Xaa His His His His His His
        35                  40                  45

Xaa Xaa Xaa Xaa Xaa Xaa His His His His His His Xaa Xaa Xaa Xaa
    50                  55                  60

Xaa Xaa His His His His His His
65                  70

<210> SEQ ID NO 51
<211> LENGTH: 6
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: This sequence may encompass 2-6 residues

<400> SEQUENCE: 51

His His His His His His
1               5

<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 52

His His His His His His
1               5

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Lys or Arg
<220> FEATURE:
<221> NAME/KEY: MOD_RES
<222> LOCATION: (9)..(9)
<223> OTHER INFORMATION: Gly or Ala
<220> FEATURE:
<223> OTHER INFORMATION: C-term may end -NH2 or -H

<400> SEQUENCE: 53

Cys Tyr Phe Gln Asn Cys Pro Xaa Xaa
1               5

<210> SEQ ID NO 54
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(6)
<223> OTHER INFORMATION: This region may encompass 2-6 'His' residues or
      is not present
<220> FEATURE:
<221> NAME/KEY: misc_feature
<222> LOCATION: (1)..(6)
<223> OTHER INFORMATION: If 'His' residues are not present, region may
      encompass a chemical group or moiety containing an alkyl group
      with 8-36 carbon units, NTA or IDA
<220> FEATURE:
<221> NAME/KEY: misc_feature
<222> LOCATION: (7)..(11)
<223> OTHER INFORMATION: This region may encompass 0-5 'Gly' residues
<220> FEATURE:
<221> NAME/KEY: MOD_RES
<222> LOCATION: (12)..(111)
<223> OTHER INFORMATION: Any amino acid and this region may encompass
      5-100 residues
```

-continued

<400> SEQUENCE: 54

His His His His His His Gly Gly Gly Gly Gly Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa
            100                 105                 110

<210> SEQ ID NO 55
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(100)
<223> OTHER INFORMATION: Any amino acid and this region may encompass
      5-100 residues
<220> FEATURE:
<221> NAME/KEY: MOD_RES
<222> LOCATION: (101)..(105)
<223> OTHER INFORMATION: This region may encompass 0-5 'Gly' residues
<220> FEATURE:
<221> NAME/KEY: MOD_RES
<222> LOCATION: (106)..(111)
<223> OTHER INFORMATION: This region may encompass 2-6 'His' residues
      or is not present
<220> FEATURE:
<221> NAME/KEY: misc_feature
<222> LOCATION: (106)..(111)
<223> OTHER INFORMATION: If 'His' residues are not present, region may
      encompass a chemical group or moiety containing an alkyl group
      with 8-36 carbon units, NTA or IDA

<400> SEQUENCE: 55

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Gly Gly Gly Gly Gly His His His His His His
            100                 105                 110

<210> SEQ ID NO 56
<211> LENGTH: 84
<212> TYPE: PRT
<213> ORGANISM: Artificial Sequence

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(6)
<223> OTHER INFORMATION: Any amino acid and this region may encompass
      0-6 residues or is not present
<220> FEATURE:
<221> NAME/KEY: MOD_RES
<222> LOCATION: (7)..(12)
<223> OTHER INFORMATION: This region may encompass 1-6 residues or
      is not present
<220> FEATURE:
<221> NAME/KEY: MOD_RES
<222> LOCATION: (13)..(18)
<223> OTHER INFORMATION: Any amino acid and this region may encompass
      0-6 residues or is not present
<220> FEATURE:
<221> NAME/KEY: MOD_RES
<222> LOCATION: (19)..(24)
<223> OTHER INFORMATION: This region may encompass 1-6 residues or
      is not present
<220> FEATURE:
<221> NAME/KEY: MOD_RES
<222> LOCATION: (25)..(30)
<223> OTHER INFORMATION: Any amino acid and this region may encompass
      0-6 residues or is not present
<220> FEATURE:
<221> NAME/KEY: MOD_RES
<222> LOCATION: (31)..(36)
<223> OTHER INFORMATION: This region may encompass 1-6 residues or
      is not present
<220> FEATURE:
<221> NAME/KEY: MOD_RES
<222> LOCATION: (37)..(42)
<223> OTHER INFORMATION: Any amino acid and this region may encompass
      0-6 residues or is not present
<220> FEATURE:
<221> NAME/KEY: MOD_RES
<222> LOCATION: (43)..(48)
<223> OTHER INFORMATION: This region may encompass 1-6 residues or
      is not present
<220> FEATURE:
<221> NAME/KEY: MOD_RES
<222> LOCATION: (49)..(54)
<223> OTHER INFORMATION: Any amino acid and this region may encompass
      0-6 residues or is not present
<220> FEATURE:
<221> NAME/KEY: MOD_RES
<222> LOCATION: (55)..(60)
<223> OTHER INFORMATION: This region may encompass 1-6 residues or
      is not present
<220> FEATURE:
<221> NAME/KEY: MOD_RES
<222> LOCATION: (61)..(66)
<223> OTHER INFORMATION: Any amino acid and this region may encompass
      0-6 residues or is not present
<220> FEATURE:
<221> NAME/KEY: MOD_RES
<222> LOCATION: (67)..(72)
<223> OTHER INFORMATION: This region may encompass 1-6 residues or
      is not present
<220> FEATURE:
<221> NAME/KEY: misc_feature
<222> LOCATION: (1)..(72)
<223> OTHER INFORMATION: If residues are not present, region may
      encompass a chemical group or moiety containing an alkyl group
      with 3-36 carbon units, NTA or IDA
<220> FEATURE:
<221> NAME/KEY: MOD_RES
<222> LOCATION: (83)..(83)
<223> OTHER INFORMATION: Lys or Arg
<220> FEATURE:
<221> NAME/KEY: MOD_RES
<222> LOCATION: (84)..(84)
<223> OTHER INFORMATION: Gly or Ala
<220> FEATURE:
<223> OTHER INFORMATION: C-term may end -NH2 or -H
<220> FEATURE:
```

<223> OTHER INFORMATION: See specification as filed for detailed
      description of substitutions and preferred embodiments

<400> SEQUENCE: 56

Xaa Xaa Xaa Xaa Xaa Xaa His His His His His His Xaa Xaa Xaa Xaa
1               5                   10                  15

Xaa Xaa His His His His His His Xaa Xaa Xaa Xaa Xaa Xaa His His
            20                  25                  30

His His His His Xaa Xaa Xaa Xaa Xaa Xaa His His His His His His
        35                  40                  45

Xaa Xaa Xaa Xaa Xaa Xaa His His His His His His Xaa Xaa Xaa Xaa
    50                  55                  60

Xaa Xaa His His His His His His Gly Gly Gly Cys Tyr Phe Gln Asn
65                  70                  75                  80

Cys Pro Xaa Xaa

<210> SEQ ID NO 57
<211> LENGTH: 78
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(6)
<223> OTHER INFORMATION: Any amino acid except His and this region may
      encompass 0-6 residues
<220> FEATURE:
<221> NAME/KEY: MOD_RES
<222> LOCATION: (7)..(12)
<223> OTHER INFORMATION: This region may encompass 1-6 residues
<220> FEATURE:
<221> NAME/KEY: MOD_RES
<222> LOCATION: (13)..(18)
<223> OTHER INFORMATION: Any amino acid except His and this region may
      encompass 0-6 residues or is not present
<220> FEATURE:
<221> NAME/KEY: MOD_RES
<222> LOCATION: (19)..(24)
<223> OTHER INFORMATION: This region may encompass 1-6 residues or
      is not present
<220> FEATURE:
<221> NAME/KEY: MOD_RES
<222> LOCATION: (25)..(30)
<223> OTHER INFORMATION: Any amino acid except His and this region may
      encompass 0-6 residues or is not present
<220> FEATURE:
<221> NAME/KEY: MOD_RES
<222> LOCATION: (31)..(36)
<223> OTHER INFORMATION: This region may encompass 1-6 residues or
      is not present
<220> FEATURE:
<221> NAME/KEY: MOD_RES
<222> LOCATION: (37)..(42)
<223> OTHER INFORMATION: Any amino acid except His and this region may
      encompass 0-6 residues or is not present
<220> FEATURE:
<221> NAME/KEY: MOD_RES
<222> LOCATION: (43)..(48)
<223> OTHER INFORMATION: This region may encompass 1-6 residues or
      is not present
<220> FEATURE:
<221> NAME/KEY: MOD_RES
<222> LOCATION: (49)..(54)
<223> OTHER INFORMATION: Any amino acid except His and this region may
      encompass 0-6 residues or is not present
<220> FEATURE:
<221> NAME/KEY: MOD_RES
<222> LOCATION: (55)..(60)
<223> OTHER INFORMATION: This region may encompass 1-6 residues or
      is not present
<220> FEATURE:

```
<221> NAME/KEY: MOD_RES
<222> LOCATION: (61)..(66)
<223> OTHER INFORMATION: Any amino acid except His and this region may
      encompass 0-6 residues or is not present
<220> FEATURE:
<221> NAME/KEY: MOD_RES
<222> LOCATION: (67)..(72)
<223> OTHER INFORMATION: This region may encompass 1-6 residues or
      is not present
<220> FEATURE:
<221> NAME/KEY: misc_feature
<222> LOCATION: (1)..(72)
<223> OTHER INFORMATION: If residues are not present, region may
      encompass a chemical group or moiety containing an alkyl group
      with 6-36 carbon units, NTA or IDA
<220> FEATURE:
<221> NAME/KEY: MOD_RES
<222> LOCATION: (73)..(78)
<223> OTHER INFORMATION: This region may encompass 2-6 residues
<220> FEATURE:
<223> OTHER INFORMATION: See specification as filed for detailed
      description of substitutions and preferred embodiments

<400> SEQUENCE: 57

Xaa Xaa Xaa Xaa Xaa Xaa His His His His His His Xaa Xaa Xaa Xaa
1               5                   10                  15

Xaa Xaa His His His His His Xaa Xaa Xaa Xaa Xaa Xaa His His
            20                  25                  30

His His His His Xaa Xaa Xaa Xaa Xaa Xaa His His His His His His
        35                  40                  45

Xaa Xaa Xaa Xaa Xaa Xaa His His His His His His Xaa Xaa Xaa Xaa
    50                  55                  60

Xaa Xaa His His His His His His Gly Gly Gly Gly Gly Gly
65                  70                  75

<210> SEQ ID NO 58
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: This sequence may encompass 2-6 residues

<400> SEQUENCE: 58

Gly Gly Gly Gly Gly Gly
1               5

<210> SEQ ID NO 59
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: This sequence may encompass 2-6 residues

<400> SEQUENCE: 59

Ala Ala Ala Ala Ala Ala
1               5

<210> SEQ ID NO 60
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: This sequence may encompass 2-6 residues

<400> SEQUENCE: 60

Lys Lys Lys Lys Lys Lys
1               5

<210> SEQ ID NO 61
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: This sequence may encompass 2-6 residues

<400> SEQUENCE: 61

Arg Arg Arg Arg Arg Arg
1               5

<210> SEQ ID NO 62
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: This sequence may encompass 1-3 'Ala-Arg'
      repeating units

<400> SEQUENCE: 62

Ala Arg Ala Arg Ala Arg
1               5

<210> SEQ ID NO 63
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gly Gly Gly Gly
1

<210> SEQ ID NO 64
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gly Gly Gly Gly Gly
1               5

<210> SEQ ID NO 65
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65
```

```
Gly Gly Gly Gly Gly Gly
1               5

<210> SEQ ID NO 66
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ala Ala Ala Ala
1

<210> SEQ ID NO 67
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ala Ala Ala Ala Ala
1               5

<210> SEQ ID NO 68
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ala Ala Ala Ala Ala Ala
1               5

<210> SEQ ID NO 69
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Lys Lys Lys Lys
1

<210> SEQ ID NO 70
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Lys Lys Lys Lys Lys
1               5

<210> SEQ ID NO 71
<211> LENGTH: 6
<212> TYPE: PRT
<213> ORGANISM: Artificial Sequence
<220> FEATURE:
<223> OTHER INFORMATION: Description of Artificial Sequence: Synthetic
```

-continued

```
      peptide

<400> SEQUENCE: 71

Lys Lys Lys Lys Lys Lys
1               5

<210> SEQ ID NO 72
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Arg Arg Arg Arg
1

<210> SEQ ID NO 73
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Arg Arg Arg Arg Arg
1               5

<210> SEQ ID NO 74
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Arg Arg Arg Arg Arg Arg
1               5

<210> SEQ ID NO 75
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

His Ala Glu Gly Thr Phe Thr Ser
1               5

<210> SEQ ID NO 76
<211> LENGTH: 184
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(6)
<223> OTHER INFORMATION: Any amino acid except His and this region may
      encompass 0-6 residues or is not present
<220> FEATURE:
<221> NAME/KEY: MOD_RES
<222> LOCATION: (7)..(12)
<223> OTHER INFORMATION: This region may encompass 1-6 residues or
```

```
      is not present
<220> FEATURE:
<221> NAME/KEY: MOD_RES
<222> LOCATION: (13)..(18)
<223> OTHER INFORMATION: Any amino acid except His and this region may
      encompass 0-6 residues or is not present
<220> FEATURE:
<221> NAME/KEY: MOD_RES
<222> LOCATION: (19)..(24)
<223> OTHER INFORMATION: This region may encompass 1-6 residues or
      is not present
<220> FEATURE:
<221> NAME/KEY: MOD_RES
<222> LOCATION: (25)..(30)
<223> OTHER INFORMATION: Any amino acid except His and this region may
      encompass 0-6 residues or is not present
<220> FEATURE:
<221> NAME/KEY: MOD_RES
<222> LOCATION: (31)..(36)
<223> OTHER INFORMATION: This region may encompass 1-6 residues or
      is not present
<220> FEATURE:
<221> NAME/KEY: MOD_RES
<222> LOCATION: (37)..(42)
<223> OTHER INFORMATION: Any amino acid except His and this region may
      encompass 0-6 residues or is not present
<220> FEATURE:
<221> NAME/KEY: MOD_RES
<222> LOCATION: (43)..(48)
<223> OTHER INFORMATION: This region may encompass 1-6 residues or
      is not present
<220> FEATURE:
<221> NAME/KEY: MOD_RES
<222> LOCATION: (49)..(54)
<223> OTHER INFORMATION: Any amino acid except His and this region may
      encompass 0-6 residues or is not present
<220> FEATURE:
<221> NAME/KEY: MOD_RES
<222> LOCATION: (55)..(60)
<223> OTHER INFORMATION: This region may encompass 1-6 residues or
      is not present
<220> FEATURE:
<221> NAME/KEY: MOD_RES
<222> LOCATION: (61)..(66)
<223> OTHER INFORMATION: Any amino acid except His and this region may
      encompass 0-6 residues or is not present
<220> FEATURE:
<221> NAME/KEY: MOD_RES
<222> LOCATION: (67)..(72)
<223> OTHER INFORMATION: This region may encompass 1-6 residues or
      is not present
<220> FEATURE:
<221> NAME/KEY: MOD_RES
<222> LOCATION: (73)..(84)
<223> OTHER INFORMATION: This region may encompass 0-6 Gly residues,
      0-6 Ala residues, 0-6 Arg residues, 0-6 Lys residues, 0-6
      'Xaa-Arg' repeating units or 0-6 'Xaa-Lys' repeating
      units wherein 'Xaa' is any amino acid
<220> FEATURE:
<221> NAME/KEY: MOD_RES
<222> LOCATION: (85)..(184)
<223> OTHER INFORMATION: Any amino acid and this region may encompass
      5-100 residues
<220> FEATURE:
<223> OTHER INFORMATION: See specification as filed for detailed
      description of substitutions and preferred embodiments

<400> SEQUENCE: 76

Xaa Xaa Xaa Xaa Xaa Xaa His His His His His His Xaa Xaa Xaa Xaa
1               5                   10                  15

Xaa Xaa His His His His His His Xaa Xaa Xaa Xaa Xaa Xaa His His
            20                  25                  30

His His His His Xaa Xaa Xaa Xaa Xaa Xaa His His His His His His
        35                  40                  45

Xaa Xaa Xaa Xaa Xaa Xaa His His His His His Xaa Xaa Xaa Xaa
    50                  55                  60
```

```
Xaa Xaa His His His His His His Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa Xaa
             85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa
            180

<210> SEQ ID NO 77
<211> LENGTH: 184
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(100)
<223> OTHER INFORMATION: Any amino acid and this region may encompass
      5-100 residues
<220> FEATURE:
<221> NAME/KEY: MOD_RES
<222> LOCATION: (101)..(112)
<223> OTHER INFORMATION: This region may encompass 0-6 Gly residues,
      0-6 Ala residues, 0-6 Arg residues, 0-6 Lys residues, 0-6
      'Xaa-Arg' repeating units or 0-6 'Xaa-Lys' repeating
      units wherein 'Xaa' is any amino acid
<220> FEATURE:
<221> NAME/KEY: MOD_RES
<222> LOCATION: (113)..(118)
<223> OTHER INFORMATION: Any amino acid except His and this region may
      encompass 0-6 residues or is not present
<220> FEATURE:
<221> NAME/KEY: MOD_RES
<222> LOCATION: (119)..(124)
<223> OTHER INFORMATION: This region may encompass 1-6 residues or
      is not present
<220> FEATURE:
<221> NAME/KEY: MOD_RES
<222> LOCATION: (125)..(130)
<223> OTHER INFORMATION: Any amino acid except His and this region may
      encompass 0-6 residues or is not present
<220> FEATURE:
<221> NAME/KEY: MOD_RES
<222> LOCATION: (131)..(136)
<223> OTHER INFORMATION: This region may encompass 1-6 residues or
      is not present
<220> FEATURE:
<221> NAME/KEY: MOD_RES
<222> LOCATION: (137)..(142)
<223> OTHER INFORMATION: Any amino acid except His and this region may
      encompass 0-6 residues or is not present
<220> FEATURE:
<221> NAME/KEY: MOD_RES
<222> LOCATION: (143)..(148)
<223> OTHER INFORMATION: This region may encompass 1-6 residues or
      is not present
<220> FEATURE:
<221> NAME/KEY: MOD_RES
<222> LOCATION: (149)..(154)
<223> OTHER INFORMATION: Any amino acid except His and this region may
      encompass 0-6 residues or is not present
```

```
<220> FEATURE:
<221> NAME/KEY: MOD_RES
<222> LOCATION: (155)..(160)
<223> OTHER INFORMATION: This region may encompass 1-6 residues or
      is not present
<220> FEATURE:
<221> NAME/KEY: MOD_RES
<222> LOCATION: (161)..(166)
<223> OTHER INFORMATION: Any amino acid except His and this region may
      encompass 0-6 residues or is not present
<220> FEATURE:
<221> NAME/KEY: MOD_RES
<222> LOCATION: (167)..(172)
<223> OTHER INFORMATION: This region may encompass 1-6 residues or
      is not present
<220> FEATURE:
<221> NAME/KEY: MOD_RES
<222> LOCATION: (173)..(178)
<223> OTHER INFORMATION: Any amino acid except His and this region may
      encompass 0-6 residues or is not present
<220> FEATURE:
<221> NAME/KEY: MOD_RES
<222> LOCATION: (179)..(184)
<223> OTHER INFORMATION: This region may encompass 1-6 residues or
      is not present
<220> FEATURE:
<223> OTHER INFORMATION: See specification as filed for detailed
      description of substitutions and preferred embodiments

<400> SEQUENCE: 77

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa His His His His His His Xaa Xaa Xaa Xaa
        115                 120                 125

Xaa Xaa His His His His His His Xaa Xaa Xaa Xaa Xaa Xaa His His
    130                 135                 140

His His His His Xaa Xaa Xaa Xaa Xaa Xaa His His His His His His
145                 150                 155                 160

Xaa Xaa Xaa Xaa Xaa Xaa His His His His His His Xaa Xaa Xaa Xaa
                165                 170                 175

Xaa Xaa His His His His His His
            180

<210> SEQ ID NO 78
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Amide group-Gly
<220> FEATURE:
```

-continued

```
<221> NAME/KEY: MOD_RES
<222> LOCATION: (11)..(11)
<223> OTHER INFORMATION: Lys or Arg
<220> FEATURE:
<221> NAME/KEY: MOD_RES
<222> LOCATION: (12)..(12)
<223> OTHER INFORMATION: Gly or Ala
<220> FEATURE:
<223> OTHER INFORMATION: C-term may end -NH2 or -H

<400> SEQUENCE: 78

Gly Gly Gly Cys Tyr Phe Gln Asn Cys Pro Xaa Xaa
1               5                   10
```

COMPOSITION FOR LONG-ACTING PEPTIDE ANALOGS

CROSS-REFERENCE

This application claims priority as a continuation under 35 U.S.C. §120 of U.S. patent application Ser. No. 12/184,186, filed Jul. 31, 2008, which claims priority under 35 U.S.C. §119(e) of U.S. Provisional Application No. 60/953,789, filed Aug. 3, 2007. The contents of both are incorporated herein by reference in their entirety.

STATEMENT AS TO FEDERALLY SPONSORED RESEARCH

This invention was made in part with government support under 5 R43 DK069727 awarded by the National Institute of Diabetes and Digestive and Kidney Diseases (NIDDK). The U.S. Government may have certain rights in subject matter provided herein.

SEQUENCE LISTING

The instant application contains a Sequence Listing which has been submitted in ASCII format via EFS-Web and is hereby incorporated by reference in its entirety. Said ASCII copy, created on Apr. 22, 2011, is named 35227731.txt and is 39,926 bytes in size.

BACKGROUND OF THE INVENTION

The development of new formulations and delivery systems for administration of physiologically active peptides and proteins and other therapeutics and materials is driven by the need to provide these peptides or proteins or other materials to achieve the desirable physiological effects. With respect to peptides and proteins, many of them must be delivered via systemic circulation. In addition, peptides and proteins that have low molecular masses tend to have short biological half-lives due to their efficient removal from systemic circulation via kidneys. For example, a fraction of these peptides and proteins can also be removed via reticulo-endothelial uptake due to recognition by monocyte/macrophages or as a result of opsonization by complement components. Many peptides and proteins can also lose their activity in vivo due to proteolysis (peptide bond cleavage).

In part to circumvent these undesirable effects, a drug delivery system may be used. There are several drug delivery strategies that can be useful for peptide and protein delivery in vivo. First, a continuous systemic infusion of drug via a pump can be employed. This strategy is proven efficient in clinical practice but may be impractical for outpatients requiring high levels of mobility, associated disadvantages of quality of life and potential intravenous (I.V.) line infections. Thus, there is a need for improved compositions and formulations for the administration of peptides that have a prolonged half-life to reduce the need for frequent and repeated administrations or infusions.

Cirrhosis of the liver is a common consequence of excessive alcohol consumption or hepatitis leading to life-threatening complications. In patients with cirrhosis and type 1 hepatorenal syndrome (HRS), splanchnic vasodilation resulting from portal vein hypertension plays a critical role in the progression to renal failure. The use of splanchnic and systemic vasoconstrictors such as vasopressin agonists or alpha-1-adrenergic receptor agonists can improve renal function in patients with type 1 HRS. Studies also suggest that vasoconstrictor administration is a promising therapeutic approach targeting vasodilation involved in, but not limited to (1) renal failure in type 2 HRS; (2) esophageal varices; (3) paracentesis-induced circulatory dysfunction; (4) arterial hypotension induced by byproducts of bacteria, (5) anesthesia-associated hypotension, (6) cardiac arrest, and (7) post-partum hemorrhage. Under these conditions a long acting vasoconstrictor such as long-acting vasopressin will be beneficial for these patients.

HRS is characterized by renal failure in patients with advanced cirrhosis and liver failure, and severe sinusoidal portal hypertension. There are two types of HRS, type 1 and type 2. Type 1 is characterized by rapid deterioration of renal function with doubling of serum creatinine to greater than 2.5 mg/dL (221 uM) in less than 2 weeks with median survival of 1.7 weeks. Type 2 is characterized by stable or slowly progressive renal dysfunction with median survival of 6 months. The probability of developing HRS in cirrhosis patients with ascites is 19% at 1 year and increases to 39% at 5 years.

Esophageal Variceal Hemorrhage (EVH) is a complication of portal hypertension resulting from cirrhosis. EVH accounts for 6-12% of upper GI bleeds (Longstreth G F, et al. Am J Gastroenterol 1995; 90(2):206-210; Wilcox C M, et al. Southern Medical Journal 1999; 92(1):44-50; Sorbi D, et al. Am J Gastroenterol 2003; 98(11):2424-2434). The treatment of EVH according to ACG Guidelines (1997) is endoscopic treatment (ligation or sclerotherapy) in combination with vasoactive therapeutics; e.g., vasopressin or its analogs.

SUMMARY OF THE INVENTION

The present disclosure provides compositions of complexes containing biologically active peptides, formulations and methods of use of such compositions. In part, the present invention is directed to peptide complexes for administration to a patient that are configured to deliver and prolong the half-life of biologically-active peptides and proteins in vivo.

One embodiment of the invention relates to a group of novel long-acting vasopressin analogs, their formulation and methods of treatment using these compounds to increase perfusion to various organs in hypovolemic and hypotensive situation and increase the level of factor VIII and plasminogen activator in the blood. More particularly, the invention is concerned with vasopressin and biologically-active polypeptide derivatives of vasopressin which have been modified by covalent binding of binding moieties to produce long acting analogs of the polypeptides that are believed to function by slow release of an active vasopressin or vasopressin derivative. Furthermore, the modifications in the vasopressin analogs of the present invention allow the analogs to be loaded into a hydrophobic containing carrier polymer for slow release of the analogs into the blood and their activation into vasopressin. In another aspect of the invention the vasopressin analogs contain sufficient hydrophobic chains to form micelle allowing for even slower activation and longer-sustained release or half-life. The disclosure also provides modifications of the analogs of the present invention that can be loaded into metal chelate containing polymeric carriers for slow release of the analogs into the blood and, if needed, allows for their activation after release.

Another embodiment of the invention relates peptides with chelating groups or alkyl groups, such as fatty acids, attached to carboxyl or amino terminal of peptides, their formulation and methods of treatment using these peptides. In one particular example, the invention is concerned with analogs of GLP-1(7-36) and GLP-1(7-37) where the carboxyl terminal is modified with nitrilotriacetic acid or imidodiacetic acid that will allow GLP-1 to be anchored non-covalently to a carrier containing metal ion, preferably Zn or Cu. Furthermore, the GLP-1 analogs of the present invention allow the analogs to be loaded into a hydrophobic- and metal ion-containing polymer for slow release into the blood. The long acting GLP analogs are especially useful for the treatment of diabetes and cardiovascular disease. Furthermore, modifications of the peptides at amino or carboxyl terminals by attaching nitrilotriacetic acid or imidodiacetic acid allow the resulting peptide analogs of the present invention to be loaded into metal chelate containing polymeric carriers for slow release of the analogs into the blood and, if needed, allows for their activation by proteases after release.

Vasopressin agonists are used therapeutically to induce splanchnic and systemic vasoconstriction, thereby restoring hemodynamic balance and increasing organ perfusion. However the use of vasopressin is limited due to its short 24 minute half-life and its need to be administered by infusion or repeated and frequent injections. Longer-acting synthetic vasopressin analogs are useful in conditions featuring low vasopressin secretion, as well as for control of bleeding (in some forms of von Willebrand disease), extreme cases of bedwetting by children and esophageal varices (Barett et al., *Gastroenterology* 1970; 58:926). Ideally, a very long acting vasopressin agonist administered once a day will be useful in the prolonging the survival of patients waiting for liver transplantation compared to continuous infusion or twice daily administration. The present invention relates to vasopressin analog that will be slowly activated in the blood and can potentially be administered once a day, once every two days, once every three to six days or even once a week. This would be ideal as a second line of treatment for the management of septic shock patients not responding to high dose of inotropes, e.g., dopamine or norepinephrine. It had been shown that vasopressin analogs are more effective than epinephrine in asystolic cardiac arrest (Wenzel V, et al. A Comparison of Vasopressin and Epinephrine for Out-of-Hospital Cardiopulmonary Resuscitation. *N Engl J Med* 2004; 350:105-13). While not all studies are in agreement, a 2006 study of out-of hospital cardiac arrests has added to the evidence for the superiority of vasopressin or its analogs in this situation (Crit Care. 2006 February; 10(1):R13 (Crit Care. 2006 February; 10(1):R13). This effectiveness can be further enhanced if the vasopressin analogs are longer-acting than those that exist today.

Vasopressin analogs in the present invention can also be used for non-liver disease-related disorders such as anesthesia-associated hypotension, refractory septic shock, asystolic cardiac arrest, bronchoscopy-related bleeding, burns—grafting-associated bleeding, colonization of uterine cervix (for cervical neoplasia) associated bleeding, and labor-related blood loss.

One embodiment of the invention is a fatty acid containing analog of a biologically active peptide, which may or may not be biologically active as an analog, that can be easily activated in biological fluid by removal of fatty acid containing moiety by endogenous enzyme. The term peptide as used herein means polymers of less than 100 amino acids. Further, the analogs of the present invention can optionally be loaded into a polymeric carrier containing cores of a protective polymeric or non-polymeric carrier with linked hydrophobic groups that allows for slow release of the peptide analogs in biological fluids for subsequent activation or removal of the fatty acid containing moiety. An example of a polymeric carrier comprising protective polymeric carrier containing hydrophobic groups is described in U.S. patent application Ser. No. 11/613,183, which is hereby incorporated by reference. This loading can further slow down the activation or removal of the fatty acid containing moiety or its degradation to provide a sustained level of peptide activity in biological fluids over a longer period of time. In addition, the modification of peptide or its analogs with fatty acids allows for micelle formation that slows down the activation and degradation of the analogs in biological fluids and can potentially slow down the activation in blood. In another embodiment of the present invention, the peptide can be modified to contain a chelating molecule to facilitate loading into the polymeric carrier with coordinately immobilized or chelated metal ion which will slow down the release of and subsequent activation or degradation of the peptide in biological fluids. The term loading as used herein means reversible attachment of peptide to the carrier including metal bridges as described in U.S. Pat. No. 7,138,105 B2, which is hereby incorporated by reference.

We have found that fatty acid-containing analogs of vasopressin, a synthetic peptide previously used in the control of bleeding esophageal varices, can be easily activated in serum. Further, the vasopressin analogs of the present invention can be loaded into a protective polymeric nanocarrier containing hydrophobic groups. This loading can slow down the activation into active vasopressin to provide sustain level of vasopressin in biological fluids over a long period of time. In addition the modification of vasopressin analog, terlipressin, with fatty acids allows for micelle formation that slows down the activation of the analogs in biological fluids and can potentially slow down the activation in blood.

The histidine-, iminodiacetic acid- or nitrilodiacetic acid-containing analogs of vasopressin or other peptides can also be easily activated in biological fluids by proteases, or they may be self-activating. Further, the vasopressin analogs of the present invention can be loaded into a protective polymeric or non-polymeric nanocarrier containing chelated metals. This loading can slow down conversion of histidine containing analog of vasopressin into active vasopressin and can provide a sustained level of vasopressin in biological fluid over a long period of time.

The present invention relates to peptide analogs having the general formula: A-(Cm)$_x$-peptide (SEQ ID NO: 76) or peptide-(Cm)$_x$-A (SEQ ID NO: 77), wherein the left side of the peptide is N-terminal and the right side is C-terminal; Cm is Gly, Ala, Arg, Lys, a moiety of formula (N)$_q$-Arg, wherein N is any amino acid and q is 0 or 1, or a moiety of formula (N)$_q$-Lys, wherein N is any amino acid and q is 0 or 1, and x is an integer from 0-6; A can be any chemical group or moiety containing alkyl group having 6 to 36 carbons, a nitrilotriacetic acid group, an imidodiacetic acid group, or a moiety of formula (Z$_y$His$_w$)$_p$ (SEQ ID NO: 50), wherein Z is an amino acid residue other than histidine, His is histidine, y is an integer from 0-6, w is an integer from 1-6, p is an integer from 1-6, and x is an integer from 2-6. The peptide can be any sequence or chain of 5-100 amino acids. Amino acids in the chain can be any combination of the 20 naturally occurring amino acids or their derivatives.

The present invention also relates to a vasopressin analog having the general formula: A-Gly-Gly-Gly-Cys-Tyr-Phe-Gln-Asn-Cys-Pro-B-C-D (SEQ ID NO: 1) wherein A is chemical group or moiety containing alkyl group with 3 to 36 carbon units, nitrilotriacetic acid group, imidodiacetic acid group, or (His)$_x$ group (SEQ ID NO: 51), where x is an integer from 2-6; Gly is Glycine; Cys is Cystine or Cysteine; Tyr is Tyrosine; Phe is Phenylalanine; Gln is Glutamine; Asn is Aspargine; Pro is proline; B is Lysine or Arginine; C is Glycine or Alanine; D is NH$_2$ or H.

In another embodiment of above aforementioned composition, A is a group containing a linear alkyl group with the formula $CH_3(CH_2)_n$—CO—, wherein n is an integer 4-34. In another embodiment of above aforementioned composition, A is a branched alkyl carbonyl group with 6-36 carbon units. In another embodiment of above aforementioned composition, A is $(His)_x$- (SEQ ID NO: 51), wherein x is an integer from 2-6.

It is understood that in the above composition where A contains alkyl group(s), the composition can form micelle that will slow down the activation and degradation of vasopressin analogs in the absence of any polymeric carrier.

The present invention also relates to the aforementioned composition, further comprising polymeric carrier with hydrophobic group(s) or polymeric carrier with covalently linked metal binding domains and chelated metal. It is the object of the present invention to attach the histidine portion, nitrilotriacetic acid, or imidodiacetic acid portion of the vasopressin analogs to the metals chelated by the metal binding domains of the polymeric carrier by coordination bonding between the histidine, nitrilotriacetic acid, or imidodiacetic acid and the metal chelated by the polymeric carrier. It is also the object of the present invention to non-covalently attach the alkyl portion of the vasopressin analogs to the hydrophobic portion of the polymeric carrier. These attachments will protect the analogs from rapid degradation in vivo but will allow for the slow release of the vasopressin analogs into the circulation for activation. Essentially the polymeric carrier will act as a reservoir for the vasopressin analogs which will release the analogs depending on their dissociation constant (Kd) with the carrier. As the amount of unbound analogs gets used up by 1) protease that activates it, or 2) by its physiological receptors, more analogs will be released for further activation or utilization. As a result, a sustained level of vasopressin will remain active in the blood for a longer period of time.

In general, in one aspect compositions are provided. The compositions include compounds of the general formula A-$(Cm)_x$-peptide (SEQ ID NO: 76), wherein the peptide is a biologically active peptide having no more than 100 amino acids; Cm is a Gly moiety, wherein x is an integer from 0-6; or a Ala moiety, wherein x is an integer from 0-6; or a Arg moiety, wherein x is an integer from 0-6; or a Lys moiety, wherein x is an integer from 0-6; or a moiety of formula $(N)_q$-Arg, wherein N is any amino acid and q is 0 or 1 and x is an integer from 0-6; or a moiety of formula $(N)_q$-Lys, wherein N is any amino acid and q is 0 or 1 x is an integer from 0-6; and A is an alkyl group having 6 to 36 carbons and x is an integer from 2-6; or a nitrilotriacetic acid moiety; an iminodiacetic acid moiety; or a moiety of formula $(Z_y His_w)_p$ (SEQ ID NO: 50), wherein Z is an amino acid residue other than histidine, His is histidine, y is an integer from 0-6, w is an integer from 1-6, p is an integer from 1-6, and x is an integer from 2-6. In an exemplary embodiment, A is $His_6$ (SEQ ID NO: 52). In some aspects, the compounds of the composition include a Cm wherein Cm is Gly and A-$(Gly)_x$ (SEQ ID NO: 57) is attached to the peptide through an amide bond at the N-terminus. In one embodiment, Cm is Gly and A-$(Gly)_x$ (SEQ ID NO: 57) is attached to the peptide through a side chain of an amino acid of the peptide. In another embodiment Cm is Gly and A-$(Gly)_x$ (SEQ ID NO: 57) is attached to the peptide through an amide bond at the C-terminus. In another embodiment, the composition can have a general formula of A-$(Cm)_x$-peptide (SEQ ID NO: 78), wherein $(Cm)_x$ is Gly-Gly-Gly-; A- is amide bonded to the amino terminus of -Gly-Gly-Gly-; and A-Gly-Gly-Gly- is amide bonded to any amino group of the peptide. In an example of the foregoing embodiment, the peptide is a vasopressin analog having the general formula Cys-Tyr-Phe-Gln-Asn-Cys-Pro-B-C-D (SEQ ID NO: 53), wherein B is lysine or arginine; C is glycine or alanine; and D is $NH_2$ or H. In another example of the foregoing embodiment, the peptide is GLP and A-$(Cm)_x$- is not attached to the N terminus of the peptide. The foregoing embodiments may also include compositions where A is a linear alkyl carbonyl group with formula $CH_3(CH_2)_n$—CO—; wherein n is an integer between 4-34, or n is 6 or 10 and Cm is Gly-Gly-Gly. In another example of the forgoing embodiments, A is a branched alkyl carbonyl group with 6-36 carbon units attached through the carbon of the carbonyl group. In one embodiment, the vasopressin analog is $CH_3(CH_2)_6CO$—$OCH(CH_3)CO$-Gly-Gly-Gly-Cys-Tyr-Phe-Gln-Asn-Cys-Pro-Lys-Gly-$NH_2$ (SEQ ID NO: 37). In another embodiment, the vasopressin analog is His-His-His-His-His-His-Gly-Gly-Gly-Cys-Tyr-Phe-Gln-Asn-Cys-Pro-Lys-Gly-$NH_2$ (SEQ ID NO: 38).

In another aspect, the foregoing compositions further include a polymeric carrier with multiple alkyl chains of 6-36 carbon units wherein the alkyl carbonyl groups of a plurality of peptide analog compounds are non-covalently bound to the multiple alkyl chains of the polymeric carrier by hydrophobic interaction. In another embodiment, the foregoing compositions further a include polymeric carrier with covalently linked metal binding domains and chelated metal ions.

In another aspect, the compositions include a polymeric carrier comprising a polymeric core; a plurality of first hydrophobic groups covalently bound to the polymeric core; a plurality of protective side chains, wherein each protective side chain is covalently bound to the polymeric core and has a molecular weight between about 400 and 20,000 Daltons independent of the polymeric core weight; and a plurality of peptide analogs, each comprising a peptide covalently bound to a second hydrophobic group, wherein said peptide analogs are non-covalently bound to the polymeric carrier through a hydrophobic interaction between the first hydrophobic groups and the second hydrophobic groups. In one embodiment, the peptide is a vasopressin analog having the general formula: Cys-Tyr-Phe-Gln-Asn-Cys-Pro-B-C-D (SEQ ID NO: 53), wherein B is lysine or arginine, C is glycine or alanine, and D is $NH_2$ or H. In embodiments of the foregoing, the hydrophobic group is a linear alkyl carbonyl group with formula $CH_3(CH_2)_n$—CO, wherein n is an integer between 4-34. In an exemplary embodiment of the foregoing, the vasopressin analog is $CH_3(CH_2)_6CO$—$OCH(CH_3)CO$-Gly-Gly-Gly-Cys-Tyr-Phe-Gln-Asn-Cys-Pro-Lys-Gly-$NH_2$ (SEQ ID NO: 37). In another embodiment, the peptide of the foregoing compositions is GLP. In an exemplary embodiment, the peptide analog of the foregoing compositions is GLP-Gly-Gly-Gly wherein Gly-Gly-Gly- is attached to the C terminus or a side chain of the peptide.

In another aspect, the compositions include a polymeric carrier comprising a polymeric core; a plurality of first chelating groups covalently bound to the polymeric core, wherein the first chelating groups are coordinately bonded to a transition metal ion; a plurality of first protective side chains, wherein each first protective side chain is covalently bound to the polymeric core and has a molecular weight between about 400 and 20,000 Daltons independent of the polymeric core weight; and a plurality of peptide analogs, each comprising a peptide covalently bound to a second chelating group, wherein said peptide analogs are non-covalently bound to the polymeric carrier through a coordinate bond to the transition metal ion. In one embodiment, the peptide is a vasopressin analog having the general formula: Cys-Tyr-Phe-Gln-Asn-Cys-Pro-B-C-D (SEQ ID NO: 53), wherein B is lysine or arginine, C is glycine or alanine, and D is $NH_2$ or H. In an exemplary embodiment, the vasopressin analog has the formula His-His-His-His-His-His-Gly-Gly-Gly-Cys-Tyr-Phe-Gln-Asn-Cys-Pro-Lys-Gly-NH$_2$ (SEQ ID NO: 38). In another embodiment, the peptide of the foregoing compositions is GLP. In an exemplary embodiment, the peptide analog of the foregoing compositions is GLP-Gly-Gly-Gly wherein Gly-Gly-Gly- is attached to the C terminus or a side chain of the peptide.

In another aspect of the invention, the foregoing compositions are formulated in a pharmaceutically acceptable carrier.

In yet another aspect, the invention provides methods of administering the foregoing compositions to a patient. In one embodiment, the invention provides methods of administering the foregoing vasopressin analogs to a patient in the treatment of hypovolemia, splanchnic vasodilation, systemic vasodilation, hypotension, esophageal variceal hemorrhage, hepatorenal syndrome, liver cirrhosis caused by alcohol or hepatitis, or sepsis.

In yet another aspect, the invention provides a composition comprising a peptide analog having a general formula: A-(Cm)$_x$-peptide. Wherein, Cm is chosen form a group consisting of glycine, alanine, lysine, and arginine, x is an integer from 3-6, A is a chemical group or moiety comprising an alkyl group with 6 to 36 carbon units with a —OCH(CH$_3$)CO— linker attached to -(Cm)$_x$-peptide and peptide is any peptide with at least 8 amino acids and is not SEQ ID NO: 53. The A-(Cm)$_x$-peptide has lower biological activity in cell culture than the parent peptide in the absence of serum.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 5. The figure depicts a chemical structure of vasopressin with three glycine residues at the N-terminus attached to octanoic acid via lactic acid ester. This is also referred to as "C8TerE". Using reverse phase HPLC chromatography in a Rainin (C18, 5 μm, 4.6×250 mm) eluted with a linear gradient from 10% acetonitrile/water/0.1% TFA to 70% acetoinitrile/water/0.1% TFA over 45 minutes at a flow rate of 1 ml/min, the C8TerE showed retention time of 27.32 minutes as monitored at 220 nm and showed greater than 95% purity. Using mass spectrometer for total ion current the purity was confirmed and a mass of 1425.7 Dalton was found corresponding to protonated peptide or the molecular ion peak on mass spectroscopic analysis. This is consistent with the theoretical molecular mass of 1426.5 Dalton when protonated. The absorption spectra showed a peak at 260 nm, which is about 40 times less than at 210 nm.

Figure 8:
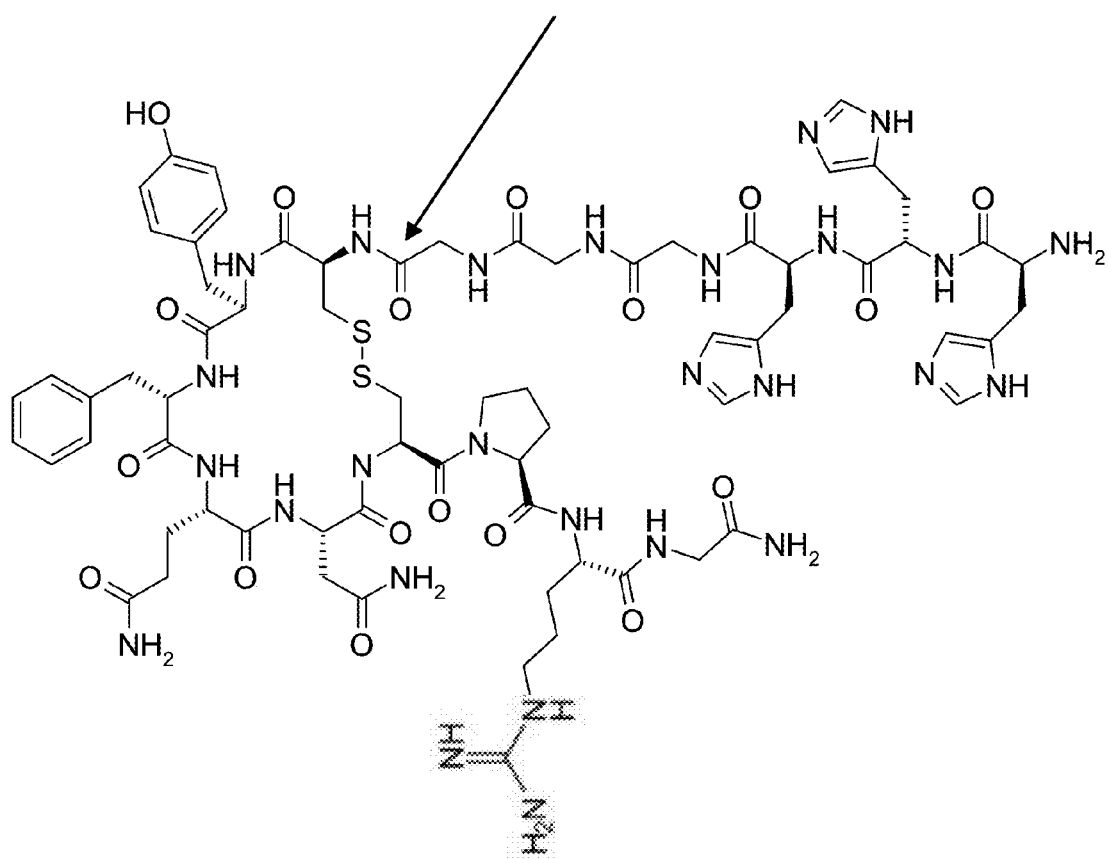

FIG. 8. The figure depicts a chemical structure of arginine vasopressin with three glycine residues at the N-terminus attached to three Histidine residues. This is also referred to as "His3Vas". Using reverse phase HPLC chromatography in a Rainin (C18, 5 μm, 4.6×250 mm) eluted with a linear gradient from 0% acetonitrile/water/0.1% TFA to 60% acetoinitrile/water/0.1% TFA over 45 minutes at a flow rate of 1 ml/min, the His3Vas showed retention time of 18,45 minutes as monitored at 215 nm and showed greater than 95% purity. Using mass spectrometer for total ion current the purity was confirmed and a mass of 1668 Dalton was found corresponding to protonated peptide or the molecular ion peak on mass spectroscopic analysis. This is consistent with the theoretical molecular mass of 1667.9 Dalton when protonated. The absorption spectra showed a peak at 260 nm, which is about 38 times less than at 210 nm.

Figure 9:
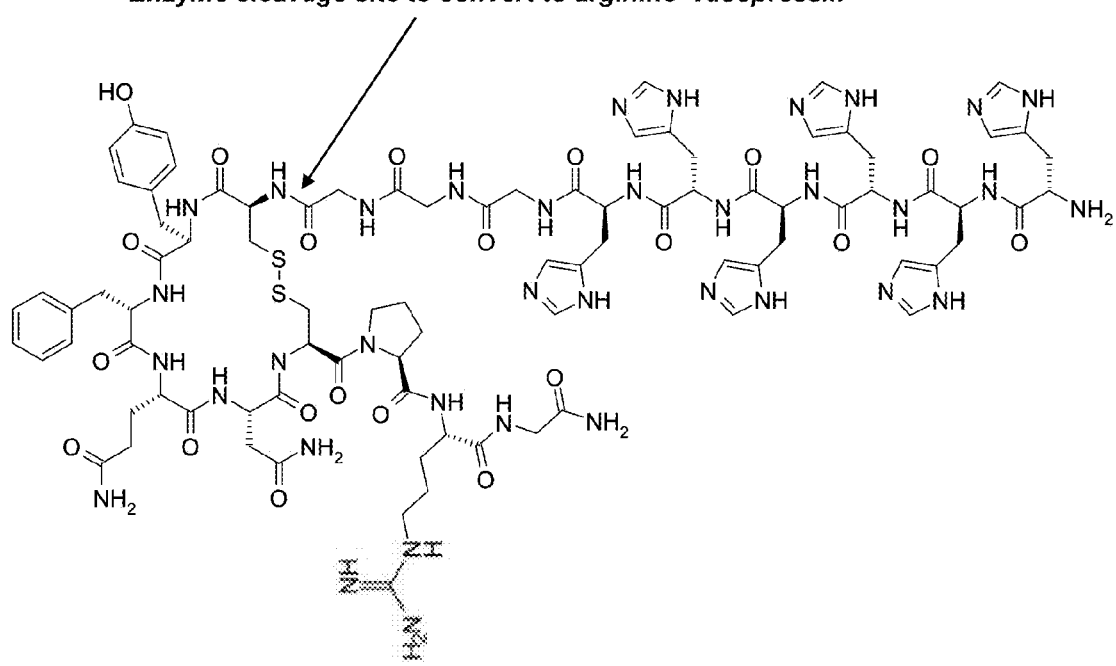

FIG. 9. The figure depicts a chemical structure of arginine vasopressin with three glycine residues at the N-terminus attached to six histidine residues (SEQ ID NO: 52). This is also referred to as "His6Vas" ("His6" disclosed as SEQ ID NO: 52). Using reverse phase HPLC chromatography in a Supelco (C18, 5 μm, 4.6×250 mm) eluted with a linear gradient from 0% acetonitrile/water/0.1% TFA to 60% acetoinitrile/water/0.1% TFA over 45 minutes at a flow rate of 1 ml/min, the His6Vas ("His6" disclosed as SEQ ID NO: 52) showed retention time of 17.27 minutes as monitored at 220 nm and showed greater than 95% purity. Using mass spectrometer for total ion current the purity was confirmed and a mass of 2080.5 Dalton was found corresponding to protonated peptide or the molecular ion peak on mass spectroscopic analysis. This is consistent with the theoretical molecular mass of 2079.3 Dalton when protonated. The absorption spectra showed a peak at 260 nm, which is about 48 times less than at 210 nm.

Figure 10:
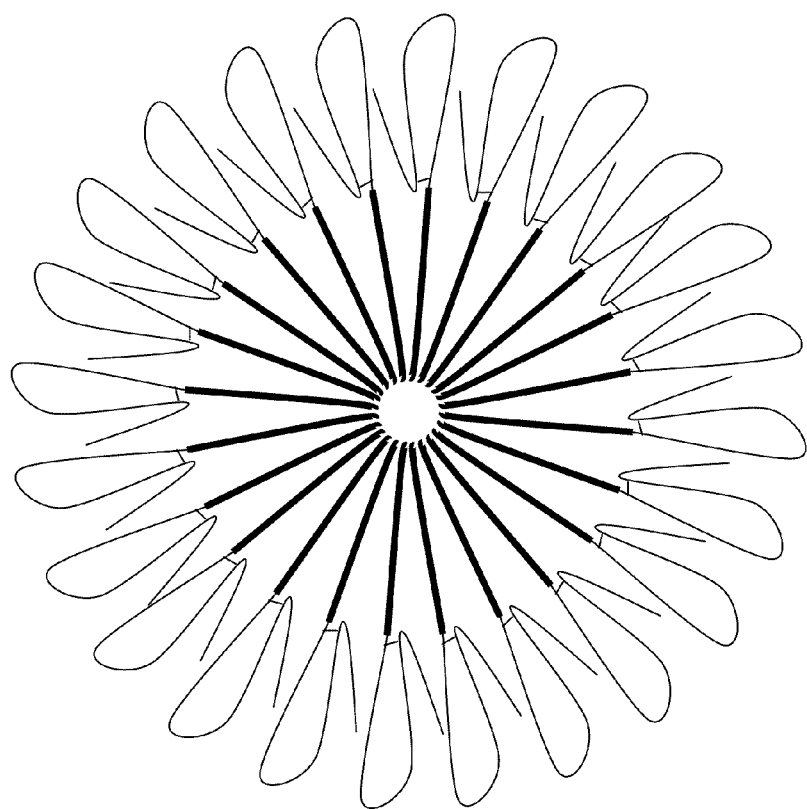

FIG. 10. The figure depicts a schematic cross section of the micelle that forms from vasopressin analogs containing fatty chain. The dark heavy line is the hydrophobic chains while the light line represent the vasopressin with disulfide bonds. The cleavage sites shown in FIGS. 1 to 5 are hidden from the surface of the micelle, and in this figure is at the junction of light and heavy line.

Figure 11:
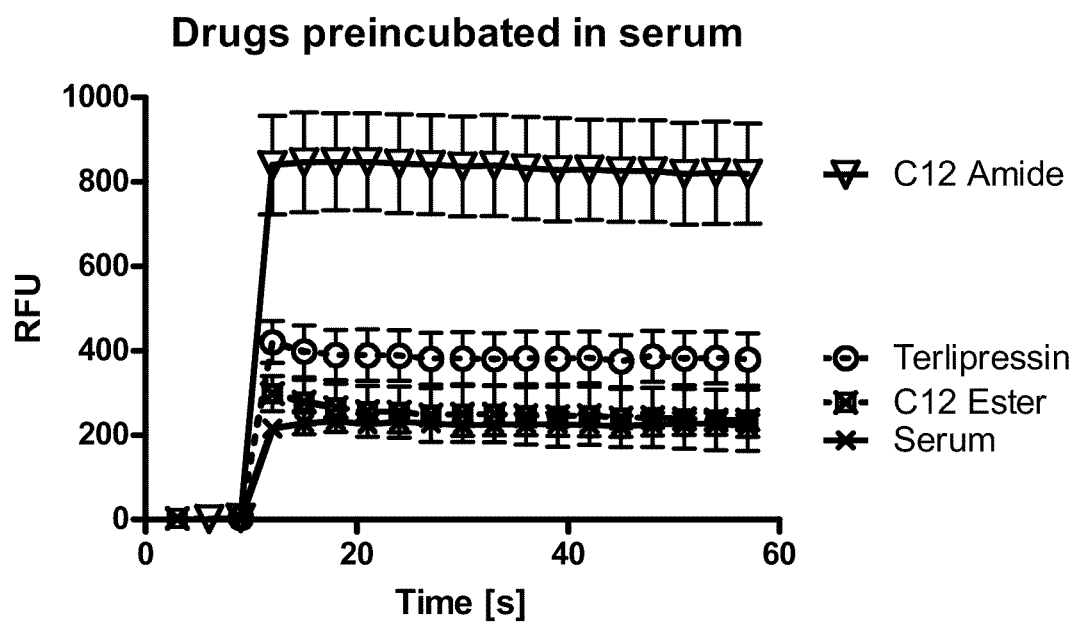

FIG. 11. This figure shows the ability of terlipressin and other vasopressin analog to be activated by serum after 2-hour incubation in human serum. The Y-axis is relative fluorescence units in human umbilical chord cells loaded with fura-2 in 96-well plate. The fluorescence is proportional to the calcium in cells cytoplasm. Vasopressin causes calcium influx into the cells cytoplasm causing an increase in fluorescence. Various vasopressin analogs are incubated with human serum for 2 hours and applied to cells in culture. Fluorescence was measured at three second intervals for one minute. as shown. After application, those samples that get activated by serum cause calcium influx and hence increase in fluorescence.

Figure 12:
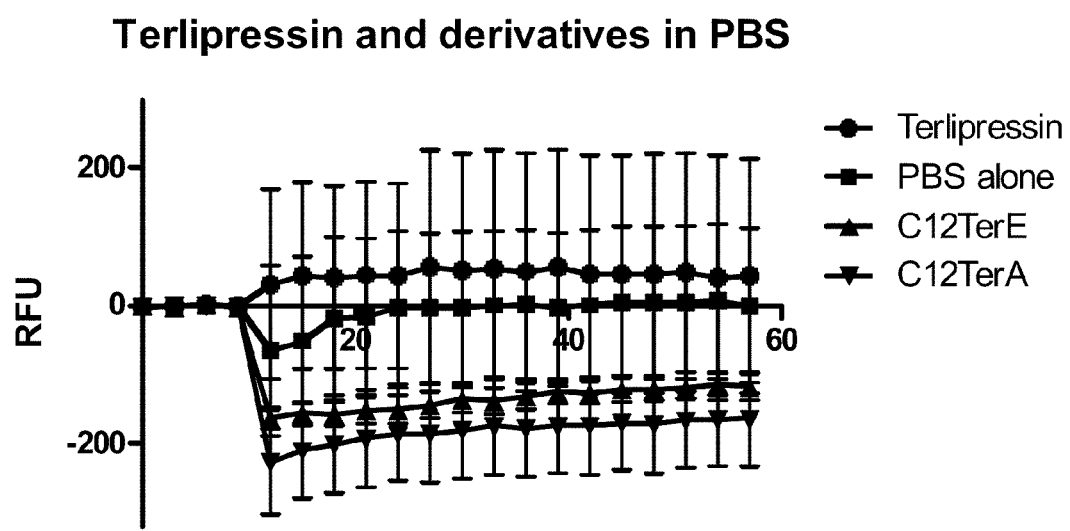

FIG. 12: All figures show 20 repeats of Fura-2 fluorescence as a function of time in seconds on the x-axis. The y-axis shows fluorescence intensity in relative fluorescence units [RFU]. After the first 4 data time points, the drugs are injected into the tissue culture well and fluorescence measurement is continued for 48 more seconds. Fura-2 fluorescence intensifies as intra-cellular $Ca^{2+}$ concentration rise in response to a stimulus. Terlipressin is only fully active when injected in the presence of serum since, as being an analogue, a short sequence of amino acids needs to be cut off to leave fully active vasopressin. This step is very fast or the enzyme performing this step is active on ice as the addition of human serum increases terlipressin activity significantly without pre-incubation at 37° C. Terlipressin loses its activity quickly due to degradation with increasing incubation time in serum. Because of endogenous growth factors contained in human serum, human serum by itself produces a measurable Ca-influx signal. Activity of the drugs therefore needs to exceed the human serum signal. The C8TerA, C12TerA and C12TerE derivatives of terlipressin are similarly active but are protected for up to 4 h from degradation in serum.

Figure 13:
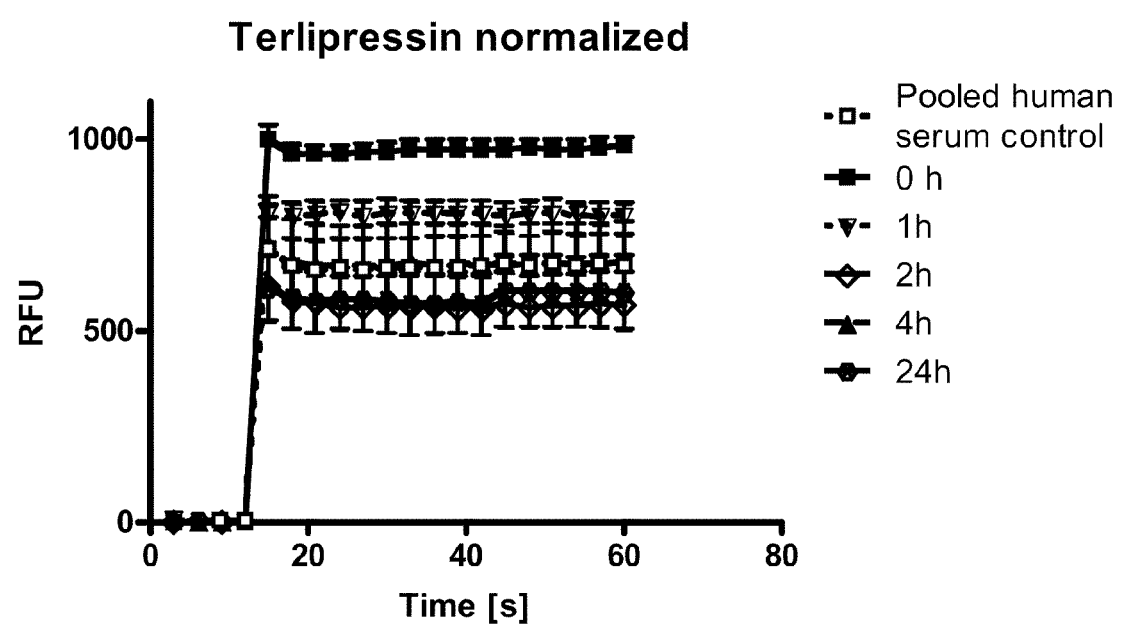

FIG. 13: Results from the method of FIG. 12 showing terlipressin and derivatives in PBS.

Figure 14:
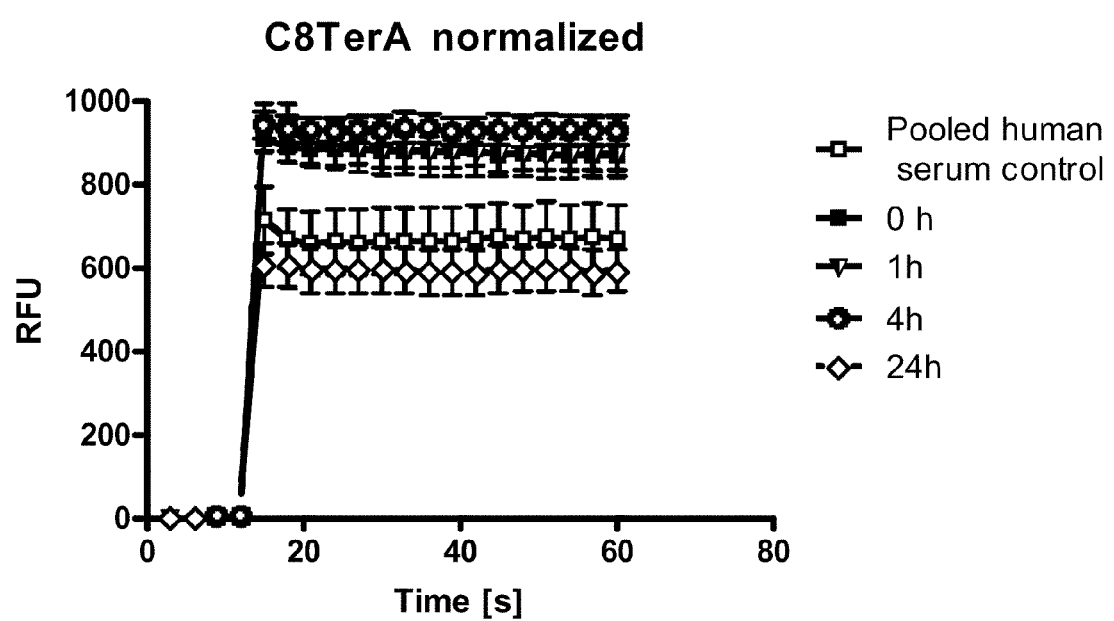

FIG. 14: Results from the method of FIG. 12 showing teripressin in human serum for varying intervals.

Figure 15:
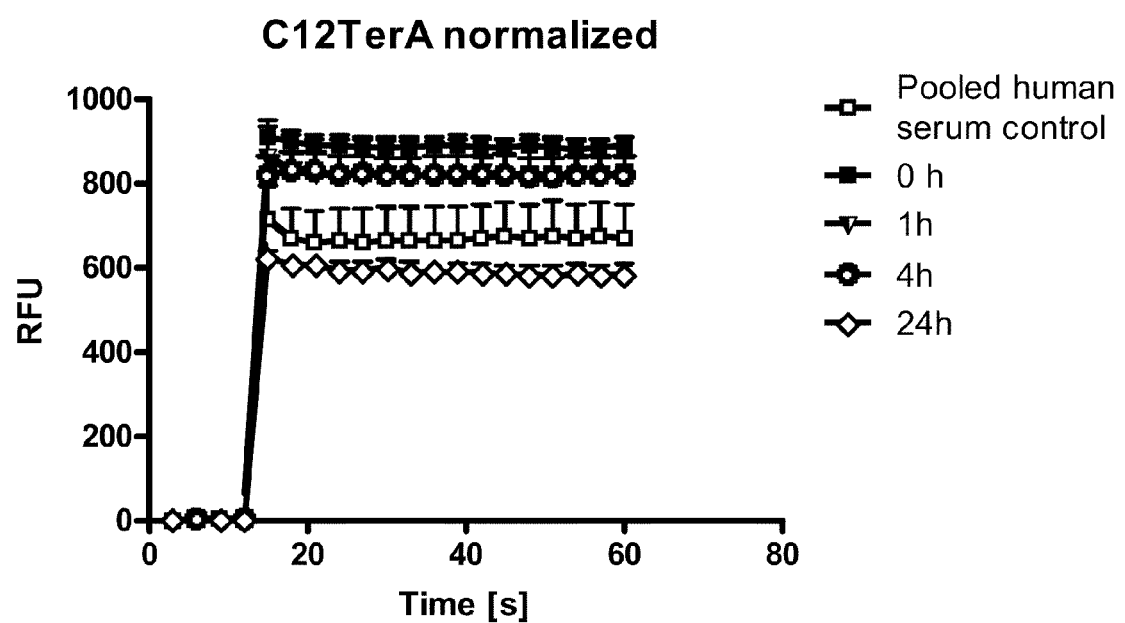

FIG. 15: Results from the method of FIG. 12 showing C8TerA analog in human serum for varying intervals.

Figure 16:
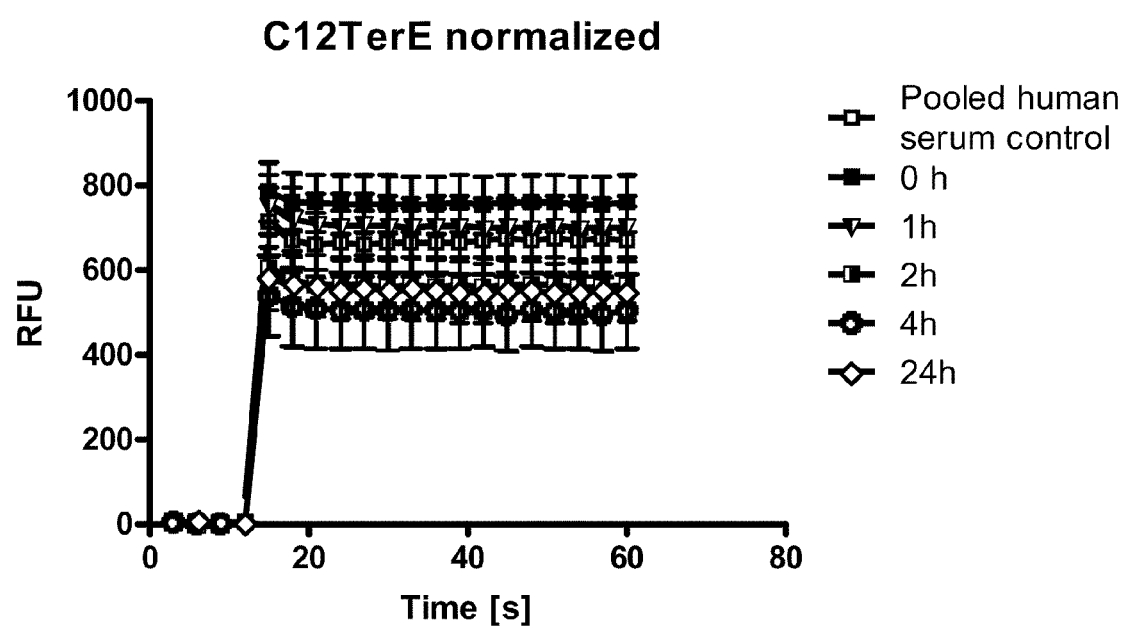

FIG. 16: Results from the method of FIG. 12 showing C12TerA analog in human serum for varying intervals.

Figure 17:
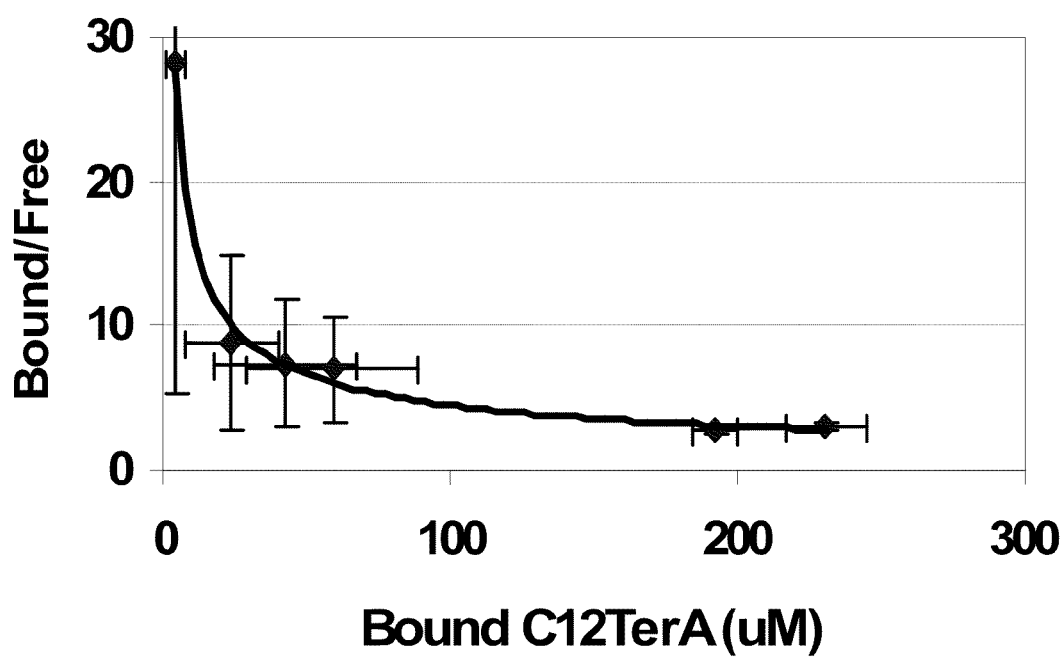

FIG. 17: This figure is a Scatchard plot showing the binding of C12TerA to polymeric carrier containing a hydrophobic group disclosed in U.S. patent application Ser. No. 11/613,183, which is hereby incorporated by reference. The carrier also referred to as PGC-HC18 or 20PLPEG555-C18 is made up of polylysine of 15-30 kDa where 55% of the amino group is covalently modified to contain 5 kDa methoxypolyethylene glycol attached by through succinate linker and the remaining 45% of the amino group is amide bonded to stearic acid carboxyl group all disclosed in U.S. patent application Ser. No. 11/613,183. Two hundred fifty μl solutions of carrier (2.5 mg/tube) were mixed with 0.20, 0.15, 0.10, 0.075, 0.050, and 0.025 mg of C12TerA. Sample was made up to 150 μl PBS and incubated overnight. The bound from 75 μl was eluted from Bio-spin-P30. The void volume containing loaded carrier was unloaded by filtration through 100 kDa MWCO filter after addition of 75 μl acetonitrile, to release load. The filtrate containing bound C12TerA was quantified by HPLC. A controlled passed through the same filter in 50% acetonitrile was used as a reference for the total C12TerA in each tube, allowing for the calculation of Free C12TerA in the original incubation mixture. C12-TerA elutes at 2.4 minutes. A gradient of 25-99% acetonitrile from 1-6 minutes at a flow rate of 1.5 ml/min was used. The column was Mercury MS 20×4 mm; 2 um; C12 from Phenomenex. Although the Scatchard plot is not completely linear, an average Kd of 1-5 μM can be estimated, indicating a strong interaction of C12TerA with the carrier containing the hydrophobic group, which is sufficient to prolong the biological half-life of the C12TerA and delay its rapid activation and degradation. It should be noted that some C12TerA can form micelle and may be counted as bound due to the analytical techniques used.

Figure 18:
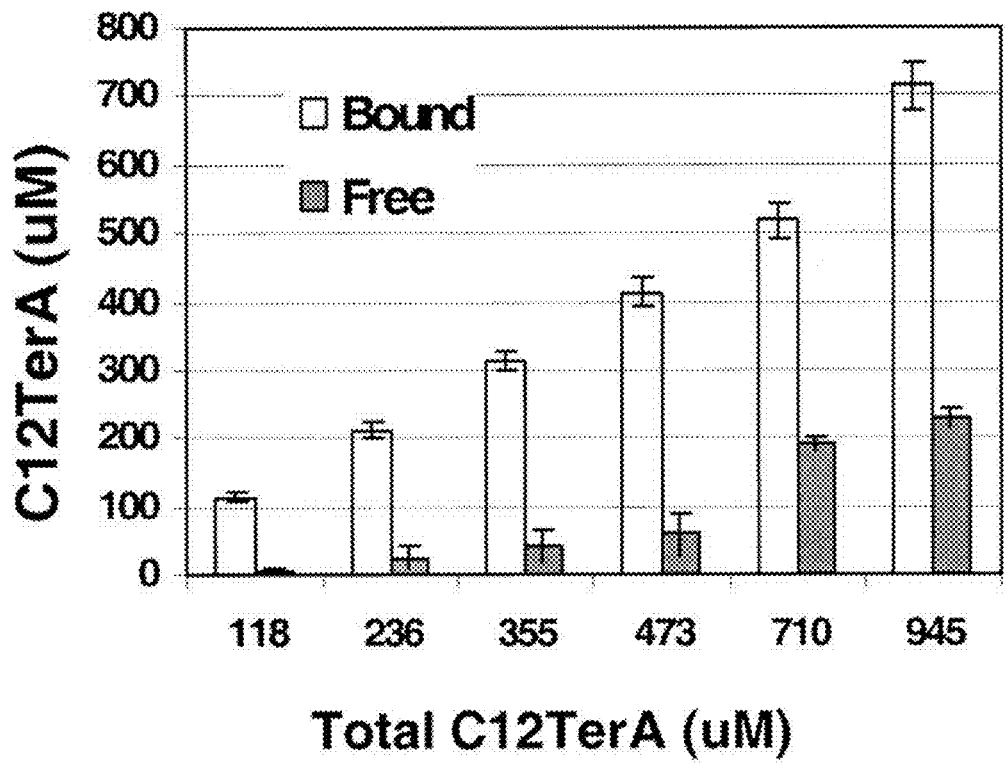

FIG. 18: The graph shows the bound and Free C12TerA in the presence of 10 mg/ml PGC-HC18 or 20PLPEG555-C18. It should be noted that most of the C12TerA is bound to the carrier containing hydrophobic group, which is sufficient to prolong the biological half-life of the C12TerA and delay its rapid activation and degradation.

Figure 19:
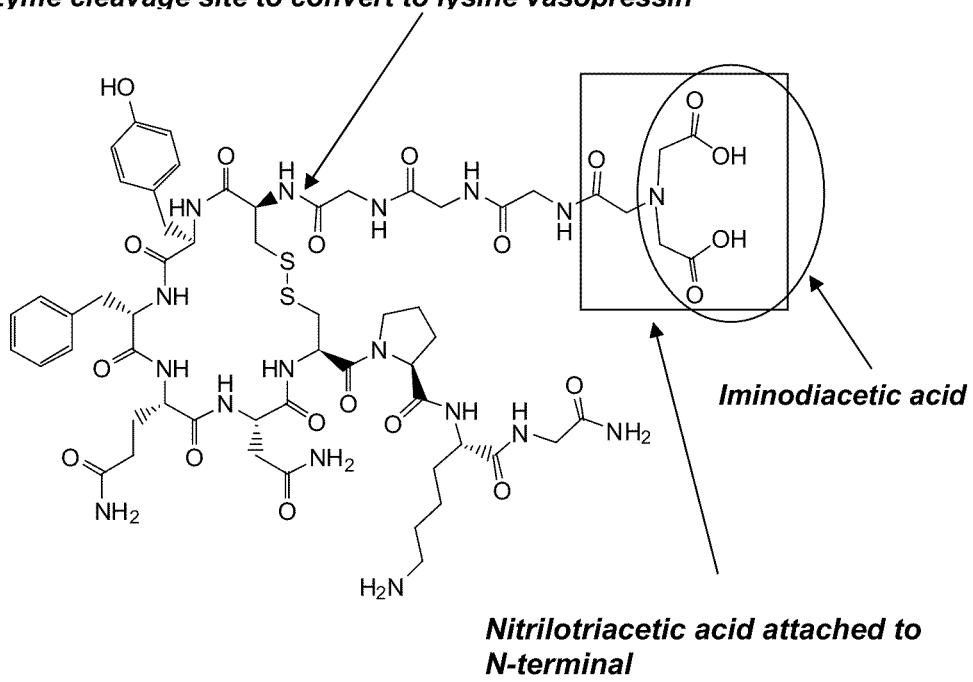

FIG. 19: The figure depicts a chemical structure of vasopressin with three glycine residues at the N-terminus attached to one of the carboxyl group of nitrilotriacetic acid. This is also referred to as "NTA-Ter". This can also be looked at as vasopressin with four glycine residues where the N-terminus is attached to two carboxymethyl groups.

Figure 20:
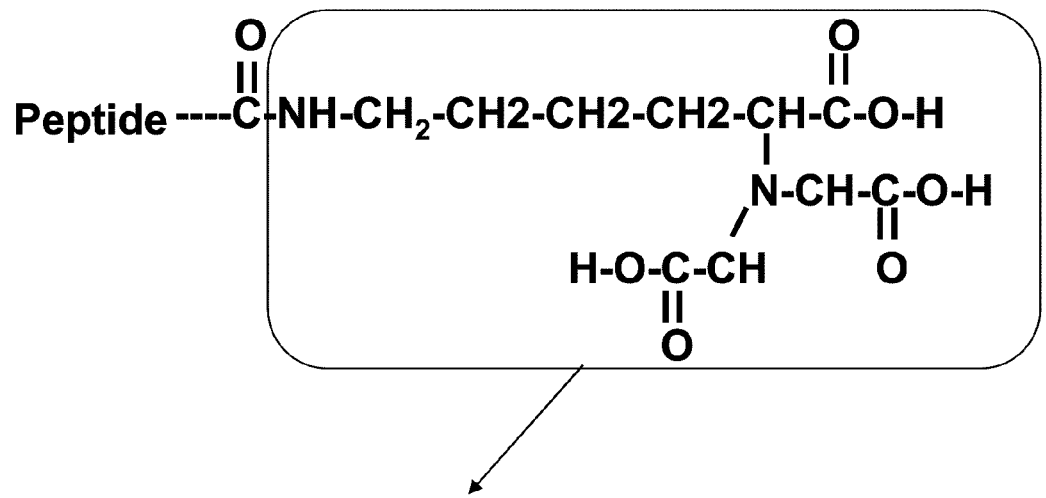

FIG. 20: The figure depicts a chemical structure of peptide in general with nitrilotriacetic acid derivative [N',N',bis(carboxymethyl)-lysine] attached to the carboxyl terminal of peptide that allows the peptide to have nitrilotriacetic acid residue. In one particular embodiment, the peptide can have sequence of: His-Ala-Glu-Gly-Thr-Phe-Thr-Ser-Asp-Val-Ser-Ser-Tyr-Leu-Glu-Gly-Gln-Ala-Ala-Lys-Glu-Phe-Ile[[u]]-Ala-Trp-Leu-Val-Lys-Gly-Arg (SEQ ID NO: 2); or His-Ala-Glu-Gly-Thr-Phe-Thr-Ser-Asp-Val-Ser-Ser-Tyr-Leu-Glu-Gly-Gln-Ala-Ala-Lys-Glu-Phe-Ile[[u]]-Ala-Trp-Leu-Val-Lys-Gly-Arg-Gly (SEQ ID NO: 3); or His-Ala-Glu-Gly-Thr-Phe-Thr-Ser-Asp-Val-Ser-Ser-Tyr-Leu-Glu-Gly-Gln-Ala-Ala-Lys-Glu-Phe-Ile[[u]]-Ala-Trp-Leu-Val-Lys-Gly-Arg-Gly-Gly (SEQ ID NO: 4); or His-Ala-Glu-Gly-Thr-Phe-Thr-Ser-Asp-Val-Ser-Ser-Tyr-Leu-Glu-Gly-Gln-Ala-Ala-Lys-Glu-Phe-Ile[[u]]-Ala-Trp-Leu-Val-Lys-Gly-Arg-Gly-Gly-Gly (SEQ ID NO: 5). The three letter codes are the amino acid representations known in the art of peptides.

Figure 21:
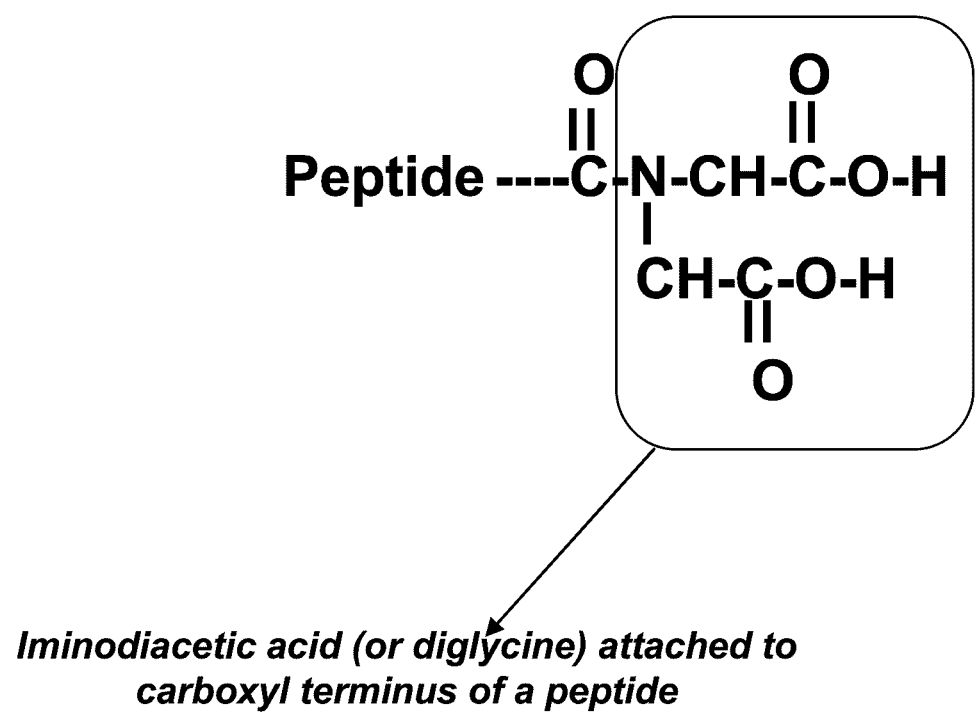

FIG. 21: The figure depicts a chemical structure of peptide in general with iminodiacetic acid attached to carboxyl terminal of peptide that allows the peptide to have iminodiacetic acid residue. In one particular embodiment, the peptide can have sequence of: His-Ala-Glu-Gly-Thr-Phe-Thr-Ser-Asp-Val-Ser-Ser-Tyr-Leu-Glu-Gly-Gln-Ala-Ala-Lys-Glu-Phe-Ileu-Ala-Trp-Leu-Val-Lys-Gly-Arg (SEQ ID NO: 2); or His-Ala-Glu-Gly-Thr-Phe-Thr-Ser-Asp-Val-Ser-Ser-Tyr-Leu-Glu-Gly-Gln-Ala-Ala-Lys-Glu-Phe-Ileu-Ala-Trp-Leu-Val-Lys-Gly-Arg-Gly (SEQ ID NO: 3); or His-Ala-Glu-Gly-Thr-Phe-Thr-Ser-Asp-Val-Ser-Ser-Tyr-Leu-Glu-Gly-Gln-Ala-Ala-Lys-Glu-Phe-Ileu-Ala-Trp-Leu-Val-Lys-Gly-Arg-Gly-Gly (SEQ ID NO: 4); or His-Ala-Glu-Gly-Thr-Phe-Thr-Ser-Asp-Val-Ser-Ser-Tyr-Leu-Glu-Gly-Gln-Ala-Ala-Lys-Glu-Phe-Ileu-Ala-Trp-Leu-Val-Lys-Gly-Arg-Gly-Gly-Gly (SEQ ID NO: 5). The three letter codes are the amino acid representations known in the art of peptides.

Figure 22:
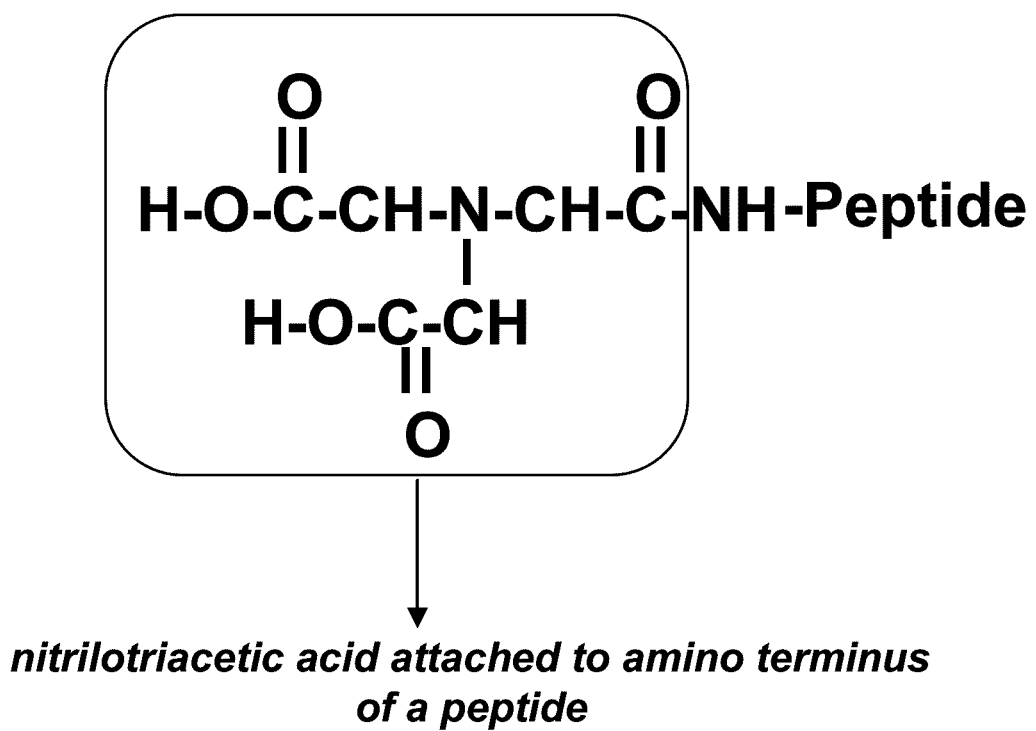

FIG. 22: The figure depicts a chemical structure of peptide in general with nitrilotriacetic acid attached to the amino terminus or N-terminus of peptide that allows the peptide to have an iminodiacetic acid residue. This is another embodiment of the present invention.

Figure 23:
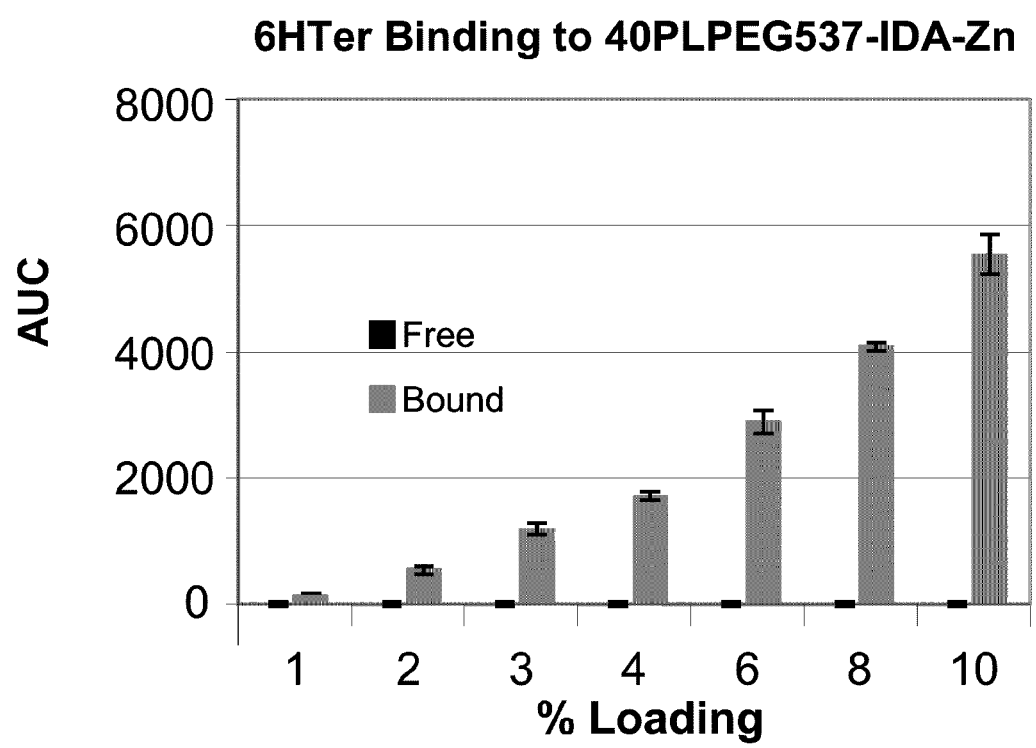

FIG. 23: This is a graph showing the bound and Free His6Ter ("His6" disclosed as SEQ ID NO: 52) in the presence of 10 mg/ml 40PLPEG537-Zn-chelate. The 40PLPEG537-Zn-chelate has a 40 kDa polylysine backbone with 37% of the lysine epsilon amino groups attached to 5 kDa polyethyleneglycol and the remaining 63% attached to Zn ion chelate, as described in U.S. Pat. No. 7,138,105. The percent loading in the x-axis represent the amount of His6Ter ("His6" disclosed as SEQ ID NO: 52) as a percent of 10mg/ml carrier. It should be noted that most of the His6Ter ("His6" disclosed as SEQ ID NO: 52) is bound to the carrier containing chelated zinc which is sufficient to prolong the biological efficacy of the His6Ter ("His6" disclosed as SEQ ID NO: 52). Several aliquots of carriers (2.5 mg carrier/tube) were mixed with 0.25, 0.20, 0.15, 0.10, 0.075, 0.050, and 0.025 mg of His6Ter ("His6" disclosed as SEQ ID NO: 52) and made up to 250 µl PBS and incubated overnight. To separate bound and free, the solution was filtered using 100 kDa molecular weight cut-of cellulose filter (Microcon Ultracel YM-100 from Millipore) by centrifugation at 12,000×g for 10 minutes. The His6Ter ("His6" disclosed as SEQ ID NO: 52) in the filtrate was quantified by reverse phase HPLC using synergimax (20×4 mm) with a gradient of 0-50% B (A is 5% acetonitrile with 0.1% TFA and B is 100% acetonitrile with 0.1% TFA) from 1-5 minutes at flow rate of 1.5 minutes. His6Ter ("His6" disclosed as SEQ ID NO: 52) comes out at 3.1 minutes. Free or unbound His6Ter ("His6" disclosed as SEQ ID NO: 52) was expressed as area under the curve (AUC; y-axis). Controls without the carrier were passed through the same filter was and quantified similarly and used as a reference for the total His6Ter ("His6" disclosed as SEQ ID NO: 52) from which free can be subtracted to calculate the bound.

DETAILED DESCRIPTION OF THE INVENTION

The present disclosure provides compositions of biologically active peptide complexes, formulations and methods of use of such compositions for the treatment of patients. The subject compositions, and methods of making and using the same, may achieve a number of desirable results and features. In one aspect, the present invention is directed to complexes of peptide analogs and polymeric carrier molecules that are configured to deliver, release and/or prolong the half-life of biologically-active peptides in a controlled fashion after administration to a patient. In another aspect, the present invention is directed to complexes of peptide analogs and polymeric carrier molecules that stabilize the peptides to create formulations suitable for administration to a patient. The present disclosure provides peptides with covalently attached binding moieties of hydrophobic and/or metal binding groups ("peptide analogs") that can reversibly bind to polymeric carrier containing cores of hydrophobic polymeric carrier or polymeric carrier with covalently linked metal binding domains and chelated metal to form complexes suitable for administration to a patient. The present disclosure also provides peptides with alkyl groups that can form micelle or liposomes with or without cores of hydrophobic polymeric carrier. By way of a further embodiment, the peptide may optionally be covalently attached to hydrophobic or metal binding groups by a cleavable linker moiety that can be cleaved by host proteases in biological fluids or tissues, permitting the controlled and/or sustained release of active peptide from the delivery complex.

U.S. Pat. No. 7,138,105 and United States patent publications 2005-0260259, 2007-0141145 and 2008-0015263 describe drug polymeric carrier molecules that reversibly bind hydrophobic and metal binding molecules, such as peptides. These polymeric carrier molecules can include a polymeric core (e.g., a backbone), such as a polyamino acid, such as polylysine. Protective groups, such as polyethylene glycol can be attached to the core. Also attached to the core are binding moieties that bind the molecule to be delivered. In certain embodiments, the binding moieties bind molecules with hydrophobic groups. In this case, the binding moiety can be a hydrophobic group such as an alkyl group. Alternatively, the binding moiety binds with molecules that, themselves, bind metals. Such binding moieties include metal binding groups, such as chelating groups, bound to a metal, such as a transition metal (e.g., Zn, Ni, Cu etc.).

I. Peptide Analog Compositions

This invention provides peptides that have been modified to include binding moieties, such as hydrophobic groups or metal binding groups, through which the peptides can bind to the polymeric carrier molecules. Modifications can include hydrophobic moieties or metal binding groups to create the peptide analogs of the invention. For example, a hydrophobic group can be an alkyl having 6-36 carbon atoms. A metal binding group can be, for example, a His tag (e.g., $His_6$ (SEQ ID NO: 52)). In certain embodiments, the binding moiety is attached directly to the peptide to be delivered. In other embodiments, the binding moiety is attached to the peptide through a cleavable moiety, including sequences of amino acids such as Gly-Gly-Gly and other amino acid sequences susceptible to cleavage, as described more fully below. Thus, for the purpose of the present invention, "peptide analog" means a peptide with a covalently bound binding moiety, as well as a peptide with a covalently bound cleavable moiety and a covalently bound binding moiety. Cleavage of the cleavable moiety in the body releases the peptide from the polymeric carrier. Thus, peptide compositions of the invention have the general formula: Binding moiety—Optional cleavable moiety—Peptide, wherein the Binding moiety and Optional cleavable moiety can be bound, e.g., covalently, to the peptide at any appropriate location on the peptide. The cleavable moiety finds use when the binding moiety interferes with the biological activity of peptides.

Accordingly, this invention also provides peptide complexes between a polymeric carrier and a modified peptide of this invention in which the modified peptide is reversibly bound to the polymeric carrier through hydrophobic attraction between alkyl groups of the modified peptide and polymeric carrier, or a metal ion binding interaction between a metal binding group of the modified peptide and metal binding groups and associated metal ions of the polymeric carrier.

A. Peptides

For the purpose of the present invention, "peptide" means biologically active polyamino acids ranging from 5 to 100 amino acids. In the past, polyamino acids larger than 51 amino acids were termed proteins while 51 amino acid and smaller were termed peptides. The distinction between protein and peptide is only a matter of size. The synthesis of longer polyamino acids such as proteins has been challenging in the past due to some technology limitations of peptide synthesizers. This difficulty resulted in the distinction between peptide and proteins. The improvement in peptide synthesis technology, however, now allows for longer polypeptides up to 100 amino acids to be synthesized. It is also the intention of the present invention to include in the definition of peptide those polypeptides containing 5 to 100 amino acids since the technology now allows for the synthesis of those peptides in automated peptide synthesizer, making the old definition of peptide broader. Most large proteins are still made recombinant methods in biological systems while peptides are made using peptide synthesizers. The addition of alkyl groups, histidine, nitrilotriacetic acid, or iminodiacetic acid to a peptide can be easily done using a peptide synthesizer during peptide synthesis. For recombinant proteins, these alkyl groups, nitrilotriacetic acid, or iminodiacetic acid may be introduced in mature proteins but with limited reaction predictability from protein to protein. "Peptide" for the purpose of the present invention does not include homopolymers of amino acid such as polylysine, polyglutamic acid as they are not biologically active. The term "biologically active" for the purpose of the present invention means the peptide can bind to a cellular receptor that can send message inside the cell through a second messenger system that then causes a biological response. These are the peptides/proteins that when modified as outlined in the instant specification are the peptide of the present invention.

The biologically active peptides suitable for use in the present invention include peptides that by themselves are susceptible to enzymatic cleavage in biological fluids such as plasma or are otherwise cleared by the body such that they have a short half-life. The present disclosure provides compositions containing peptides with biological activity that are suitable for treating a patient, such as vasopressin, terlipressin, glucagon like peptide (GLP), or analogs thereof. Other non-limiting examples of peptides include, but are not limited to leptin fragment, gastric inhibitory polypeptide (GIP), epidermal growth factor (EGF) receptor ligand, EGF, transforming growth factor alpha (TGF-alpha), gastrin/cholecystokinin receptor ligand, gastrin, cholecystokinin, lysostaphin, interferon, interferon gamma, interferon beta, interferon alpha, interleukin-1, interleukin-2, interleukin-4, interleukin-6, interleukin-8, interleukin-10, interleukin-12, tumor necrosis factor, tumor necrosis factor alpha, tumor necrosis factor beta, auristatin, nisin, insulin, insulin-like growth factor, growth hormone, nerve growth factor, brain-derived neurotrophic factor, endostatin, angiostatin, trombospondin, urokinase, streptokinase, blood clotting factor VII, blood clotting factor VIII, granulucyte-macrophage colony-stimulating factor (GM-CSF), granulucyte colony-stimulating factor (G-CSF), thrombopoetin, calcitonin, parathyroid hormone (PTH) and its fragments, erythropoietin, atrial natriuretic factor, somatostatin, adrenocorticotropin, gonadotropin releasing hormone, leutinizing-hormone-releasing-hormone, follicle stimulating hormone, glucocerebrosidase, thrombopoietin, filgrastin, prostaglandins, epoprostenol, prostacyclin, desmopressin, or vasoactive intestinal peptide (VIP).

The term "derivative" as used herein refers to a compound whose core structure is the same as, or closely resembles that of, a parent compound, but which has a chemical or physical modification, such as a different or additional groups. The term "derivative" includes co-polymers of parent compounds that can be linked to other atoms or molecules. The term "derivative" also includes peptides with at least 50% sequence identity with the parent peptide. The term "derivative" also include a peptide with additional groups attached to it, such as fatty acids and/or additional amino acids, but does not include binding moieties or cleavable moieties as they are defined herein. Vasopressin as use herein includes its derivatives such as terlipressin and other variations thereof. Glucagon like peptide (GLP) as used herein includes GLP and its derivatives such as GLP-1 (7-36), GLP-1(7-37), and exenatide and other variation thereof. For clarity of the specification, a linear peptide, also referred to as polypeptide or polyamino acid, has a N-terminus and a C-terminus. The N-terminus refers to the alpha amino group of the terminal amino acid that is not used to form a peptide bond. The C-terminus refers to the alpha carboxyl group of the terminal amino acids that is not used to form a peptide bond. The N-terminus and C-terminus of a peptide is not in the R-group (known in the art) of any amino acid that made up the peptide. Alkyl group for the purpose of this invention is a chemical group that is made up of only carbon and hydrogen. The preferred alkyl group in this invention contains 6 to 36 carbon units with their covalently linked hydrogen atoms.

Peptide analogs can be generated using standard techniques of peptide chemistry and can be assessed for activity either before or after incubation in serum. Particularly preferred peptides analogs of the invention are those peptides containing 1) an alkyl group of 6-36 carbon units at the N- or C-terminus of a linear peptide; or 2) iminodiacetic acid, which may or may not be a portion of nitrilotriacetic acid. The analogs can have a general formula: A-$(Gly)_x$-peptide (SEQ ID NO: 54) or peptide-$(Gly)_x$-A (SEQ ID NO: 55), wherein the left side of the peptide is N-terminal and the right side is C-terminal; Gly is Glycine; where x is an integer from 0-5; A can be any chemical group or moiety containing an alkyl group with 8 to 36 carbon units, a nitrilotriacetic acid group, a imidodiacetic acid group, or $(His)_y$ (SEQ ID NO: 51); where y is an integer from 2-6. The peptide can be any sequence or chain of 5-100 amino acids. The amino acids can be any of the 20 naturally occurring amino acids or their derivatives. The attachment of A to the peptide may involve simple linker group such as lactate or glycine. Lactate is especially important if we want to attach the alkyl group using an ester bond to the amino terminus of a peptide. To attach an alkyl group to the carboxyl terminus of a peptide by amide bond, an amino-alkyl group will be used with the general formula $CH_3(CH)_n$—NH—; where n=5-34.

Analogs of peptides exemplified by vasopressin can be generated using standard techniques of peptide chemistry and can be assessed for calcium influx activity before and after incubation in serum, all according to the guidance provided herein. Preferred analogs of the invention are those based upon the sequence of vasopressin, as follows:

```
                                      (SEQ ID NO: 56)
A-Gly-Gly-Gly-Cys-Tyr-Phe-Gln-Asn-Cys-Pro-B-C-D
``` wherein:
A is selected groups containing alkyl group with 3 to 36 carbon units, nitrilotriacetic acid, imidodiacetic acid or $(Z_xHis_y)_p$ (SEQ ID NO: 50); where Z is an amino acid residue, His is histidine, x is an integer from 0-6; y is an integer from 1-6; and p is an integer from 1-6;
Gly is Glycine
Cys is Cystine or Cysteine
Tyr is Tyrosine
Phe is Phenylalanine
Gln is Glutamine
Asn is Aspargine
Pro is proline
B is Lysine or Arginine
C is Glycine or Alanine
D is $NH_2$ or H
A-Gly-Gly-Gly- subunit is covalently attached to any available amino group of the peptide by an amide bond.

Many of the protected amino acid residues useful in synthesizing the preferred compounds of this invention are commercially available from many amino acid suppliers. Furthermore, all the peptide analogs that are the subject of the present invention can be synthesized by outside custom peptide providers such as Anaspec, San Jose Calif. USA, Polypeptide laboratories, Torrance, Calif., or ChemPep Inc, Miami, Fla. Synthesis of peptides according to the specification disclosed in this application can easily be done by those skilled in the art and preferably done using solid phase synthesis, especially if the modification is at a terminal residue of the peptides. For peptide with nitrilotriacetic acid at the carboxyl terminal (FIG. 20), the nitrilotriacetic acid derivative such as [N',N', bis(carboxymethyl)-lysine] that is protected at the N-terminal (by Fmoc or Boc, as known in the art) is first immobilized or conjugated with the resin where the remaining unreacted carboxyl group can be protected if desired. The activated carboxyl group of the protected incoming amino acid will then be conjugated to the amino group of immobilized N',N', bis(carboxymethyl)-lysine after Fmoc or Boc removal and the synthesis continues as normal solid phase peptide synthesis. The cleavage from the resin, deprotection and purification is similar to conventional peptide synthesis with an extra option in the purification step of using metal affinity chromatography to purify. For peptide with iminodiacetic acid at the carboxyl terminus (FIG. 21), the iminodiacetic acid is first N-protected by Fmoc or Boc and then immobilized or conjugated with the resin through its carboxyl group and the second unreacted carboxyl group can be protected if desired. The incoming activated carboxyl group of the protected amino acid will then be conjugated to the secondary amino group of immobilized iminodiacetic acid (after Fmoc or Boc removal or deprotection) and the synthesis continues as normal solid phase peptide synthesis. For peptide with iminodiacetic acid at the amino terminus (FIGS. 19 and 22), the synthesis continues as normal solid phase peptide synthesis and at the last amino acid residue, activated nitrilotriacetic acid is conjugated to the amino terminus of the growing chain. The activation of nitrilotriacetic acid can be limited to one carboxyl per nitrilotriacetic acid, however this is not necessary from our experience as excess of fully activated and N-protected nitrilotriacetic acid reacts only to one terminal amino group. The cleavage from the resin, deprotection and purification is similar to conventional peptide synthesis with an extra option in the purification step of using metal affinity chromatography to purify.

Once the desired analogs of peptides has been synthesized, cleaved from the resin and fully deprotected, the peptide is then purified to ensure the recovery of a single oligopeptide having the selected amino acid sequence with the desired functional group. Purification can be achieved using any of the standard approaches, which include reversed-phase high-pressure liquid chromatography (RP-HPLC) on alkylated silica columns, e.g. $C_{4-18}$ silica. Such column fractionation is generally accomplished by running linear gradients, e.g., 10-90%, of increasing % organic solvent, e.g., acetonitrile, in aqueous buffer, usually containing a small amount (e-g., 0.1%) of pairing agent such as TFA or TEA. Alternatively, ion-exchange HPLC can be employed to separate peptide species on the basis of their charge characteristics. Column fractions are collected, and those containing peptide of the desired/required purity are optionally pooled with the guide of Tandem Mass spectrometry detector. In one embodiment of the invention, the vasopressin peptide is then treated in the established manner to exchange the cleaving acid (e.g., TFA) with a pharmaceutically acceptable acid anion and to allow intra-molecular disulfide bridge formation in dilute solution under a suitable oxidizing agent. This intra-molecular disulfide bridge formation can be confirmed by HPLC/MS analysis.

B. Binding Moieties

The present disclosure provides binding moieties of hydrophobic or metal binding groups that can be attached to the peptides and the polymeric carrier molecules of the embodiments that permit reversible binding to polymeric carrier to form the peptide complexes.

1. Hydrophobic Groups

In one aspect, the binding moiety of the modified peptide is a hydrophobic group, e.g., an alkyl group of 6 to 36 carbon units. Such hydrophobic groups can non-covalently bind to hydrophobic groups in a carrier molecule. In one embodiment, the alkyl group of the binding moiety is a linear alkyl carbonyl group having a formula $CH_3(CH_2)_n$—CO—, where n is an integer between 4-34, or a corresponding amino-alkyl group with 6 to 36 carbon units wherein the respective alkyl groups can be attached to the N- or C-terminus of the peptide or to a side chain of an amino acid of the peptide. In another embodiment, the alkyl group of the binding moiety is a branched alkyl carbonyl group or a branched amino-alkyl group with 6-36 carbon units attached, respectively, to the N- or C-terminus of the peptide or to a side chain of an amino acid of the peptide. The hydrophobic groups can also be ring compounds of 6-36 carbon units.

2. Metal Binding Groups

In another aspect, the present disclosure provides binding moieties with a metal binding domain, such as those disclosed in U.S. patent application Ser. No. 11/112,879, which is incorporated herein by reference, in its entirety.

The metal binding moiety can be any conformational arrangement of several chemical groups that is capable of forming a complex between the metal ion and the chemical groups by coordinate bonds. In certain embodiments, the metal binding moiety is a chelating group. Chelating groups posses a pair of unpaired electrons that are available for coordinate bonding with a metal ion. Bidentate-, tridentate- and tetradentate chelating groups are well known in the art.

In one embodiment, a plurality of metal binding moieties with chelated metal ion are covalently attached to the core polymer of the polymeric carrier, a metal binding moiety is covalently to the peptide which forms a reversible coordinate bond to the metal ion. In general, the metal binding domains of the metal binding moieties used in the present invention contain a Lewis base fragment that is contemplated to encompass numerous chemical moieties having a variety of structural, chemical and other characteristics capable of forming coordination bonds with a metal ion. The types of functional groups capable of forming coordinate complexes with metal ions are known to those of skill in the art. For example, such moieties will generally include functional groups capable of interaction with a metal center, e.g., heteroatoms such as nitrogen, oxygen, sulfur, and phosphorus. Metal cations are almost always Lewis acidic and are therefore able to bind various moieties that may serve as Lewis bases. In preferred embodiments, the metal chelate ions include, but are not limited to, $Zn^{2+}$, $Ni^{2+}$, $Co^{2+}$, $Fe^{2+}$, $Mn^{2+}$, and $Cu^{2+}$.

In general, a moiety serving as a Lewis base will be a strongly acidic group, e.g., with a pKa less than about 7, and more preferably less than 5, which may produce a conjugate base that, under the appropriate conditions, is a strong enough Lewis base to donate an electron pair to a metal ion to form a coordinate bond. The degree of this Lewis acid-to-Lewis base interaction is a function not only of the particular metal ion, but also of the coordinating moiety itself, because the latter may vary in the degree of basicity as well as in size and steric accessibility. Exemplary Lewis basic moieties which may be included in the metal binding domain include: amines (primary, secondary, and tertiary) and aromatic amines, amino groups, amido groups, nitro groups, nitroso groups, amino alcohols, nitriles, imino groups, isonitriles, cyanates, isocyanates, phosphates, phosphonates, phosphites, phosphines, phosphine oxides, phosphorothioates, phosphoramidates, phosphonamidites, hydroxyls, carbonyls (e.g., carboxyl, ester and formyl groups), aldehydes, ketones, ethers, carbamoyl groups, thiols, sulfides, thiocarbonyls (e.g., thiolcarboxyl, thiolester and thiolformyl groups), thioethers, mercaptans, sulfonic acids, sulfoxides, sulfates, sulfonates, sulfones, sulfonamides, sulfamoyls and sulfinyls.

Illustrative of suitable metal binding domains include those chemical moieties containing at least one Lewis basic nitrogen, sulfur, phosphorous or oxygen atom or a combination of such nitrogen, sulfur, phosphorous and oxygen atoms. The carbon atoms of such moiety may be part of an aliphatic, cycloaliphatic or aromatic moiety. In addition to the organic Lewis base functionality, such moieties may also contain other atoms and/or groups as substituents, such as alkyl, aryl and halogen substituents. Preferred binding moieties are nitrilotriacetic acid and iminodiacetic acid groups, or his tags that consist of two to six linked histidine residues (SEQ ID NO: 51).

In one embodiment, the metal binding moiety of the peptide analog is attached by a covalent amide bond to the N-terminus of the peptide. In another embodiment, the metal binding moiety of the peptide analog is covalently attached by a covalent amide bond to the C-terminus of the peptide. In another embodiment, the metal binding of the peptide analog is attached by a covalent bond to a side chain of an amino acid of the peptide. In further embodiments, a cleavable moiety is covalently bound and positionally located between the metal binding moiety and the peptide. In exemplary embodiments, the metal binding moiety is a his tag with cleavable moiety of the formula His-His-His-His-His-His-Gly-Gly-Gly (SEQ ID NO: 6), wherein the moiety is bound to either the N-terminus, or to the C-terminus, or to a side chain of an amino acid of the peptide. In a further embodiment, the metal binding moiety is a moiety of formula $(Z_y His_w)_p$ (SEQ ID NO: 50), wherein Z is an amino acid residue other than histidine, y is an integer from 0-6, w is an integer from 1-6, and p is an integer from 1-6, and is bound to a cleavable moiety. In another embodiment, the metal binding moiety is nitrilotriacetic acid and is bound to a cleavable moiety, e.g., $Gly_3$, and the peptide. In another embodiment, the metal binding moiety is iminodiacetic acid and is bound to a cleavable moiety, e.g., $Gly_3$, and the peptide.

In certain embodiments, if peptide is GLP, A is attached to the peptide at a position other than the amino terminus.

Other chelating groups include 1,4,7,10-tetraaza-cyclododecane-N,N',N''-triacetic acid; 1,4,7-tris(carboxymethyl)-10-(2'-hydroxypropyl)-1,4,7,10-tetraazocyclodecane, 1,4,7-triazacyclonane-N,N',N''-triacetic acid; and 1,4,8,11-tetraazacyclotetra-decane-N,N',N'',N'''-tetra acetic acid; diethylenetriamine-pentaacetic acid (DTPA); triethylenetetraamine-hexaacetic acid; ethylenediamine-tetraacetic acid (EDTA); EGTA; 1,2-diaminocyclohexane-N,N,N',N'-tetraacetic acid but preferably N-(hydroxyethyl)ethylenediaminetriacetic acid; nitrilotriacetic acid (NTA); and ethylene-bis(oxyethylene-nitrilo)tetraacetic acid, histidine, cysteine, oligoaspartic acid, oligoglutamic acid, S-acetyl mercaptoacetate and meractoacetyltriglycine.

3. Cleavable Moiety

The present disclosure provides cleavable moieties that serve as linkers between the biologically active peptide and the binding moiety. The cleavable moiety may include an amino acid sequence that can serve as a substrate for a protease, usually an extracellular protease. In one embodiment, the binding moiety is attached to the peptide through a polyglycine cleavable moiety, such as Gly-Gly-Gly. In another embodiment, the binding moiety comprises one or more cysteine residues capable of forming a disulfide bond with corresponding cysteine residues incorporated into the polymeric carrier, which can be cleaved by action of a reducing agent. In such embodiments, cleavage of the cleavable moiety in the body releases the peptide from the polymeric carrier. The cleavable moiety may be $(Gly)_x$ groups (SEQ ID NO: 58) and include, without limitation, $Gly_2$, $Gly_3$, $Gly_4$ (SEQ ID NO: 63), $Gly_5$ (SEQ ID NO: 64) and $Gly_6$ (SEQ ID NO: 65). The cleavable moiety may also be $(Ala)_x$ groups (SEQ ID NO: 59) and include without limitation $Ala_2$, $Ala_3$, $Ala_4$ (SEQ ID NO: 66), $Ala_5$ (SEQ ID NO: 67) and $Ala_6$ (SEQ ID NO: 68). The cleavable moiety may also be $(Lys)_x$ groups (SEQ ID NO: 60) and include without limitation $Lys_2$, $Lys_3$, $Lys_4$ (SEQ ID NO: 69), $Lys_5$ (SEQ ID NO: 70) and $Lys_6$ (SEQ ID NO: 71). The cleavable moiety may also be $(Arg)_x$ groups (SEQ ID NO: 61) and include without limitation $Arg_2$, $Arg_3$, $Arg_4$ (SEQ ID NO: 72), $Arg_5$ (SEQ ID NO: 73) and $Arg_6$ (SEQ ID NO: 74). The cleavable moiety may also be $(Ala-Arg)_n$ groups (SEQ ID NO: 62), where n is between 1-3. The cleavable moiety may also be a moiety of formula $(N)_q$-Arg, wherein N is any amino acid and q is 0 or 1. The cleavable moiety may also be a moiety of formula Arg-$(N)_q$, wherein N is any amino acid and q is 0 or 1. The cleavable moiety may also be a moiety of formula Lys-$(N)_q$, wherein N is any amino acid and q is 0 or 1. The cleavable moiety may also be a sequence of two amino acids in which one is Arg or Lys. Alternatively, the cleavable moiety may be any one from a group consisting of Ile-His-Pro-Phe-His-Leu-Val-Ile-His-Thr (SEQ ID NO: 7); Leu-Ala-Gln-Ala-Val-Arg-Ser-Ser-Ser-Arg (SEQ ID NO: 8); Glu-Arg-Nle-Phe-Leu-Ser-Phe-Pro (SEQ ID NO: 9); Ser-Gln-Asn-Tyr-Pro-Ile-Val-Gln (SEQ ID NO: 10); Arg-Gly-Val-Val-Asn-Ala-Ser-Ser-Arg-Leu-Ala (SEQ ID NO: 11); Glu-Val-Asn-Leu-Asp-Ala-Phe-Lys (SEQ ID NO: 12); Glu-Val-Asn-Leu-Asp-Ala-Glu-Phe-Lys (SEQ ID NO: 13); Glu-Val-Lys-Val-Asp-Ala-Glu-Phe-Lys (SEQ ID NO: 14); His-Gln-Lys-Leu-Val-Phe-Phe-Ala-Lys (SEQ ID NO: 15); Lys-Thr-Glu-Glu-Ile-Ser-Glu-Val-Asn-Leu-Asp-Ala-Glu-Phe (SEQ ID NO: 16); Glu-Val-His-His-Gln-Lys-Leu-Val-Phe-Phe-Ala-Glu (SEQ ID NO: 17); Pro-Gln-Gly-Leu-Glu (SEQ ID NO: 18); Arg-Pro-Lys-Pro-Val-Glu-Nva-Trp-Arg-Lys (SEQ ID NO: 19); Arg-Pro-Lys-Pro-Tyr-Ala-Nva-Trp-Met-Lys (SEQ ID NO: 20); Pro-Leu-Ala-Tyr-Trp-Ala-Arg (SEQ ID NO: 21); Arg-Pro-Leu-Ala-Leu-Trp-Arg-Ser (SEQ ID NO: 22); Arg-Pro-Lys-Pro-Leu-Ala-Nva-Trp-Lys (SEQ ID NO: 23); Pro-Tyr-Ala-Tyr-Trp-Met-Arg (SEQ ID NO: 24); Pro-Leu-Gly-Met-Trp-Ser-Arg (SEQ ID NO: 25); Pro-Leu-Ala-Leu-Trp-Ala-Arg (SEQ ID NO: 26); Pro-Leu-Gly-Leu-Trp-Ala-D-Arg (SEQ ID NO: 27); Asp-Glu-Val-Asp (SEQ ID NO: 28); Asp-Met-Gln-Asp (SEQ ID NO: 29); Leu-Glu-Val-Asp (SEQ ID NO: 30); Val-Glu-Ile-Asp (SEQ ID NO: 31); Ile-Glu-Thr-Asp (SEQ ID NO: 32); and Leu-Glu-His-Asp (SEQ ID NO: 33).

II. Polymeric Carrier

The polymeric carrier of the present invention include polymers and co-polymers of linear or branched structure or conjugates thereof, micelles, emulsions, colloids and solid surfaces, where the polymers may in addition self-organize in supramolecular structures including at least two polymers. The copolymers include as one of the main polymeric elements a backbone core polymer that contains a hydrophobic binding group or a metal binding group and, in certain embodiments, protective side chains, such as PEG or mPEG.

The backbone can be a linear polymer, such as a polyamino acid; e.g., a homopolymer or a nucleic acid, or a branched polymer, such as a carbohydrate. In one example, a polymeric carrier composition of the present invention comprises the backbone linear homopolyamino acid core with a degree of polymerization in the range of 2-10,000 to which independently and covalently linked are polyglycol protective side chains, and chelating groups, where said chains and chelating groups are independently linked to the backbone core polymer. In another example, the degree of polymerization of the backbone core is in the range of 100-1,000. In still another example, the degree of polymerization is in the range of 100 to 300. Examples of polymeric backbone cores include carboxylated or carboxymethylated linear poly-1-lysine (PL) or poly-D-lysine, carboxylated or carboxymethylated poly-alpha,beta-(2-aminoethyl)-D,L-aspartamide; poly-aspartic acid, poly-glutamic acid, copolymers of histidine with positively or negatively charged aminoacids, carboxylated polyethyleneimines, i.e., polyethylene imines reacted with derivatives of carbonic acids. In preferred embodiments, the backbone linear core comprises poly-lysine.

In another embodiment, the polymeric carrier further comprises protective side chains. In one embodiment, the protective side chain comprises polyethylene glycol (PEG). In a further embodiment, the protective side chain comprises alkoxy polyethylene glycol. In a further embodiment, the protective side chain comprises methoxy polyethylene glycol (MPEG). The protective side chains of the embodiments will have a mass of between 200 and 60,000 Daltons independent of the polymeric core weight, preferably a mass of between 1000 and 40,000 Daltons, and more preferably between 2,000 and 20,000 Daltons.

The metal binding domains of the polymeric carrier may include polycarboxylic acids containing nitrogen where at least one of carboxylic groups may be utilized for covalent linking of the chelate to the carrier backbone polymer component of the composition of the invention. The addition of said metal ions to chelates included in the polymeric carrier compositions of the invention either at room temperature or at elevated temperatures results in the formation of coordinate complexes (metal-chelates). These metal-chelate complexes bind to the metal binding domain of peptide, added either in a purified state or in the presence of bulk protein or blood plasma proteins, with the formation of peptide complex compositions containing coordinate complexes formed between the metal-chelate of the polymeric carrier and the peptides. The amino acid sequence of the peptides of the invention may include one or more histidines or cysteines which increase the stability of the complex formed between the peptide and polymeric carrier metal-chelate complexes.

Hydrophobic binding moieties attached to the carrier can include an alkyl group. In a further embodiment, the alkyl group comprises a linear or branched alkyl group. In a further embodiment, the alkyl group can be at least partially saturated. In a further embodiment, the alkyl group comprises an ethyl or propyl group. In a further embodiment, the alkyl group is a butyl, pentyl, or hexyl group. In a further embodiment, the alkyl group is $CH_3(CH_2)_nCH_2$—, $CH_3(CH_2)_nCH_2NH$—, $CH_3(CH_2)_nCO$—, $CH_3(CH_2)_nCH_2O$—, $CH_3(CH_2)_nCH_2S$—, $—OC(CH_2)_nCH_2$—, $—OC(CH_2)_nCH_2NH$—, $—OC(CH_2)_nCO$—, $—OC(CH_2)_nCH_2O$—, $—OC(CH_2)_nCH_2S$—, $—HNC(CH_2)_nCH_2$—, $—HNC(CH_2)_nCH_2$—, $—HNC(CH_2)_nCH_2NH$—, $—HNC(CH_2)_nCO$—, $—HNC(CH_2)_nCH_2O$—, $—HNC(CH_2)_nCH_2S$—, $—OCH_2(CH_2)_nCH_2$—, $—OCH_2(CH_2)_nCH_2NH$—, $—OCH_2(CH_2)_nCO$—, $—OCH_2(CH_2)_nCH_2O$—, or $—OCH_2(CH_2)_nCH_2S$— group, wherein "n" is 4-34, inclusive. In a further embodiment the present the hydrophobic chain is $—(CH_2)_4NHCO(CH_2)_nOC$-A-$OR_3$, $—(CH_2)_4NHCO(CH_2)_nNHCO(CH_2)_yCO$-A-$OR_3$, $—CH_2OOC(CH_2)_nOC$-A-$OR_3$, $—CH_2OOC(CH_2)_nNHCO(CH_2)_yCO$-A-$OR_3$, $—CH(CH_3)OOC(CH_2)_nOOC$-A-$OR_3$, $—CH(CH_3)OOC(CH_2)_nNHCO(CH_2)_yCO$-A-$OR_3$, $—CH_2COOC(CH_2)_nCO$-A-$OR_3$, $CH_2COOC(CH_2)_nNHCO(CH_2)_yCO$-A-$OR_3$, $—CH_2CONH(CH_2)_nNHCOCH_2CH_2$-A-$OR_3$, $—CH_2CONH(CH_2)_nNHCO(CH_2)_yCO$-A-$OR_3$, $—(CH_2)_2COOC(CH_2)_nCO$-A-$OR_3$, $—(CH_2)_2COOC(CH_2)_nNHCO(CH_2)_yCO$-A-$OR_3$, $—(CH_2)_2CONH(CH_2)_nNHCOCH_2CH_2$-A-$OR_3$, $—(CH_2)_2CONH(CH_2)_nNHCO(CH_2)_yCO$-A-$OR_3$, $—(C_6H_4)OCO(CH_2)_nCO$-A-$OR_3$, and $(C_6H_4)OCO(CH_2)_nNHCO(CH_2)_yCO$-A-$OR_3$, wherein n is 2-22; y is 2-6; $R_3$ is H, $(CH_2)_pCH_3$ or $(CH_2)_pCOOH$, wherein p is 0-7; and A is $[OCH_2CH_2]_x$ or $[OCHCH_3CH_2]_x$, wherein x is 17-250, or various combinations of $[OCH_2CH_2]$ or $[OCHCH_3CH_2]$ with a total of 17-250 units. In another embodiment, the hydrophobic group comprises an aromatic ring compound. In a further embodiment, the aromatic ring is phenyl. In a further embodiment, the aromatic ring is naphthyl. In a further embodiment, the aromatic ring compound is cholesterol. In a further embodiment, the aromatic ring compound is fluorescein and the carboxyl group in fluorescein will act as orienting molecule.

The percent load capacity of the polymeric carrier for the peptide analog can vary, depending on the respective compositions of the carrier and the peptide analog. In one embodiment, the peptide analogs of the present invention are complexed with the polymeric carrier compounds by dissolving or suspending one hundred mg of the polymeric carrier in an appropriate solvent; e.g., phosphate buffered saline, saline, acetate buffer, water or other appropriate solvent known in the art to be compatible for parenteral drug administration, and mixing with 1-200 mg of peptide analog of the present invention in a final unit volume of 100 µl to 1 ml until the peptide analog is bound to the carrier. The resulting formulation can be lyophilized for later reconstitution in appropriate volume for administration to a patient. The formulation can also be filter sterilized prior to lyophilization or prior to administration to a patient. Alternatively the carrier can be filter sterilized by passing through a filter (0.10 µm to 0.22 µm filter) prior to mixing with a peptide analog of the present invention that has been sterilized in similar manner.

III. Peptide Formulations

For administration to patients, the peptide complex compositions are provided in a pharmaceutically acceptable form. In one embodiment, the vasopressin analog peptide or its salt is provided in a pharmaceutically acceptable vehicle as a preparation that is sterile-filtered, e.g., through a 0.22 µm filter, and is substantially pyrogen-free. Desirably, the vasopressin analog peptide to be formulated migrates as a single or individualized peak on HPLC, exhibits uniform and authentic amino acid composition and sequence upon analysis thereof, and otherwise meets standards set by the various national bodies which regulate quality of pharmaceutical products. The analogs with alkyl group of 6-36 carbon units can form micelle and can be administered in a suitable solvent. Alternatively, the analogs with alkyl group of 6-36 carbon units can be incorporated into a carrier with hydrophobic core such as those described in U.S. patent application Ser. No. 11/613,183. Alternatively, the alkyl containing analogs may be incorporated into micelles or liposomes. The analogs with 2-6 histidine residue (SEQ ID NO: 51) can be incorporated into metal containing carriers such as those described in U.S. Pat. No. 7,138,105. These carriers will further prolong the blood circulation half-life of these analogs by preventing their rapid activation which would be followed by rapid elimination from the blood.

For therapeutic use, the chosen vasopressin- or other peptide-analog is formulated with a carrier (such as those described in U.S. Pat. No. 7,138,105 and U.S. application Ser. No. 11/613,183, herein incorporated by reference) and/or other pharmaceutically acceptable diluents or excipients that is appropriate for delivering the peptide by the chosen route of administration. Other suitable pharmaceutically acceptable diluents or excipients are those used conventionally with peptide-based drugs. Reference may be made to Remington's Pharmaceutical Sciences", 17th Ed., Mack Publishing Company, Easton, Pa., 1985, for guidance on drug formulations generally. In one embodiment of the invention, the compounds are formulated for administration by infusion or by injection, e.g., sub-cutaneously, intramuscularly or intravenously, and are accordingly utilized as aqueous solutions in sterile and pyrogen-free form and optionally buffered to physiologically tolerable pH, e.g., a slightly acidic or physiological pH. Thus, the compounds may be administered in a vehicle such as distilled water or, more desirably, in saline, phosphate buffered saline or 5% dextrose solution. Water solubility of the vasopressin/or other peptides analogs, especially those with alkyl group, may be enhanced, if desired, by incorporating a solubility enhancer. The vasopressin/ or other peptide analogs of the invention may also be formulated as a slow release implantation device to further extend the duration of action. Examples of such sustained release formulations include composites of biocompatible polymers, such as poly(lactic acid), poly(lactic-co-glycolic acid), methylcellulose, hyaluronic acid, collagen, and the like, preferably with covalently attached hydrophobic moiety or metal chelates. The structure, selection and use of degradable polymers in drug polymeric carriers have been reviewed in several publications, including, A. Domb et al., Polymers for Advanced Technologies 3:279-292 (1992). Additional guidance in selecting and using polymers in pharmaceutical formulations can be found in the text by M. Chasin and R. Langer (eds.), "Biodegradable Polymers as Drug Delivery Systems, Vol. 45 of "Drugs and the Pharmaceutical Sciences," M. Dekker, New York, 1990. Liposomes may also be used to further sustain the action of vasopressin analogs. Details concerning how to use and make liposomal formulations of drugs of interest can be found in, among other places, U.S. Pat. No 4,944,948; U.S. Pat. No. 5,008,050; U.S. Pat. No. 4,921,706; U.S. Pat. No. 4,927,637; U.S. Pat. No. 4,452,747; U.S. Pat. No. 4,016,100; U.S. Pat. No. 4,311,712; U.S. Pat. No. 4,370,349; U.S. Pat. No. 4,372,949; U.S. Pat. No. 4,529,561; U.S. Pat. No. 5,009,956; U.S. Pat. No. 4,725,442; U.S. Pat. No. 4,737,323; U.S. Pat. No. 4,920,016. In one embodiment of the invention, the package contains the vasopressin/or other peptide analog (similarly altered as vasopressin analogs) with or without additional carrier, diluent and excipients as an administration-ready formulation. Alternatively, and according to another embodiment of the invention, the package provides the vasopressin/ or peptide analog with or without carrier in a form, such as a lyophilized form, suitable for reconstitution in a suitable diluent or excipients, such as phosphate-buffered saline. In one embodiment, the package is a sterile-filled vial or ampoule containing an injectable solution which comprises an effective, active amount of vasopressin/or other peptide analog dissolved in an aqueous vehicle. As an alternative to injectable formulations, the vasopressin/or other peptide analog may be formulated for administration by other routes. Oral dosage forms, such as tablets, capsules and the like, can be formulated in accordance with standard pharmaceutical practice.

IV. Methods of Use

The novel compositions disclosed herein can be selected for use in methods of treatment of patients according to the combinations of peptide analogs and polymeric carriers provided and the underlying disease or physiologic condition of the patient and/or the molecular target and its location. The peptide analog compositions can be administered by any suitable means or route, including parenteral, intrapulmonary, and intranasal, and, if desired, for local injection. Parenteral administration routes include intramuscular, intravenous, intraarterial, intraperitoneal, or subcutaneous administration.

The appropriate dosage of peptide analog will depend on the type of disease or condition to be treated, the severity and course of the disease, the patient's clinical history and response to the peptide analog, and the discretion of the attending physician. Peptide analogs can suitably be administered to the patient in a single dose, in divided doses, or over a series of treatments. Also, the present invention contemplates mixtures of more than one peptide analog, as well as use in combination with other therapeutic agents.

In certain embodiments, the dosage of the subject compounds will generally be in the range of about 0.01 ng to about 1 g per kg body weight, specifically in the range of about 1 ng to about 0.1 g per kg, and more specifically in the range of about 100 ng to about 10 mg per kg.

The peptide analog and polymeric carrier compositions will be formulated, dosed, and administered in a fashion consistent with good medical practice. Factors for consideration in this context include the particular disorder being treated, the particular mammal being treated, the clinical condition of the individual patient, the cause of the disorder, the site of delivery of the peptide, the method of administration, the scheduling of administration, and other factors known to medical practitioners. The "therapeutically effective amount" of a peptide composition and polymeric carrier complex to be administered will be governed by such considerations, and is the minimum amount necessary to prevent, ameliorate, or treat a disease or disorder.

The precise time of administration and dosage of any particular compound that will yield the most effective treatment in a given patient will depend upon the activity, pharmacokinetics, and bioavailability of a particular compound, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation or will consist of monitoring the subject and adjusting the dosage and/or timing. An effective dose or amount, and any possible affects on the timing of administration of the dose, may need to be identified for any particular composition of the present invention. Dosages for the compounds of the present invention may be readily determined by techniques known to those of skill in the art. In one embodiment, the effective dose may be determined by routine experiment using one or more groups of animals (preferably at least 5 animals per group), or in human trials if appropriate. In another embodiment, the effectiveness of the composition and method of treatment or prevention may be assessed by administering the peptide analog and assessing the effect of the administration by measuring one or more indices associated with the disease or condition of interest, and comparing the post-treatment values of these indices to the values of the same indices prior to treatment. For repeated administrations over several days or longer, depending on the condition, the treatment is sustained until a desired suppression of disease symptoms occurs. Accordingly, the method of treatment embodiments can include obtaining single or sequential blood or other body fluid samples from a patient after administration of the composition and quantitatively assaying for the free peptide by use of assays known in the art; e.g., HPCL, bioassay, mass spectronomy and the like. Resulting values can be compared to threshold values known in the art to correspond to therapeutically-effective concentrations; e.g., area under the curve (AUC), half-life, Cmax, and other pharmacokinetic parameters known in the art.

Generally, alleviation or treatment of a disease or disorder involves the lessening of one or more symptoms or medical problems associated with the disease or disorder. Thus, one embodiment of the invention relates to a method of use of novel long-acting vasopressin peptide analogs in sustained release polymeric carrier complexes administered to a patient to increase blood perfusion to various organs in hypovolemic and hypotensive condition and/or increase the level of factor VIII and plasminogen activator in the blood. Exemplary disease or physiologic conditions in which the methods of treatment using the vasopressin peptide analogs of the present disclosure would have utility include, but are not limited to, hypovolemia, splanchnic vasodilation, systemic vasodilation, hypotension, esophageal variceal hemorrhage, hepatorenal syndrome (HRS), type 1 HRS, type 2 HRS, sepsis, liver cirrhosis, portal vein hypertension, esophageal varices, paracentesis-induced circulatory dysfunction, arterial hypotension induced by byproducts of bacteria, anesthesia-associated hypotension, cardiac arrest, and post-partum hemorrhage. Under these conditions a long acting vasoconstrictor such as the vasopressin analogs of the invention will be beneficial for these patients.

In another embodiment, the invention related to a method of use of novel GLP peptide analog compositions. In preferred embodiments, the compositions are GLP-1 analogs with insulinotropic activity. The term "insulinotropic activity" relates to the ability of a substance to stimulate, or cause the stimulation of, the synthesis or expression of the hormone insulin. Thus, one embodiment of the invention relates to administration of novel long-acting GLP-1 analogs in sustained release polymeric carrier complexes to a patient to increase insulin levels in a patient, with concomitant reductions in circulating glucose levels. In one embodiment, the insulinotropic property of the GLP-1 analogs may be determined by administering the analog to a patient and monitoring the release of immunoreactive insulin (IRI) into the circulatory system. The presence of IRI is detected through the use of a radioimmunoassay which can specifically detect insulin or by other methods known in the art. In another embodiment, the therapeutic efficacy of the GLP-1 analogs can be determined by monitoring effects on circulating glycemic variables on single, repeated, or post-prandial or post-glucose-load blood samples and comparing the concentrations to values known in the art to correspond to normal glucose tolerance, impaired glucose tolerance, or diabetes-associated values for fasting and postload glucose and insulin, glycosylated hemoglobin (HbAlc), lipids, as well as insulin resistance parameters. In another embodiment, the invention related to a method of use of compositions of GLP-2 analogs having therapeutic utility in the treatment of diseases of the gastrointestinal tract. In particular, the GLP-2 analogs can act as trophic agents to enhance and maintain the functioning of the gastrointestinal tract and to promote growth of intestinal tissue. The methods and formulations of the present invention preferably provide about 0.1 to about 50 mg/ml of GLP-2 or a biologically active fragment thereof, preferably about 5 to about 40 mg/ml, more preferably about 7 to about 30 mg/ml, even more preferably about 10 to about 20 mg/ml, and most preferably about 20 mg/ml.

The invention may be better understood with reference to the following examples. These examples are intended to be representative of specific embodiments of the invention, and are not intended as limiting the scope of the invention as any peptide can be altered similarly as alteration made to vasopressin and the similar slow activation is expected to be observed on the presence of serum. Occasionally modified peptide depending on the peptide may be active after modification such as GLP-1 modification proposed here (Example 9; FIGS. 20 and 21).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

EXAMPLES

Example 1

The synthesis of $CH_3(CH_2)_{10}CO$-Gly-Gly-Gly-Cys-Tyr-Phe-Gln-Asn-Cys-Pro-Lys-Gly-$NH_2$ (SEQ ID NO: 34) (also referred to as C12TerA which is a lysine vasopressin analog) with disulfide bonds between the two cysteine residues (Cys4 and Cys9) was done by Anaspec, San Jose, Calif., according to the inventor's specification. The known standard amino acids in the formula above are represented by three letter abbreviations know to those skilled in the art (See FIG. 2 for complete chemical formula). In this lysine vasopressin analog, lauric acid was attached to the N-terminal aminogroup of the peptide via amide bond formed between the carboxyl group of lauric acid and the amino group of glycine residue of the peptide. The known standard amino acids in the formula above are represented by three letter abbreviations known to those skilled in the art. At the end of the synthesis the determined molecular mass was found to be 1409.5 Da corresponding to protonated peptide or the molecular ion peak on mass spectroscopic analysis. This was consistent with the theoretical molecular mass of 1410.4 Da when protonated. This peptide was a white powder with limited solubility in water and was easily obtained at purity of greater than 90% in this case. This peptide can form micelle in water (see FIG. 10), which protects the peptide from rapid activation into vasopressin (see Table 1) and eventual inactivation. As can be seen in FIGS. 11 and 12, after incubation in serum for 2 hours vasopressin analog (C12TerA) was able to induce calcium influx in human umbilical endothelial cell culture indicating the presence of biological activity. Addition of alkyl group (C12) to the peptide gives it a longer biological activity than the native vasopressin (lysine vasopressin or arginine vasopressin) or the other long acting analog such as terlipressin (see FIG. 1 and Table 1). In addition to forming micelle, this vasopressin analog can be loaded (see FIGS. 17 and 18) into a polymeric drug carriers containing hydrophobic group such as that described in U.S. patent application Ser. No. 11/613,183, which is hereby incorporated by reference.

Example 2

The synthesis of $CH_3(CH_2)_{10}CO$—$OHC(CH_3)CO$-Gly-Gly-Gly-Cys-Tyr-Phe-Gln-Asn-Cys-Pro-Lys-Gly-$NH_2$ (SEQ ID NO: 35) (also referred to as C12TerE) with disulfide bonds between the two cysteine residues (Cys4 and Cys9) was done by custom peptide supplier Anaspec, San Jose, Calif., according to the inventor's specification. The known standard amino acids in the formula above are represented by three letter abbreviations know to those skilled in the art (see FIG. 3 for complete chemical formula). In this structure the 12 carbon alkyl group was attached to the hydroxyl group of lactate which was attached to the amino terminus of the peptide via amide bond through its carboxyl group. This provides a hydrolysable ester bond which is believed to be less stable than amide bond and will facilitate the removal of the 12 carbon fatty acid. At the end of the synthesis the determined molecular mass was found to be 1481.6 Da, corresponding to protonated peptide or the molecular ion peak on mass spectroscopic analysis. This is consistent with the theoretical molecular mass of 1482.5 Da when protonated. This peptide was off-white powder with limited solubility in water and was easily obtained at purity of greater than 90% in this case. This peptide can form micelle (FIG. 10) in water, which protects the peptide from rapid activation into lysine vasopressin (see Table 1) and eventual inactivation.

Example 3

The synthesis of $CH_3(CH_2)_6CO$-Gly-Gly-Gly-Cys-Tyr-Phe-Gln-Asn-Cys-Pro-Lys-Gly-$NH_2$ (SEQ ID NO: 36) (also referred to as C8TerA) with disulfide bonds between the two cysteine residues was done by custom peptide supplier Anaspec, San Jose, Calif., according to the inventor's specification. The known standard amino acids in the formula above are represented by three letter abbreviation know to those skilled in the art (see FIG. 4 for complete chemical formula). In this vasopressin analog, octanoic acid was attached to the N-terminal aminogroup of the peptide via amide bond formed between the carboxyl group of octanoic acid and the amino group of glycine. At the end of the synthesis the determined molecular mass was found to be 1354 Da corresponding to protonated peptide or the molecular ion peak on mass spectroscopic analysis. This was consistent with the theoretical molecular mass of 1354.4 Da when protonated. This peptide was water soluble, was a white powder, and was easily obtained at purity of greater than 90% in this case.

Example 4

The synthesis of $CH_3(CH_2)_6CO$—$OHC(CH_3)CO$-Gly-Gly-Gly-Cys-Tyr-Phe-Gln-Asn-Cys-Pro-Lys-Gly-$NH_2$ (SEQ ID NO: 37) (also referred to as C8TerE) with disulfide bonds between the two cysteine residues was done by Anaspec, San Jose, Calif., according to the inventor's specification. The known standard amino acids in the formula above are represented by three letter abbreviations know to those skilled in the art (see FIG. 5 for complete chemical formula). In this vasopressin analog, octanoic acid was attached to the hydroxyl group of lactic acid via ester bond and the carboxyl group of lactic acid was attached to the amino group of glycine via an amide bond. This provides an in vivo hydrolysable ester bond which is believed to be less stable than an amide bond and facilitates the removal of the 8 carbon fatty acid. At the end of the synthesis the determined molecular mass was found to be 1425.7 Da, corresponding to protonated peptide or the molecular ion peak on mass spectroscopic analysis. This was consistent with the theoretical molecular mass of 1426.5 Da when protonated. This peptide was water soluble, was a white powder and was easily obtained at purity of greater than 90% in this case.

Example 5

Figure 1:
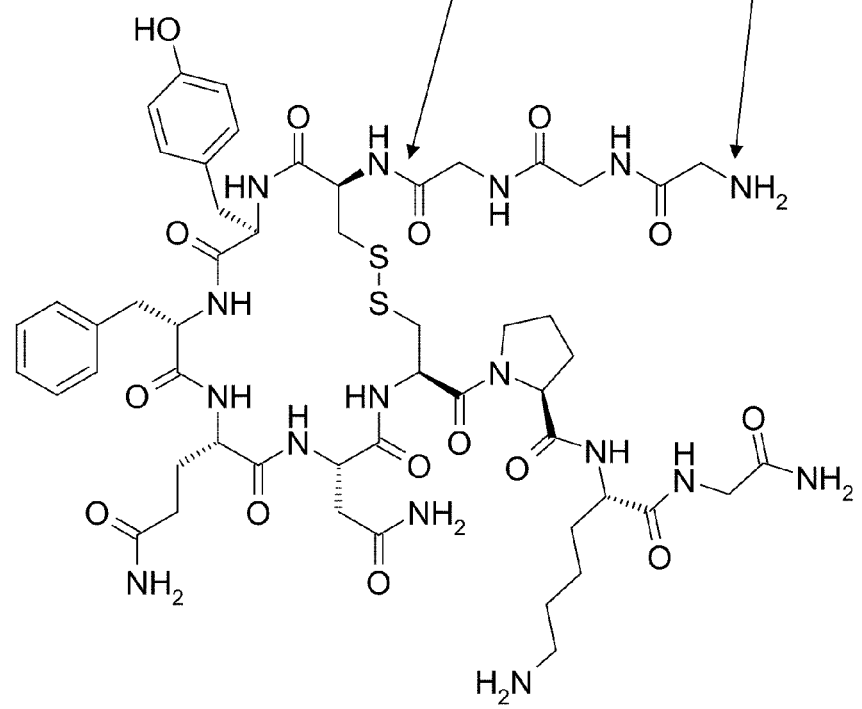
FIG. 1. The figure depicts a chemical structure of vasopressin with three glycine residues at the N-terminus. This structure is also known as terlipressin.
Figure 2:
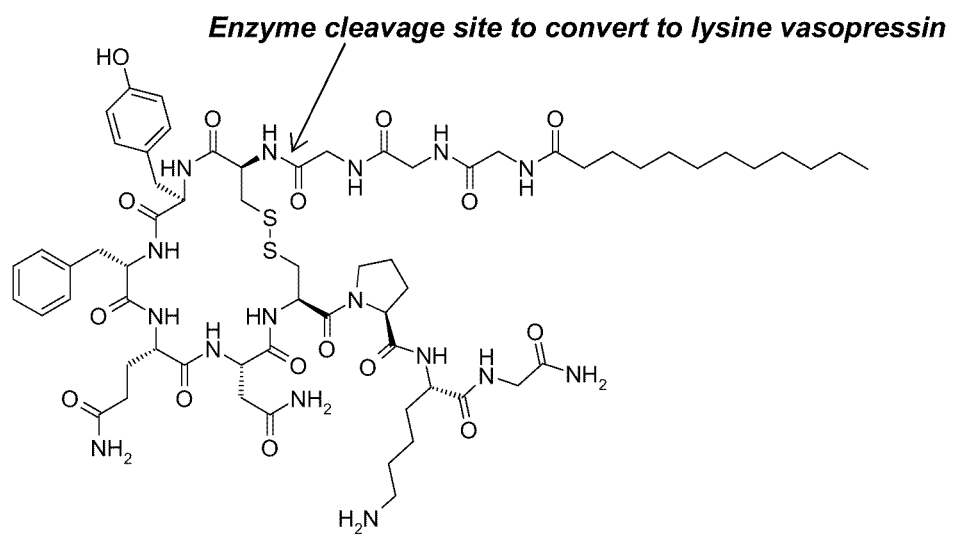
FIG. 2. The figure depicts a chemical structure of vasopressin with three glycine residues at the N-terminus attached to lauric acid. This is also referred to as "C12TerA". Using reverse phase HPLC chromatography in a Rainin (C18, 5 um, 4.6×250 mm), eluted with a linear gradient from water/0.1% TFA to 100% acetoinitrile/0.1% TFA over 20 minutes at a flow rate of 1 ml/min, the C12TerA showed retention time of 14.86 minutes as monitored at 215 nm and showed greater than 90% purity. Using mass spectrometer for total ion current, the purity was confirmed and a mass of 1409.5 Da was found corresponding to protonated peptide or the molecular ion peak on mass spectroscopic analysis. This is consistent with the theoretical molecular mass of 1410.4 Da when protonated. The absorption spectra showed a peak at 260 nm, which is 24 times less than at 210 nm.
Figure 3:
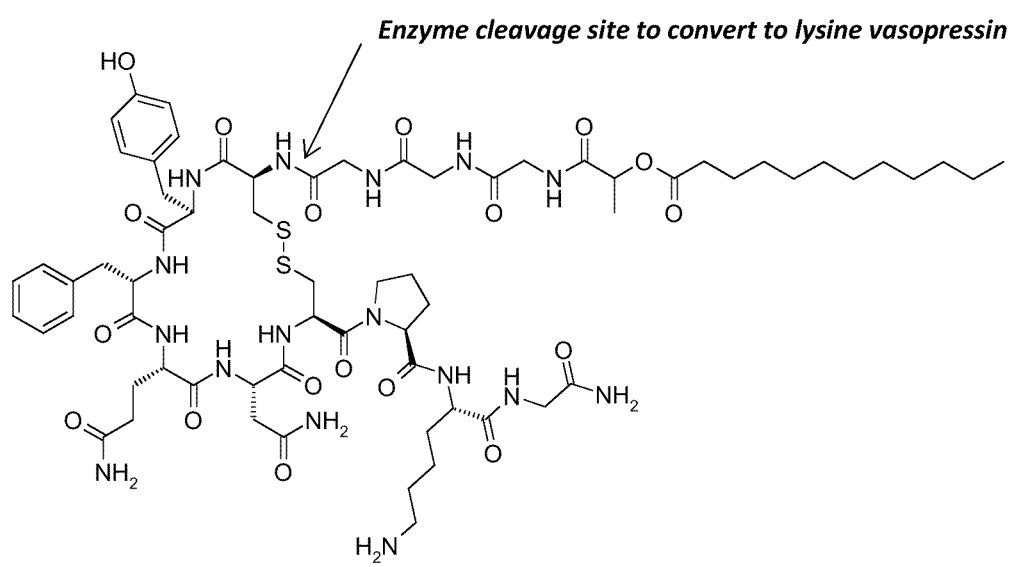
FIG. 3. The figure depicts a chemical structure of vasopressin with three glycine residues at the N-terminus attached to lauric acid via lactic acid ester. This is also referred to as "C12TerE". Using reverse phase HPLC chromatography in a Rainin (C18, 5 m, 4.6×250 mm) eluted with a linear gradient from 30% aetonitrile/water/0.1% TFA to 90% acetoinitrile/water/0.1% TFA over 45 minutes at a flow rate of 1 ml/min, the C12TerE showed retention time of 20.91 minutes as monitored at 220 nm and showed greater than 90% purity. Using mass spectrometer for total ion current the purity was confirmed and a mass of 1481.6 Dalton was found corresponding to protonated peptide or the molecular ion peak on mass spectroscopic analysis. This is consistent with the theoretical molecular mass of 1482.5 Dalton when protonated. The absorption spectra showed a peak at 260 nm, which is about 18 times less than at 220 nm.
Figure 4:
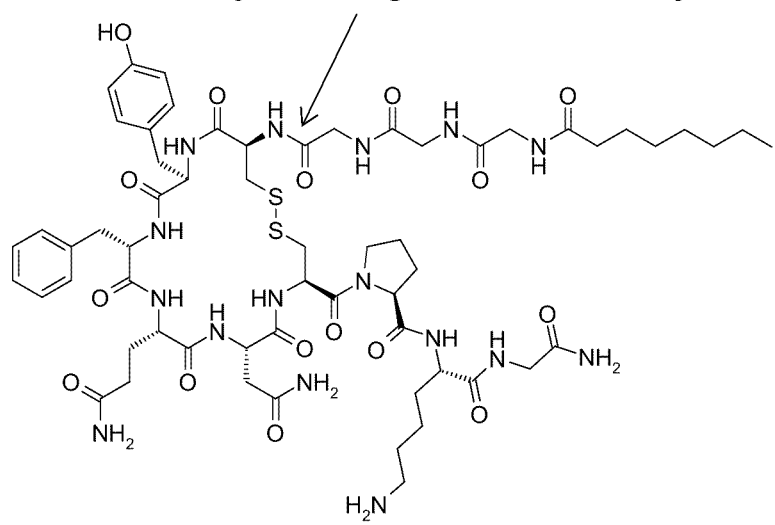
FIG. 4. The figure depicts a chemical structure of vasopressin with three glycine residues at the N-terminus attached to octanoic acid. This is also referred to as "C8TerA". Using reverse phase HPLC chromatography in a Rainin (C18, 5 μm, 4.6×250 mm) eluted with a linear gradient from 10% Acetonitrile/water/0.1% TFA to 70% acetoinitrile/water/0.1% TFA over 45 minutes at a flow rate of 1 ml/min, the C8TerA showed retention time of 23.17 minutes as monitored at 220 nm and showed greater than 90% purity. Using mass spectrometer for total ion current the purity was confirmed and a mass of 1354.0 Dalton was found corresponding to protonated peptide or the molecular ion peak on mass spectroscopic analysis. This is consistent with the theoretical molecular mass of 1354.4 Dalton when protonated. The absorption spectra showed a peak at 260 nm which is about 25 times less than at 210 nm.
Figure 6:
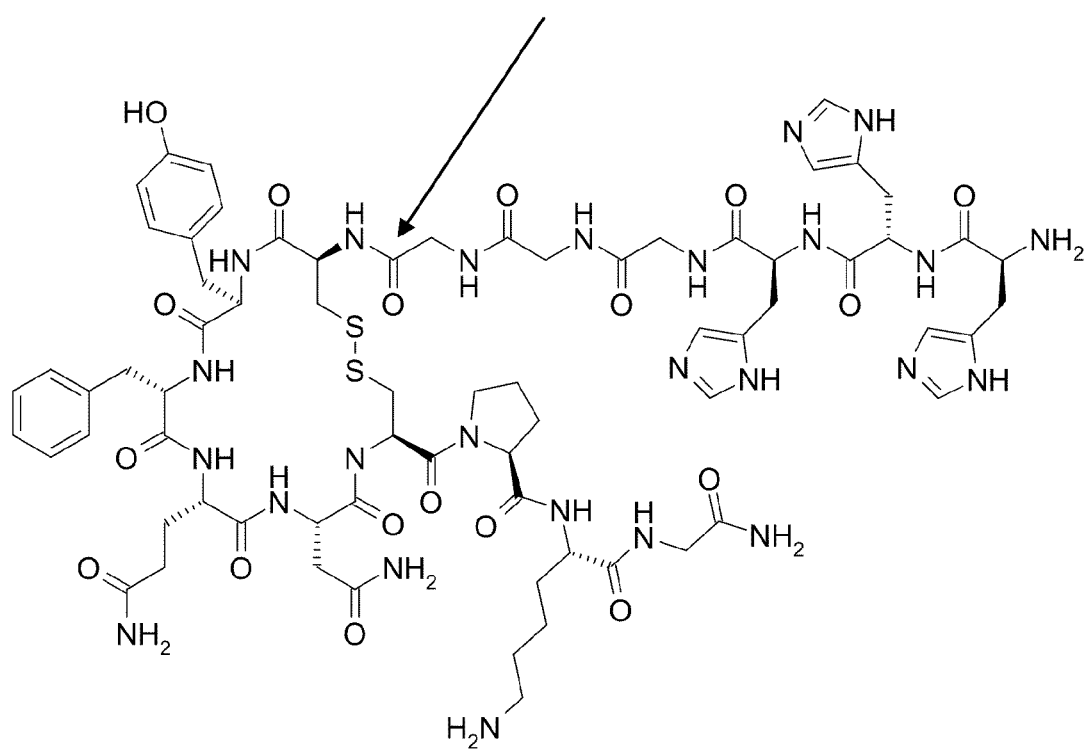
FIG. 6. The figure depicts a chemical structure of lysine vasopressin with three glycine residues at the N-terminus attached to three Histidine residues. This is also referred to as "His3Ter". Using reverse phase HPLC chromatography in a Supelco (C18, 5 μm, 4.6×250 mm) eluted with a linear gradient from 0% acetonitrile/water/0.1% TFA to 60% acetoinitrile/water/0.1% TFA over 45 minutes at a flow rate of 1 ml/min, the His3Ter showed retention time of 15.47 minutes as monitored at 220 nm and showed greater than 95% purity. Using mass spectrometer for total ion current the purity was confirmed and a mass of 1639.8 Dalton was found corresponding to protonated peptide or the molecular ion peak on mass spectroscopic analysis. This is consistent with the theoretical molecular mass of 1639.1 Dalton when protonated. The absorption spectra showed a peak at 260 nm, which is about 40 times less than at 210 nm.
Figure 7:
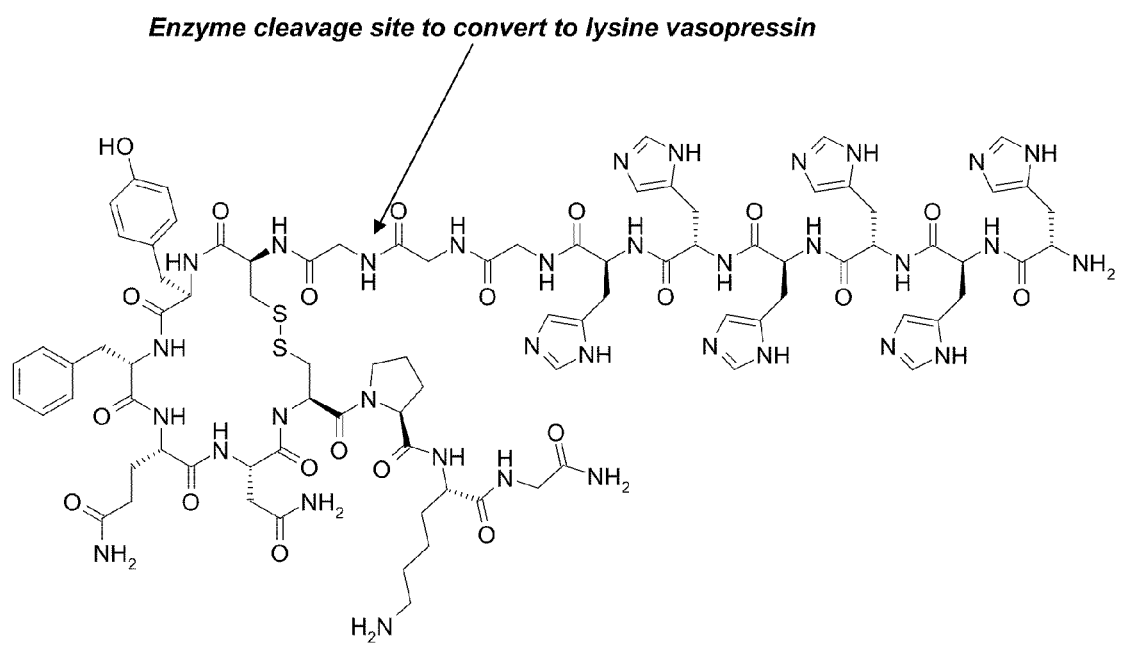
FIG. 7. The figure depicts a chemical structure of lysine vasopressin with three glycine residues at the N-terminus attached to six Histidine residues (SEQ ID NO: 52). This is also referred to as "His6Ter" ("His6" disclosed as SEQ ID NO: 52). Using reverse phase HPLC chromatography in a Vydac (C18, 5 μm, 4.6×250 mm) eluted with a linear gradient from 0% acetonitrile/water/0.1% TFA to 100% acetoinitrile/ water/0.1% TFA over 45 minutes at a flow rate of 1 ml/min, the His6Ter ("His6" disclosed as SEQ ID NO: 52) showed retention time of 18.81 minutes as monitored at 220 nm and showed greater than 95% purity. Using mass spectrometer for total ion current the purity was confirmed and a mass of 2051.3 Dalton was found corresponding to protonated peptide or the molecular ion peak on mass spectroscopic analysis. This is consistent with the theoretical molecular mass of 2051.1 Dalton when protonated. The absorption spectra showed a peak at 260 nm, which is about 42 times less than at 220 nm.

The synthesis of His-His-His-His-His-His-Gly-Gly-Gly-Cys-Tyr-Phe-Gln-Asn-Cys-Pro-Lys-Gly-$NH_2$ (SEQ ID NO: 38) (also referred to as His6Ter ("His6" disclosed as SEQ ID NO: 52)) with disulfide bonds between the two cysteine residues was done by Anaspec, San Jose, Calif., according to the inventor's specification. The known standard amino acids in the formula above are represented by three letter abbreviations known to those skilled in the art (see FIG. 7 for complete chemical formula). In this vasopressin analog, six histidine residues (SEQ ID NO: 52) were attached to the amino group of glycine via amide bond. This provided a metal binding domain that can be used to attach this vasopressin analog to a protective carrier containing metal chelate. Examples of metal chelate covalently linked to polymeric carrier include, but not limited to, $DTPA-Zn^{2+}$, $NTA-Zn^{2+}$, $DTPA-Ni^{2+}$, $NTA-Zn^{2+}$. The attachment will provide a slow release of this lysine vasopressin analog after administration to a patient. Further, those molecules that are released will be activated by enzymes in the body to effect conversion to vasopressin. At the end of the synthesis the determined molecular mass was found to be 2051.1 Da corresponding to protonated peptide or the molecular ion peak on mass spectroscopic analysis. This is consistent with the theoretical molecular mass of 2051.3 Da when protonated. This peptide was water soluble, was a white powder, and was easily obtained at purity of greater than 95% in this case.

Example 6

The synthesis of His-His-His-Gly-Gly-Gly-Cys-Tyr-Phe-Gln-Asn-Cys-Pro-Lys-Gly-NH$_2$ (SEQ ID NO: 39) (also referred to as His3Ter) with disulfide bonds between the two cysteine residues was done by Anaspec, San Jose, Calif., according to the inventor's specification. The known standard amino acids in the formula above are represented by three letter abbreviations known to those skilled in the art (see FIG. 8 for complete chemical formula). In this vasopressin analog, 3 histidine residues were attached to the amino group of the terminal glycine via an amide bond. This provided a metal binding domain that can be used to attach this vasopressin analog to a protective carrier containing metal chelate. Examples of metal chelate covalently linked to polymeric carrier include, but are not limited to DTPA-$Zn^{2+}$, NTA-$Zn^{2+}$, DTPA-$Ni^{2+}$, and NTA-$Zn^{2+}$. Additional carriers with metal chelate are disclosed in U.S. Pat. No. 7,138,105 B2, which is herein incorporated by reference. The attachment to a protective carrier will provide a slow release of this vasopressin analog after administration to a patient. Further, those molecules that are released will be activated by enzymes in the body to effect conversion to vasopressin. At the end of the synthesis the determined molecular mass was found to be 1639.1 Da, corresponding to protonated peptide or the molecular ion peak on mass spectroscopic analysis. This is consistent with the theoretical molecular mass of 1639.8 Da when protonated. This peptide was water soluble, was a white powder, and was easily obtained at purity of greater than 95% in this case.

Example 7

The synthesis of His-His-His-Gly-Gly-Gly-Cys-Tyr-Phe-Gln-Asn-Cys-Pro-Arg-Gly-NH$_2$ (SEQ ID NO: 40) (referred to as His3Vas) with disulfide bonds between the two cysteine residues were done by custom peptide supplier Anaspec, San Jose, Calif., according to the inventor's specification. The known standard amino acids in the formula above are represented by three letter abbreviations know to those skilled in the art (see FIG. 8 for complete chemical formula). In this arginine vasopressin analog, 6 histidines (SEQ ID NO: 52) were attached to the N-terminal aminogroup of the peptide via an amide bond formed between the carboxyl group of histidine and the amino group of glycine. This provides a metal binding domain that can be used to attach this vasopressin analog to a protective carrier containing metal chelate. Examples of metal chelate covalently linked to polymeric carrier include, but are not limited to DTPA-$Zn^{2+}$, NTA-$Zn^{2+}$, DTPA-$Ni^{2+}$, and NTA-$Zn^{2+}$. Additional carriers with metal chelate are disclosed in U.S. Pat. No. 7,138,105 B2 which is herein incorporated by reference. The attachment to the protective carrier will provide a slow release of this arginine vasopressin analog after administration to a patient. Further, those that are released will be activated by enzymes in the body to effect conversion to arginine vasopressin. At the end of the synthesis the determined molecular mass was found to be 1668 Da corresponding to protonated peptide or the molecular ion peak on Mass spectroscopic analysis. This was consistent with the theoretical molecular mass of 1667.9 Da when protonated. This peptide was water soluble, was a white powder, and was easily obtained at purity of greater than 95% in this case.

Example 8

The synthesis of His-His-His-His-His-His-Gly-Gly-Gly-Cys-Tyr-Phe-Gln-Asn-Cys-Pro-Arg-Gly-NH$_2$ (SEQ ID NO: 41) (referred to as His6Vas ("His6" disclosed as SEQ ID NO: 52)) with disulfide bonds between the two cysteine residues was done by custom peptide supplier Anaspec, San Jose, Calif., according to the inventor's specification. The known standard amino acids in the formula above are represented by three letter abbreviations know to those skilled in the art (see FIG. 9 for complete chemical formula. In this vasopressin analog, 6 histidines (SEQ ID NO: 52) were attached to the N-terminal aminogroup of the peptide via an amide bond formed between the carboxyl group of histidine and the amino group of glycine. This provides a metal binding domain that can be used to attach this vasopressin analog to a protective carrier containing metal chelate. Examples of metal chelate covalently linked to polymeric carrier include, but are not limited to DTPA-$Zn^{2+}$, NTA-$Zn^{2+}$, DTPA-$Ni^{2+}$, and NTA-$Zn^{2+}$. Additional carriers with metal chelate are disclosed in U.S. Pat. No. 7,138,105 B2, which is herein incorporated by reference. The attachment to protective carrier will provide a slow release of this arginine vasopressin analog after administration to a patient. Further, those that are released will be activated by enzymes in the body to effect conversion to arginine vasopressin. At the end of the synthesis the determined molecular mass was found to be 2080.5 Da corresponding to protonated peptide or the molecular ion peak on mass spectroscopic analysis. This is consistent with the theoretical molecular mass of 2079.3 Da when protonated. This peptide was water soluble, was a white powder, and was easily obtained at purity of greater than 95% in this case.

Example 9

The synthesis of the GLP-1 analogs SEQ ID NO: 2, SEQ ID NO: 3, SEQ ID NO: 4, and SEQ ID NO: 5 additionally containing iminodiacetic acid (IDA) or nitrilotriacetic acid (NTA) at the C-terminal was done by Anaspec, San Jose, Calif., according to the inventor's specification and procedures (the attachment is as shown in FIGS. 20 and 21, where the peptide is GLP as in SEQ ID NO: 2). The synthesis was initiated by attachment of iminodiacetic acid or nitrilotriacetic acid derivative (N',N',bis(carboxymethyl)-lysine with blocked epsilon amino group) to the Wang's resin followed by blocking of the remaining carboxyl groups. The syntheses yielded the following sequences:

```
                                          (SEQ ID NO: 42)
His-Ala-Glu-Gly-Thr-Phe-Thr-Ser-Asp-Val-Ser-Ser-
Tyr-Leu-Glu-Gly-Gln-Ala-Ala-Lys-Glu-Phe-Ile[[u]]-
Ala-Trp-Leu-Val-Lys-Gly-Arg-IDA;

(SEQ ID NO: 43)
His-Ala-Glu-Gly-Thr-Phe-Thr-Ser-Asp-Val-Ser-Ser-
Tyr-Leu-Glu-Gly-Gln-Ala-Ala-Lys-Glu-Phe-Ile[[u]]-
Ala-Trp-Leu-Val-Lys-Gly-Arg-Gly-IDA;

(SEQ ID NO: 44)
His-Ala-Glu-Gly-Thr-Phe-Thr-Ser-Asp-Val-Ser-Ser-
Tyr-Leu-Glu-Gly-Gln-Ala-Ala-Lys-Glu-Phe-Ile[[u]]-
Ala-Trp-Leu-Val-Lys-Gly-Arg-Gly-Gly-IDA;

(SEQ ID NO: 45)
His-Ala-Glu-Gly-Thr-Phe-Thr-Ser-Asp-Val-Ser-Ser-
Tyr-Leu-Glu-Gly-Gln-Ala-Ala-Lys-Glu-Phe-Ile[[u]]-
Ala-Trp-Leu-Val-Lys-Gly-Arg-Gly-Gly-Gly-IDA;
```

-continued

His-Ala-Glu-Gly-Thr-Phe-Thr-Ser-Asp-Val-Ser-Ser-
Tyr-Leu-Glu-Gly-Gln-Ala-Ala-Lys-Glu-Phe-Ile[[u]]-
Ala-Trp-Leu-Val-Lys-Gly-Arg-NTA;
(SEQ ID NO: 46)

His-Ala-Glu-Gly-Thr-Phe-Thr-Ser-Asp-Val-Ser-Ser-
Tyr-Leu-Glu-Gly-Gln-Ala-Ala-Lys-Glu-Phe-Ile[[u]]-
Ala-Trp-Leu-Val-Lys-Gly-Arg-Gly-NTA;
(SEQ ID NO: 47)

His-Ala-Glu-Gly-Thr-Phe-Thr-Ser-Asp-Val-Ser-Ser-
Tyr-Leu-Glu-Gly-Gln-Ala-Ala-Lys-Glu-Phe-Ile[[u]]-
Ala-Trp-Leu-Val-Lys-Gly-Arg-Gly-Gly-NTA;
and
(SEQ ID NO: 48)

His-Ala-Glu-Gly-Thr-Phe-Thr-Ser-Asp-Val-Ser-Ser-
Tyr-Leu-Glu-Gly-Gln-Ala-Ala-Lys-Glu-Phe-Ile[[u]]-
Ala-Trp-Leu-Val-Lys-Gly-Arg-Gly-Gly-Gly-NTA.
(SEQ ID NO: 49)

The first amino acid was attached to the secondary amino group of iminodiacetic acid or the primary amino group (after de-blocking) of N',N',bis(carboxymethyl)-lysine immobilized in the resin. This was followed by sequential addition of amino acids shown above according to the standard protocol known in the art. It should be noted that this example is not to limit the scope of the invention and that any GLP analog can be processed in a similar manner. It is also understood that in the present invention, the IDA and NTA can be attached to the R-group of any amino acids of GLP-1, except in the first six amino acids (His-Ala-Glu-Gly-Thr-Phe-Thr-Ser (SEQ ID NO: 75)) and in the N-terminal. In one particular example glycine was attached first. The number of glycines may vary from 0 to 3 before addition of arginine. This was followed by Arg, Gly, Lys and so on according to the above sequence. At the end of the synthesis the peptide was cleaved from the resin, deprotected, and purified. In this GLP-1 analog, iminodiacetic acid or nitrilotriacetic acid is at the C-terminal carboxyl group of the peptide. This also facilitates purification of the peptides using metal affinity column. More importantly, this provides additional metal binding domain to GLP-1 that can be used to attach this GLP-1 or its analogs to a protective carrier containing metal chelate. Examples of metal chelate covalently linked to polymeric carrier include, but are not limited to DTPA-$Zn^{2+}$, NTA-$Zn^{2+}$, DTPA-$Ni^{2+}$, and NTA-$Zn^{2+}$. Additional carriers with metal chelate are disclosed in U.S. Pat. No. 7,138,105 B2, which is herein incorporated by reference. The attachment to protective carrier provides a slow release of this GLP-1 or its analogs after administration to a patient.

Example 10

Testing of Biological Activity of Various Vasopressin Analogs

Ca-influx after vasopressin analog stimulation of human umbilical chord artery endothelial cells (HUAEC) was used to test the biological activity of the various vasopressin analogs. The material used were: 75 $cm^2$ tissue culture flasks, BD Bioscience, Bedford Mass. (catalogue number 137787) with 0.2 μm vented blue plug seal caps (catalogue number 353136); human umbilical artery endothelial cells (HUAEC), Lonza, Walkersville, Md. (catalogue number CC-2520); EGM-2 fully supplement medium, Lonza, Walkersville, Md. (catalogue number CC-3162); Fura-2 AM, Invitrogen/Molecular Probes, Carlsbad, Calif. (catalogue number F-1221) (Fura-2 AM is a high affinity, intracellular calcium indicator that is ratiometric and UV light-excitable; the acetoxymethyl (AM) ester form is useful for noninvasive intracellular loading as it is cell permeable. Once inside the cell the ester is clipped which renders the Fura-2 molecule cell impermeable and therefore trapped inside.); terlipressin derivatives custom made by Anaspec, San Jose Calif., according to inventors specifications; pooled human serum, Sigma, St. Louis, Mo. (catalogue number H4522); phosphate buffered saline (PBS), Fisher Scientific, Fair Lawn, N.J. (catalogue number BP399-500); trypsin-EDTA solution, 0.25%, Invitrogen/Gibco, Carlsbad, Calif. (catalogue number 25200-072); heat inactivated fetal bovine serum (FBS), Invitrogen/Gibco, Carlsbad, Calif. (catalogue number 10438-026); black polystyrene 96 well flat-bottom assay plates, Corning Inc., Corning, N.Y. (catalogue number 3916); Chameleon plate multilabel detection reader, Hidex, Turku, Finland, distributed by Bioscan, Washington, D.C.; dimethyl sulfoxide (DMSO), Fisher Scientific, Fair Lawn, N.J. (catalogue number D-136-1).

The methods used for tissue or cell culture are as follows: a vial of HUAEC (>0.5×$10^6$ cells) was thawed and seeded in two 75 $cm^2$ flasks with 15 ml EGM-2 medium each. Cells were grown over night and medium was changed. Media in the flasks were changed on a Monday, Wednesday, Friday schedule. Cells were split at approximately 80% confluency (using trypsin). Media were removed and the flasks were washed with 10 ml 1×PBS. The PBS was removed, 1.5 ml trypsin-EDTA solution was added and incubated for 5 min at 37° C. Three ml of FBS added and the cells were counted. The cells were centrifuged at 200×G for 5 min, resuspended in EGM-2 medium and distributed into new 75 cm2 flasks @ 3000-5000 cells per cm2.

To prepare for the Ca2+-influx assay, cells were distributed into one black 96 well plate @ $10^5$ cells/well. Cells were allowed to adhere overnight and the medium was then removed. Fifty μg Fura-2 was dissolved in 50 μl DMSO and added to 10 ml PBS/2% FBS. The cells were stained with 20 μl of 5 μg/ml Fura-2 in PBS/2% FBS for 2 h, then 180 μl EGM-2 medium supplemented with CaCl2 and glucose was added (10 mM CaCl2 and 11.1 mM glucose final concentrations).

To prepare analogs for testing, 50 uM terlipressin (or derivative) stock solution in DMSO was prepared. Incubation of 30 ml of the drugs (500 nM final concentration) in 3 ml 100% human serum (NOT heat inactivated) for 0, 1, 2, and 24 h was performed at 37° C. (placed on ice after incubation).

To measure Ca-influx, Fura-2 fluorescence was measured for 4 repetitions per well at 340 nm ex/510 nm em and 420 nm ex/510 nm em (4 measurement before and 16 after injection of drug. At t=12 sec, 20 μl of terlipressin or derivative was injected as a 500 nM solution (or serum) for a final concentration of 50 nM per well. Fura-2 fluorescence was measured for an additional 16 repetitions per well at 340 nm ex/510 nm em and 420 nm ex/510 nm em (4 measurements before and 16 after injection of drug). The controls included injected human serum alone, and terlipressin or derivative dissolved in PBS as negative controls. All measurements were done in hexuplicate.

Data analysis was done using Graphpad Prism version 5.0 software (Graphpad software Inc, San Diego, Calif.). Data were normalized by subtracting the baseline readings (the average of the first 4 repetitions of Fura-2 fluorescence measurement before the injection of drugs) from the readings after injection. The results of the experiments are shown in FIGS. 11-18. FIGS. 12-16 show 20 repeats of Fura-2 fluorescence as a function of time in seconds on the x-axis. The y-axis shows fluorescence intensity in relative fluorescence units [RFU]. After the first 4 data time points, the drugs are injected into the tissue culture well and fluorescence measurement is continued for 48 more seconds. Fura-2 fluorescence intensifies as intra-cellular $Ca^{2+}$ concentration rise in response to a stimulus FIG. 11 shows the ability of terlipressin and other vasopressin analog to be activated by serum after 2-hour incubation in human serum. The Y-axis is relative fluorescence units in human umbilical chord cells loaded with fura-2 in 96-well plate. The fluorescence is proportional to the calcium in cells cytoplasm. Vasopressin causes calcium influx into the cells cytoplasm causing an increase in fluorescence. Various vasopressin analogs were incubated with human serum for 2 hours and applied to cells in culture. Fluorescence were read every 3 seconds at time intervals for 1 minute as shown. After application, those samples that get activated by serum cause calcium influx and hence increase in fluorescence. In particular, the terlipressin analog C12TerA (labeled as C12Amide) caused pronounced calcium influx, relative to unmodified terlipressin and C12TerE (labeled as C12 ester).

FIGS. 12-13 shows that terlipressin is only fully active when injected in the presence of serum since, as being an analogue, a short sequence of amino acids needs to be cut off to leave fully active vasopressin. This step is very fast or the enzyme performing this step is active on ice as the addition of human serum increases terlipressin activity significantly without pre-incubation at 37° C. FIG. 12 shows that all analogs of vasopressin are inactive in PBS. FIG. 13 shows that terlipressin gets activated in serum quickly (into lysine vasopressin) and activity is seen immediately (at 0 hours) and losses activity immediately afterwards. Terlipressin once activated into lysine vasopressin loses its activity quickly due to further degradation in serum. Because of endogenous growth factors contained in human serum, human serum by itself produces a measurable Ca-influx signal. Activity of the drugs therefore needs to exceed the human serum signal. The C8TerA (C8Terlipressin amide), C12TerA (C12Terlipressin amide) and C12TerE (C8Terlipressin ester) which are the vasopressin analogs of the present invention gets activated in serum and remains active for up to 4 hr. The longer acting analogs are those with amide bond (see FIGS. 14-16).

FIG. 17 is a Scatchard plot showing the binding of C12TerA to polymeric carrier containing a hydrophobic group disclosed in U.S. patent application Ser. No. 11/613, 183, which is hereby incorporated by reference. The carrier also referred to as PGC-HC18 or 20PLPEG555-C18 is made up of polylysine of 15-30 kDa where 55% of the amino group is covalently modified to contain 5 kDa methoxypolyethylene glycol attached by through succinate linker and the remaining 45% of the amino group is amide bonded to stearic acid carboxyl group all disclosed in U.S. patent application Ser. No. 11/613,183. Two hundred fifty µl solutions of carrier (2.5 mg/tube) were mixed with 0.20, 0.15, 0.10, 0.075, 0.050, and 0.025 mg of C12 C12TerA. Sample was made up to 150 µl PBS and incubated overnight. The bound from 75 µl was eluted from Bio-spin-P30. The void volume containing loaded carrier was unloaded by filtration through 100 kDa MWCO filter after addition of 75 µl acetonitrile, to release load. The filtrate containing bound C12TerA was quantified by HPLC. A controlled passed through the same filter in 50% acetonitrile was used as a reference for the total C12TerA in each tube, allowing for the calculation of Free C12TerA in the original incubation mixture. C12-TerA elutes at 2.4 minutes. A gradient of 25-99% acetonitrile from 1-6 minutes at a flow rate of 1.5 ml/min was used. The column was Mercury MS 20×4 mm; 2 µm; C12 from Phenomenex. Although the Scatchard plot is not completely linear, an average Kd of 1-5 µM can be estimated, indicating a strong interaction of C12TerA with the carrier containing the hydrophobic group, which is sufficient to prolong the biological half-life of the C12TerA and delay its rapid activation and degradation. It should be noted that some C12TerA can form micelle and may be counted as bound due to the analytical techniques used.

The amount of C12TerA capable of being bound to a carrier was determined by varying the amount of the analog in the presence of 10 mg/ml hydrophobic group containing carrier PGC-HC18 or 20PLPEG555-C18. The carrier presented in the graph contains 20 kDa polylysine in which 55% of the epsilon amino group of polylysine was derivatized with 5 kDa methoxyPEG and 40% was derivatized by stearic acid. As shown in FIG. 18, most of the C12TerA was bound to the carrier containing hydrophobic group, which would be sufficient to prolong the biological half-life of the C12TerA and delay its rapid activation and degradation when administered to a patient.

Table 1 summarizes the results of the experiments in which the test samples were exposed to serum for the indicated periods of time and than assayed according to the methods described above. The results, expressed on a subjective scale as "−" for no detectable activity and "+" to "+++" for slight to high activity, respectively, indicate that terlipressin analogs with a C8 or C12 alkyl group bonded to the amide of terlipressin were able to protect the analog and maintain the biological activity of the activated terlipressin for at least 4 h. The results indicated that the addition of the hydrophobic group to terlipressin would be able to prolong the biological half-life of the C12TerA and delay its rapid activation and degradation when administered to a patient.

TABLE 1

Activity of Various Vasopressin Analogs

|  | 0 h* | 1 h | 2 h | 4 h |
| --- | --- | --- | --- | --- |
| Terlipressin | +++ | + | − | − |
| C8-Amide - Terlipressin | +++ | +++ | +++ | +++ |
| C12-Amide - terlipressin | +++ | +++ | +++ | +++ |
| C12-Ester - terlipressin | +++ | + | − | − |

*Time points refer to the amount of time the sample was pre-incubated in pooled human serum at 37° C. After the preincubation time the sample was placed on ice. 0 h time point contains the same amount of serum as the other sample s. Samples without serum added showed no activity. Plain serum was used as negative control.

Example 11

Testing of Biological Activity of Vasopressin Analogs in vivo

Using a rat ear model, a vasopressin analog with metal binding moiety of the present invention, His6Ter ("His6" disclosed as SEQ ID NO: 52), was evaluated for it ability to maintain vasoconstriction for an extended period of time. The analog was formulated at a 2% load in polymeric carrier containing 40PLPEG537-Zn-chelate. The peptide analog-polymeric complex was injected subcutaneously into the back of one set of rats, while terlipressin alone was also injected similarly in another set of rats. The ears were examined at baseline and at intervals up to 48 h. The ears of rats injected with the peptide analog in polymeric carrier had longer pharmacologic efficacy than the known long acting analog terlipressin as evidenced by the finding that the His6Ter analog ("His6" disclosed as SEQ ID NO: 52) plus polymeric carrier-treated rats had ears that remained pale at both the 6 and 24 h intervals, while the unformulated terlipressin-treated rats had ears that were pale at 6 h but had returned to a baseline color with grossly apparent normal blood flow at the 24 h interval.

Using the same model, the effects of delayed release of biologically-active lysine vasopressin from the peptide analog His6Ter ("His6" disclosed as SEQ ID NO: 52), with or without complexing in polymeric carrier, was tested. In the experiment, terlipressin was conjugated with a his tag metal binding moiety to result in the His6Ter peptide analog ("His6" disclosed as SEQ ID NO: 52). A portion of the His6Ter analog ("His6" disclosed as SEQ ID NO: 52) was formulated at 2% loading in 40PLPEG537-Zn-chelate. The three test materials were injected subcutaneously into groups of rats and the ears were examined after 6 and 24 h. Examination revealed that paling of ears was apparent for 24 h after subcutaneous injection of His6Ter ("His6" disclosed as SEQ ID NO: 52) formulated in 40PLPEG537-Zn-chelate while His6Ter ("His6" disclosed as SEQ ID NO: 52) alone and terlipressin alone show loss of paleness after 6 hours. The results demonstrate that the peptide analog complexed with polymeric carrier was able to result in sustained release of biologically-active lysine vasopressin for an extended period of time compared to terlipressin alone and to the His6Ter peptide analog ("His6" disclosed as SEQ ID NO: 52) not formulated with polymeric carrier.

Although the foregoing invention has been described in some detail by way of illustration and example for the purposes of clarity of understanding, one skilled in the art will easily ascertain that certain changes and modifications may be practiced without departing from the spirit and scope of the appended claims.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A composition comprising a peptide analog having a general formula: A-$(Cm)_x$-peptide, wherein:

a. Cm is any one of glycine, alanine, lysine, and arginine;

b. x is an integer from 3-6;

c. A is a chemical group or moiety comprising an alkyl group with 6 to 36 carbon units with a —$OCH(CH_3)CO$— linker attached to -$(Cm)_x$-peptide; and d. the A-$(Cm)_x$-peptide has lower biological activity in cell culture than the parent peptide in the absence of serum, wherein the peptide has at least 8 amino acids and is not SEQ ID NO: 53, or wherein the peptide is auristatin.

2. The composition of claim 1, further comprising a polymeric carrier with a plurality of hydrophobic groups of 8-36 carbons each, wherein group A of the peptide analog is non-covalently bound to the plurality of hydrophobic groups of the polymeric carrier by hydrophobic interaction.

3. The composition of claim 2, wherein the peptide is selected from vasopressin, glucagon like peptide (GLP), leptin fragment, gastric inhibitory polypeptide (GIP), epidermal growth factor (EGF) receptor ligand, EGF, transforming growth factor alpha (TGF-alpha), gastrin cholecystokinin receptor ligand, gastrin, cholecystokinin, auristatin, nisin, insulin, insulin-like growth factor, parathyroid hormone (PTH), atrial natriuretic factor, somatostatin, gonadotropin releasing hormone, leutinizing-hormone-releasing-hormone, and vasoactive intestinal peptide (VIP).

4. The composition of claim 2, wherein the peptide is GLP-1 and A-$(Cm)_x$- is attached to the C terminus of the peptide or a side chain.

5. The composition of claim 2, wherein A is a linear alkyl.

6. The composition of claim 3, wherein A is a linear alkyl.

7. The composition of claim 4, wherein A is a linear alkyl.

8. The composition of claim 2, wherein A is a branched alkyl.

9. The composition of claim 3, wherein A is a branched alkyl.

10. The composition of claim 4, wherein A is a branched alkyl.

11. The composition of claim 1, wherein the peptide is selected from glucagon like peptide (GLP), leptin fragment, gastric inhibitory polypeptide (GIP), epidermal growth factor (EGF) receptor ligand, EGF, transforming growth factor alpha (TGF-alpha), gastrin cholecystokinin receptor ligand, gastrin, cholecystokinin, auristatin, nisin, insulin, insulin-like growth factor, parathyroid hormone (PTH), atrial natriuretic factor, somatostatin, gonadotropin releasing hormone, leutinizing-hormone-releasing-hormone, and vasoactive intestinal peptide (VIP).

12. The composition of claim 1, wherein the peptide is GLP-1 and A-$(Cm)_x$- is not attached to the N terminus of the peptide.

13. The composition of claim 1, wherein A is a linear alkyl.

14. The composition of claim 11, wherein A is a linear alkyl.

15. The composition of claim 12, wherein A is a linear alkyl.

16. The composition of claim 1, wherein A is a branched alkyl.

17. The composition of claim 12, wherein A is a branched alkyl.

18. The composition of claim 12, wherein A is a branched alkyl.

19. A method of making a composition comprising a peptide analog comprising:

forming a covalent bond between a parent peptide and a group A-$(Cm)_x$- (reactive group) to form a composition comprising peptide analog according to claim 1, where said peptide analog has lower biological activity in cell culture than the parent peptide in the absence of serum.

20. A method for treatment of diabetes in a subject comprising administering the composition of claim 4 or the composition of claim 12 to a patient in need thereof.

* * * * *